(12) United States Patent
Park

(10) Patent No.: US 11,439,467 B1
(45) Date of Patent: Sep. 13, 2022

(54) KNEE REPLACEMENT SURGICAL CUT PLANES ESTIMATION FOR RESTORING PRE-ARTHRITIC ALIGNMENT

(71) Applicant: Lento Medical Inc., Houston, TX (US)

(72) Inventor: Ilwhan Park, Walnut Creek, CA (US)

(73) Assignee: LENTO MEDICAL, INC., Houston, TX (US)

( * ) Notice: Subject to any disclaimer, the term of this patent is extended or adjusted under 35 U.S.C. 154(b) by 583 days.

(21) Appl. No.: 16/565,818

(22) Filed: Sep. 10, 2019

(51) Int. Cl.
| | |
|---|---|
| *A61B 34/10* | (2016.01) |
| *A61B 17/15* | (2006.01) |
| *G16H 30/40* | (2018.01) |
| *G16H 20/40* | (2018.01) |
| *A61B 5/00* | (2006.01) |
| *A61B 17/56* | (2006.01) |

(52) U.S. Cl.
CPC ............ *A61B 34/10* (2016.02); *A61B 5/4528* (2013.01); *A61B 17/155* (2013.01); *A61B 17/157* (2013.01); *G16H 20/40* (2018.01); *G16H 30/40* (2018.01); *A61B 2017/564* (2013.01); *A61B 2034/102* (2016.02); *A61B 2034/105* (2016.02); *A61B 2034/108* (2016.02)

(58) Field of Classification Search
CPC ... A61B 5/4528; A61B 17/155; A61B 17/157; A61B 17/1764; A61B 2017/564; A61B 2034/102; A61B 2034/105; A61B 2304/108

See application file for complete search history.

(56) References Cited

U.S. PATENT DOCUMENTS

| | | | |
|---|---|---|---|
| 8,588,892 | B2 | 11/2013 | Hladio et al. |
| 8,608,749 | B2 | 12/2013 | Meridew et al. |
| 8,702,686 | B2 | 4/2014 | Geebelen et al. |
| 8,706,197 | B2 | 4/2014 | Henning et al. |
| 8,979,856 | B2 | 3/2015 | Catanzarite et al. |
| 9,066,727 | B2 | 6/2015 | Catanzarite et al. |

(Continued)

FOREIGN PATENT DOCUMENTS

WO   WO2010063117 A1   6/2010

OTHER PUBLICATIONS

Software User Manual, "SurgiCase Knee Planner", Ver 3.3, Jun. 6, 2018, materialize.com, Belgium, 49 pages.

(Continued)

*Primary Examiner* — Samuel S Hanna
(74) *Attorney, Agent, or Firm* — Mark Protsik; Thomas Schneck

(57) ABSTRACT

A computer-aided pre-operative planning tool with interactive surgeon interface for total knee replacement implements a method that allows implant size selection, implant positioning, and surgical cut planes estimation (with construction of corresponding surgical jig), based upon a series of coronal, axial and sagittal image slices of a patient's leg. Limb alignment and corresponding surgical cut planes are defined based upon joint anatomical-matching analysis to minimize joint wear and restore a pre-arthritic alignment (rather than an always fully neutral alignment). Using the interface, a surgeon has the option to adjust the varus/valgus alignment within recommended bounds between the pre-arthritic and fully neutral alignments. Implant size may be selected based on a best fit to the patient's leg obtained from analysis of the images.

16 Claims, 45 Drawing Sheets

(56) References Cited

U.S. PATENT DOCUMENTS

| | | | |
|---|---|---|---|
| 9,339,226 | B2 | 5/2016 | van der Walt et al. |
| 9,339,281 | B2 | 5/2016 | Keepler et al. |
| 9,579,112 | B2 | 2/2017 | Catanrarite et al. |
| 9,649,160 | B2 | 5/2017 | van der Walt et al. |
| 9,775,725 | B2 | 10/2017 | van der Walt et al. |
| 9,852,509 | B2 | 12/2017 | Park |
| 9,883,871 | B2 | 2/2018 | Park |
| 10,139,807 | B2 | 11/2018 | Park |
| 10,163,270 | B2 | 12/2018 | Gotte et al. |
| 10,231,745 | B2 | 3/2019 | Geebelen et al. |
| 10,350,089 | B2 | 7/2019 | Hook et al. |
| 10,762,623 | B2 | 9/2020 | Geebelen et al. |
| 10,918,439 | B2 | 2/2021 | Haidacher et al. |
| 2007/0276224 | A1 | 11/2007 | Lang et al. |
| 2009/0270868 | A1* | 10/2009 | Park .................. A61B 17/15 703/11 |
| 2011/0184419 | A1 | 7/2011 | Meridew et al. |
| 2011/0282473 | A1 | 11/2011 | Pavlovskaia et al. |
| 2013/0150862 | A1 | 6/2013 | Aram et al. |
| 2014/0115872 | A1 | 5/2014 | Steines et al. |
| 2014/0148809 | A1 | 5/2014 | Schmalzried et al. |
| 2015/0088142 | A1 | 3/2015 | Gibson |
| 2015/0105698 | A1 | 4/2015 | Park |
| 2018/0296226 | A1 | 10/2018 | Park |
| 2019/0223886 | A1 | 7/2019 | Fritzinger |

OTHER PUBLICATIONS

Software User Guide revision 2.0, "TraumaCAD", Ver 2.5, Jan. 31, 2019, 114 pages.

Printout: FDA Submission, 41 pages.

A. Durandet et al., "Radiographic analysis of lower limb axial alignments", Proceedings of the World Congress on Engineering, 2013, vol. II, WCE 2013, Jul. 3-5, 2013 London UK, 6 pages.

H. Kawakami et al., "Effects of rotation on measurement of lower limb alignment for knee osteotomy", Journal of Orthopaedic Research, 22, 2004, pp. 1248-1253.

R.G. Marx et al., "Reliability of lower extremity alignment measurement using radiographs and PACS", Knee Surg Sports Traumatol Arthrosc, 2011, 19:1693-1698.

G. McDaniel et al., A comparison of five approaches to measurement of anatomic knee alignment from radiographs, NIH Public Access, Author Manuscript, Osteoarthritis Cartilage, 2010, Feb., 18(2): 273.

U. Prakash et al., "Computerised measurement of tibiofemoral alignment", Journal of Bone & Joint Surgery (Br), vol. 83-B, No. 6, Aug. 2001, pp. 819-824.

M. Roland et al., "Virtual axis finder: a new method to determine the two kinematic axes of rotation for the tibio-femoral joint", Journal of Biomechanical Engineering, Jan. 2010, vol. 132, 9 pages.

E.A. Sled et al., "Reliability of lower limb alignment measures using an established landmark-based method with a customized computer software program", NIH Public Access, Author Manuscript, Rheumatol Int., Jan. 2011, 31(1), 71-77, 14 pages.

T. Takahashi et al., "A new computer-assisted method for measuring the tibio-femoral angle in patients with osteoarthrtis of the knee", Int'l Cartilage Repair Society, Osteoarthritis and Cartilage, 2004, vol. 12, No. 3, pp. 256-259.

Printout: Lexi Co., Ltd., "Zed View JIGEN", 3D Total Knee Arthroplasty Pre-Operative Planning Jig-Simulation, 2 pages.

N.V. Bardakos et al., "Customised Jigs in Primary Total Knee Replacement", Orthopedic & Muscular System: Current Research, Apr. 28, 2014, 7 pages.

* cited by examiner

Simutaneous Rotation of Three Views

Proximal Tibia Center

Proximal Tibia Line

Tibia Segmentation for Wear Algorithm

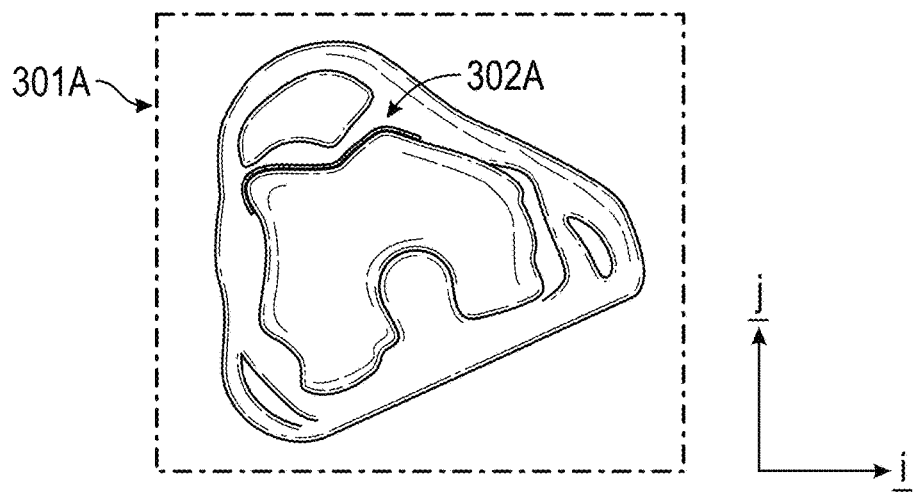
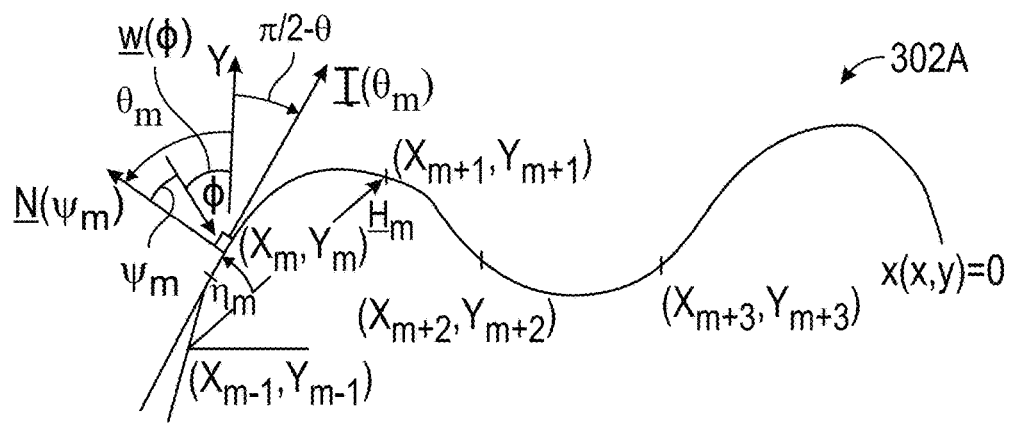
FIG. 19A
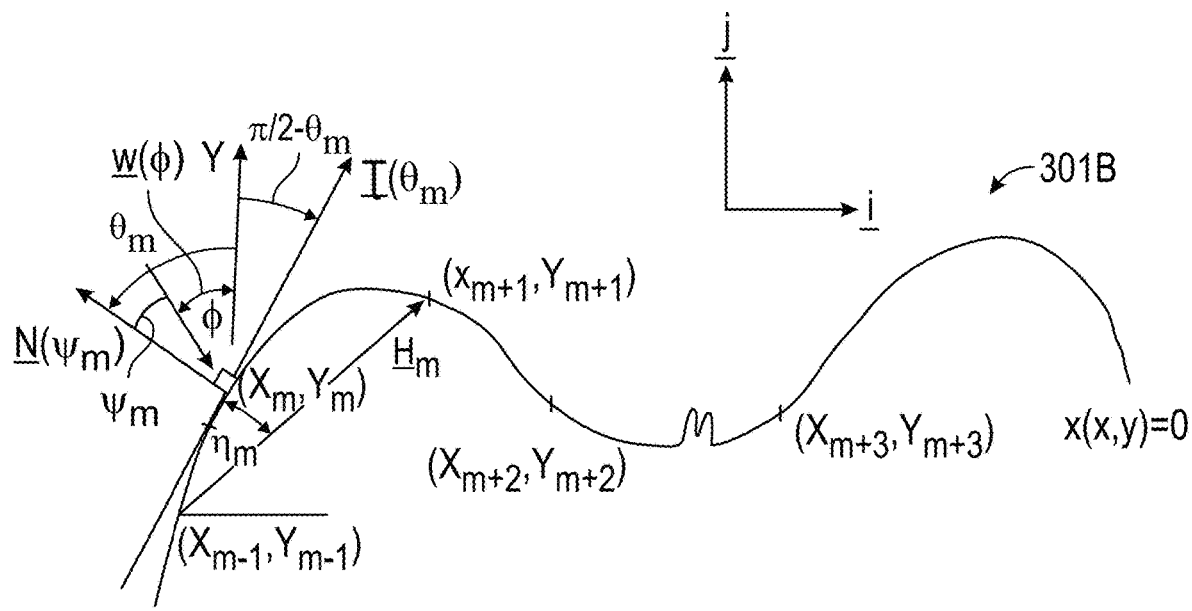
FIG. 19B

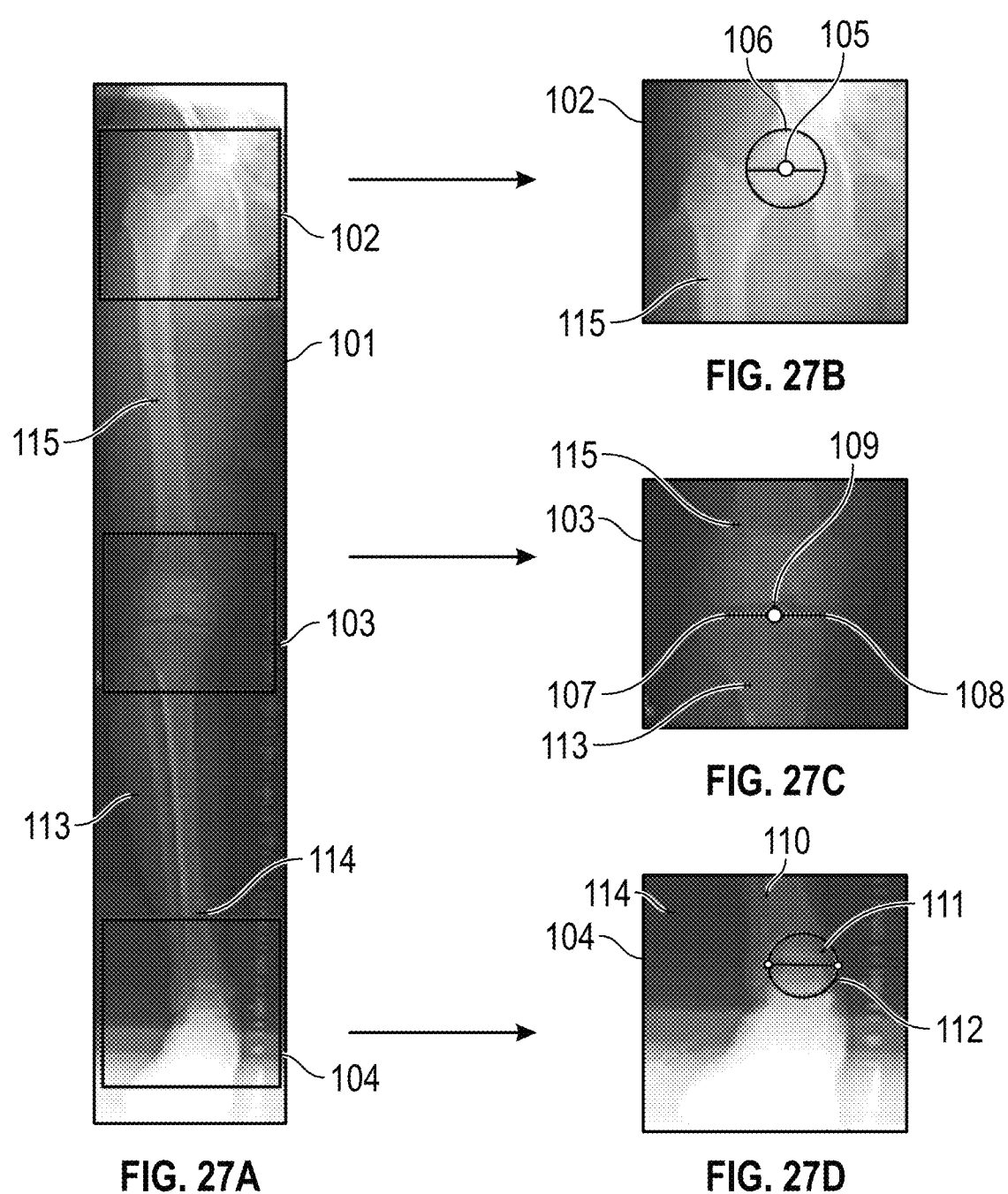

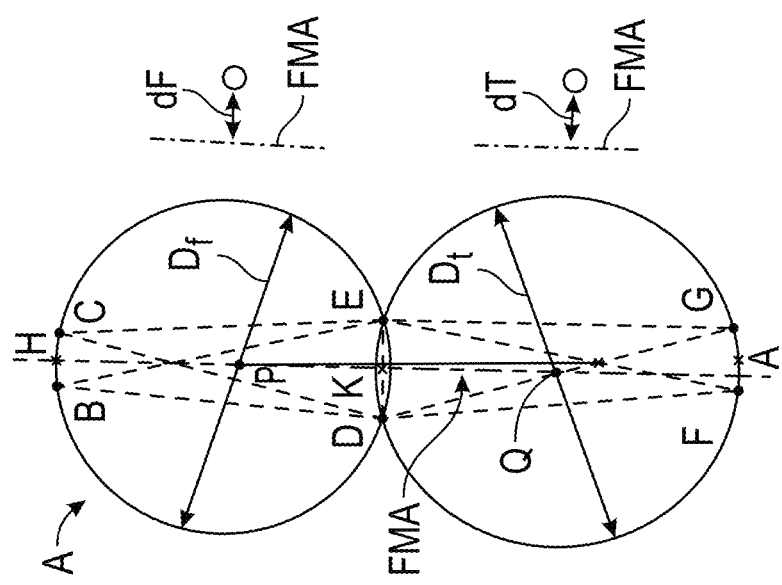
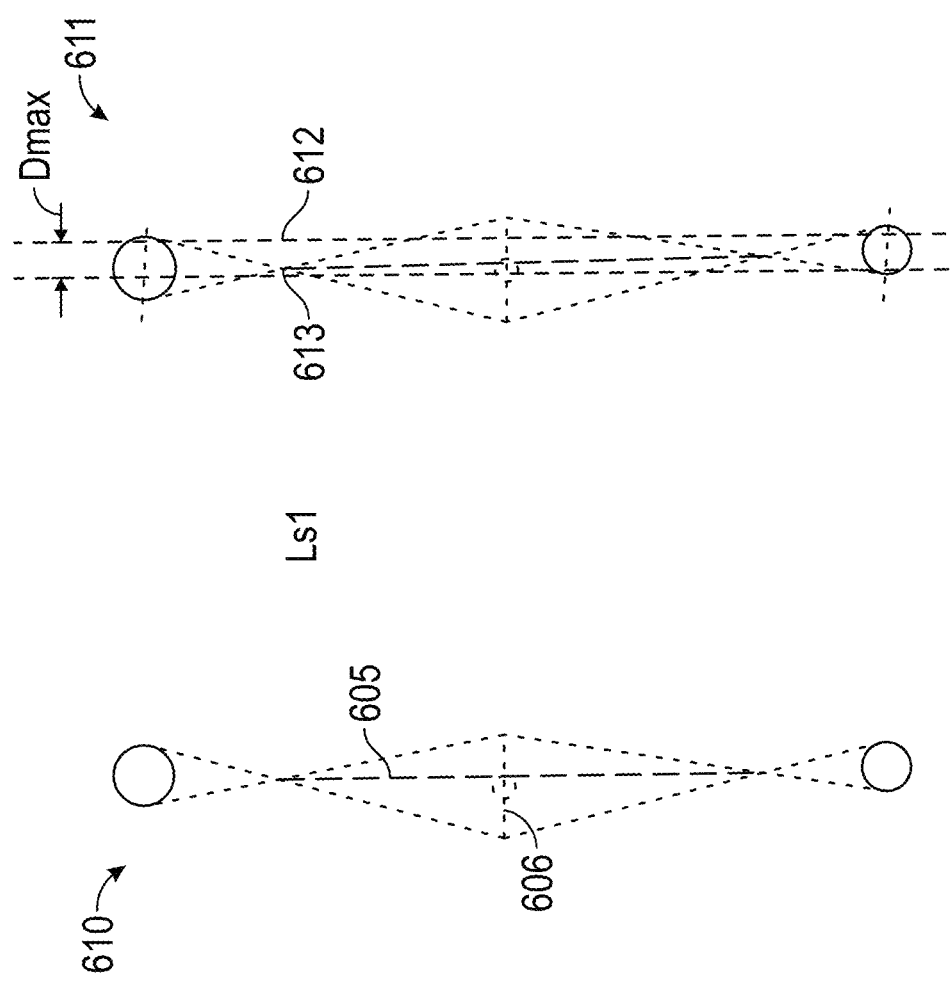
FIG. 32C
FIG. 32B
FIG. 32A

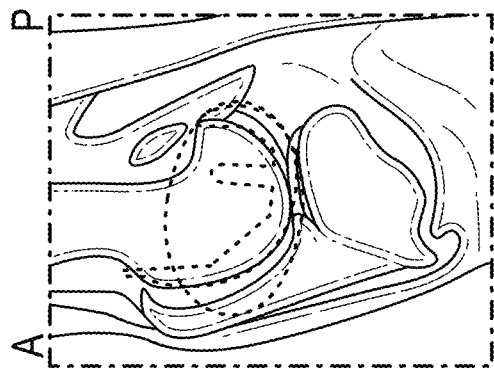
FIG. 37C
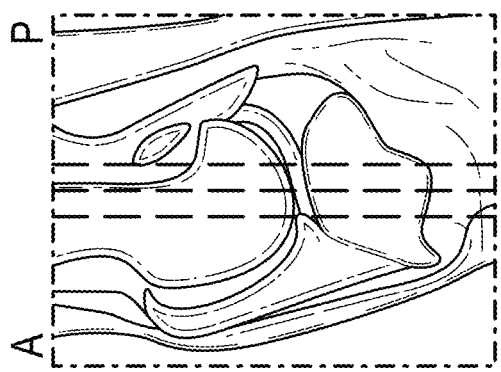
FIG. 38C
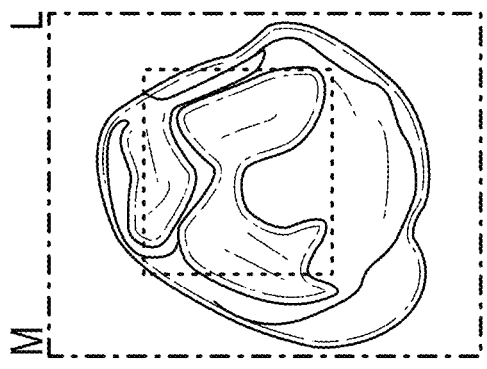
FIG. 37B
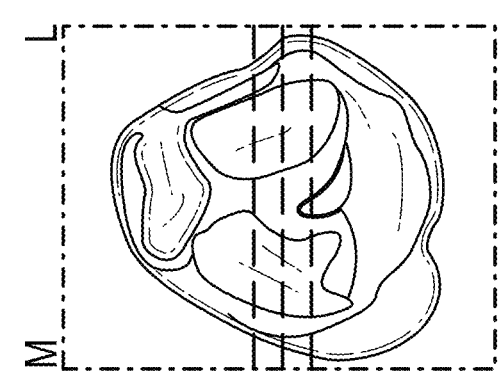
FIG. 38B
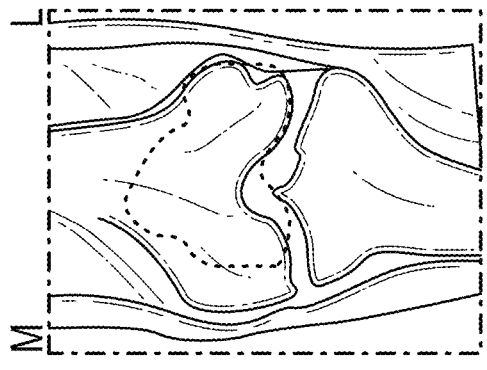
FIG. 37A
FIG. 38A

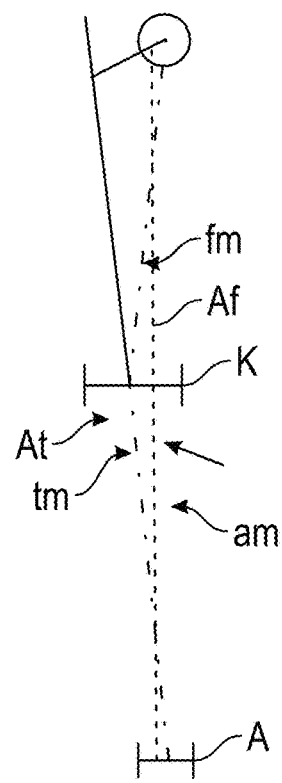
FIG. 48
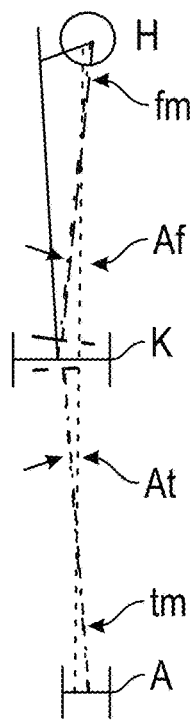 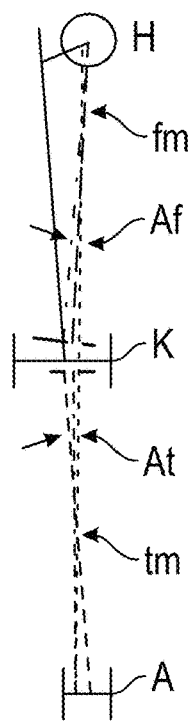 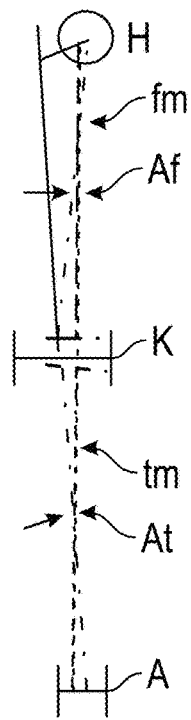
FIG. 49A   FIG. 49B   FIG. 49C

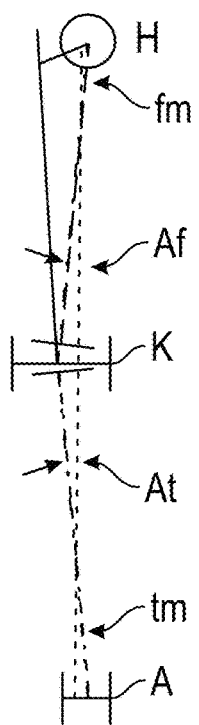 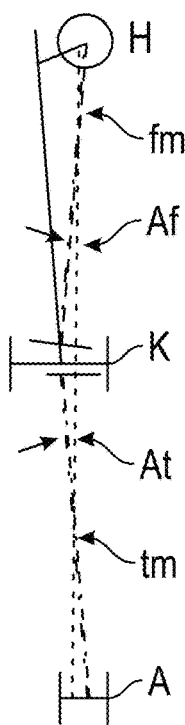 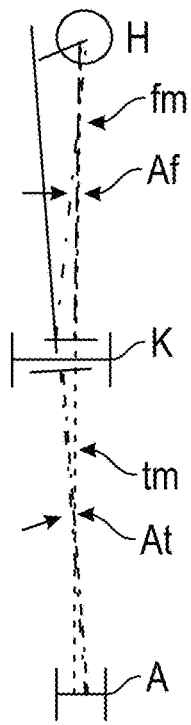
FIG. 50A  FIG. 50B  FIG. 50C
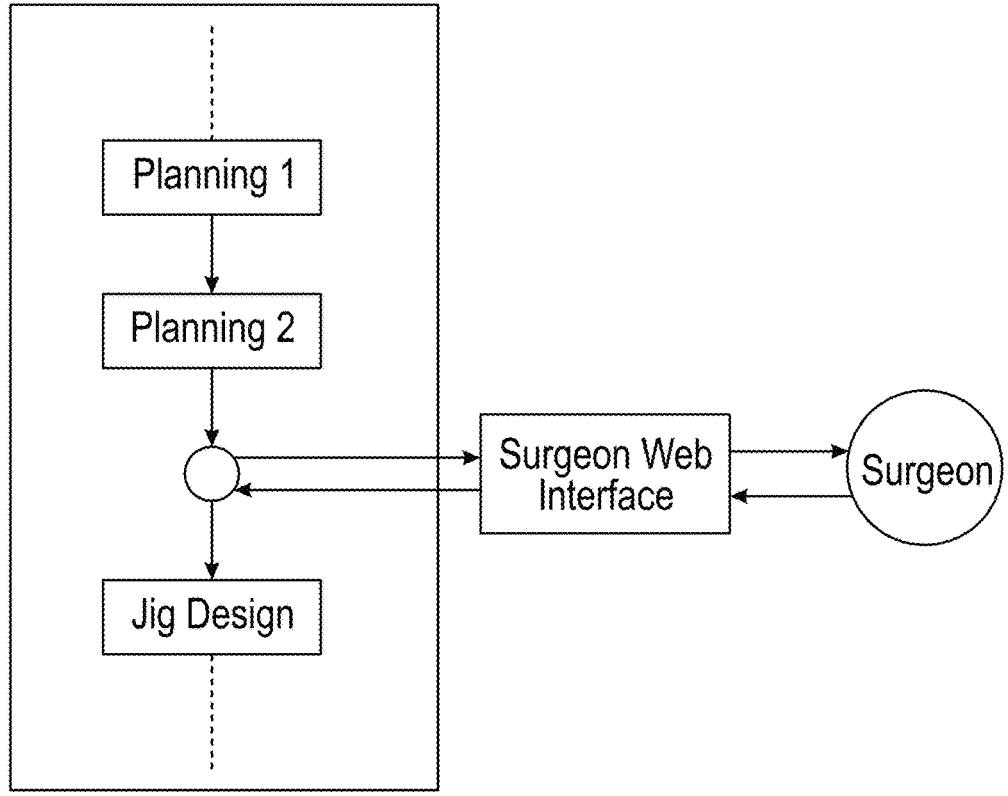
FIG. 51

KNEE REPLACEMENT SURGICAL CUT PLANES ESTIMATION FOR RESTORING PRE-ARTHRITIC ALIGNMENT

TECHNICAL FIELD

The invention relates to computer-aided knee replacement pre-planning, including patient-specific image-based tools for assisting with implant size selection and surgical cut planes estimation for knee replacement surgery.

BACKGROUND ART

Establishing femoral and tibial cut planes for proper positioning of an artificial replacement joint is important for successful patient outcomes. Typically, surgeons choose cut planes (and obtain corresponding surgical jigs for guiding the cuts during surgery) so that the new tibio-femoral mechanical alignment will be close to vertical or neutral, that is, neither varus (bowlegged) nor valgus (knock-kneed), as determined, e.g., from coronal plane images of the entire limb from hip to knee to ankle. While successful results are obtained for many patients whose original alignment was already close to neutral (usually within 3 degrees or less), outcomes are generally less successful for those patients whose original pre-arthritic alignment already deviated more than 3 degrees from neutral. This is due, at least in part, to the preexisting lengths of knee ligaments that need to be reattached at the end of surgery. In those cases, trying to artificially create neutral limb alignment can both adversely limit total range of knee motion (often 90 degrees or less) and possibly create eventual problems elsewhere in the skeletal system (e.g. at the corresponding hip joint, in the spinal column, or joints in the opposite limb).

Therefore, pre-operative planning is an important step prior to total knee replacement surgery. Precise analysis of an array of coronal and/or axial and/or sagittal images of the joint, allows an orthopedic surgeon and implant supplier to uniquely match a patient's leg anatomy to an appropriately sized set of femoral and tibial implants and to corresponding surgical cut planes for optimum patient outcomes. Each image of a patient's limb is represented by projections of part or all of an articulated surface joint ("ASJ") structure. These projections are ideally provided as a set of thin planar "slices" formed by magnetic resonance images (MRI) or computed tomography (CT) images (referred to collectively herein as "MRI images"), which may be associated with one or more coronal, axial and/or sagittal views of the ASJ structure.

At present, orthopedic surgeons usually perform the pre-operative planning using a 2-dimensional X-ray image to estimate the positions of femoral and tibial components. But 2-D X-ray is quite limited for a surgeon to precisely estimate the patient's anatomy due to the following: (1) 2-D X-ray radiograph is usually oriented off from true coronal view by up to 15 degrees; (2) the pre-arthritic state of a patient's knee, especially estimation of the pre-arthritic state of the so-called joint line of knee extension, is very difficult to analyze with a 2-D X-ray.

What is needed is a way to simultaneously orient MRI images of a patient's leg, represented by three MRI sets of femoral head, knee joint and ankle images, in order to provide a true coronal view of that patient's leg. Additionally, a method to estimate the joint line of the pre-arthritic state of the patient's knee joint is needed. Furthermore, a method to correctly estimate the joint line of the pre-arthritic state of patient knee joint is necessary to obtain optimal stability of the leg after surgery.

SUMMARY DISCLOSURE

The present invention largely restores the original pre-arthritic joint alignment and constructs surgical jigs with the appropriate cut planes. To do this, one must estimate the location and alignment of the original tibio-femoral joint to within about 0.4 degree from a patient's X-ray images or the series of MRI slices (or both), and from an anatomical matching analysis, despite damage that is evident in the existing joint. A range of choices is offered to the surgeon within appropriate bounds, such as at most 3 degrees of the estimated original alignment, so that a fully neutral or close-to-neutral post-surgical alignment might become available, with due regard, e.g. to the alignment of the opposite limb or the condition of the associated hip and ankle joints.

Accordingly, a method and corresponding computer-implemented tool are provided for selecting implant sizes and for making a surgical jig with a cut plane to guide bone resectioning in knee replacement surgery, wherein the cut plane is estimated from patient-specific images. The method begins by obtaining a series of images of a leg of a patient, including at least one whole-leg coronal image showing hip, knee, and ankle, along with a set of coronal, axial and sagittal image slices of respective hip, knee, and ankle joints. Next, one estimates from this series of images, and based on a joint anatomical-matching and/or wear mechanism model, a pre-arthritic tibio-femoral mechanical alignment of the leg. A desired tibio-femoral mechanical realignment of the leg is established that is closer to a neutral alignment. In accord with this desired tibio-femoral mechanical realignment, a cut plane for the surgical jig is determined. A surgical jig is constructed using a set of bone-jig contact surfaces dimensioned from the series of images. The jig has one and only one mechanical self-locking position. The jig has a bone cutting guide that defines the cut plane as per the desired alignment.

In this method, a lattice truss model is introduced to describe the pre-arthritic leg limb alignment. Based on this model, a medial/lateral bound is established to obtain the optimal stability of the leg.

BRIEF DESCRIPTION OF THE DRAWINGS

FIGS. 19A and 19B illustrate a two-dimensional curve, $\chi(x,y)=0$, representing one MRI slice or CT slice of an ASJ structure, and several angles associated with each location on the curve, (i) for a wear vector directed normal to the local ASJ structure and (ii) for a shear vector directed normal and tangential to the local ASJ structure.

FIG. 27A is a stand-up X-ray of over-all limb alignment of leg.

FIG. 27B is a region of femoral head represented by the circle as a model

FIG. 27C is knee joint region and the joint line is shown where medial and lateral condyles contact the medial/lateral tibial plateau points.

FIG. 27D is ankle region which displays ankle medial/lateral bound as a circle.

FIG. 32A illustrates the establishment of the lattice truss structure based on the results of wear algorithm.

FIG. 32B shows the maximum gap distance Dmax with respect the joint line.

FIG. 32C shows application of Ptolemy's inequality to the lattice truss structure for optimized best fit.

FIGS. 37A-37C are respective coronal, axial, and sagittal views for femoral implant positioning, with superimposed outlines of the planned femoral implant.

FIG. 38A-38C are respective coronal, axial, and sagittal views of a knee joint with a choice of anterior-posterior positions for the femur implant. The center line represents the calculated best position, while the outer lines represent position extremes between which a surgeon may select a position to be used in the surgery.

FIG. 48 is a geometric diagram of leg alignment parameters for illustrating bounds for alignment angle choices.

FIGS. 49A-49C, and 50A-50C are geometric diagrams as in FIG. 48 illustrating three possible resection angles for the femur and tibia, respectively.

FIG. 51 is a schematic flow diagram illustrating location of the surgeon web interface tool within the overall planning.

FIG. 52 has double slots, FIG. 53 has a single slot and saw blocker, and FIG. 54 has a single slot and open end, for differing permitted ranges of motion for a reciprocal saw in the defined cut plane.

FIG. 55 has double slots, FIG. 56 has a single slot and saw blocker, FIG. 57 has a single slot and open end for differing permitted ranges of motion for a reciprocal saw in the defined cut plane.

DETAILED DESCRIPTION

Figure 1A:
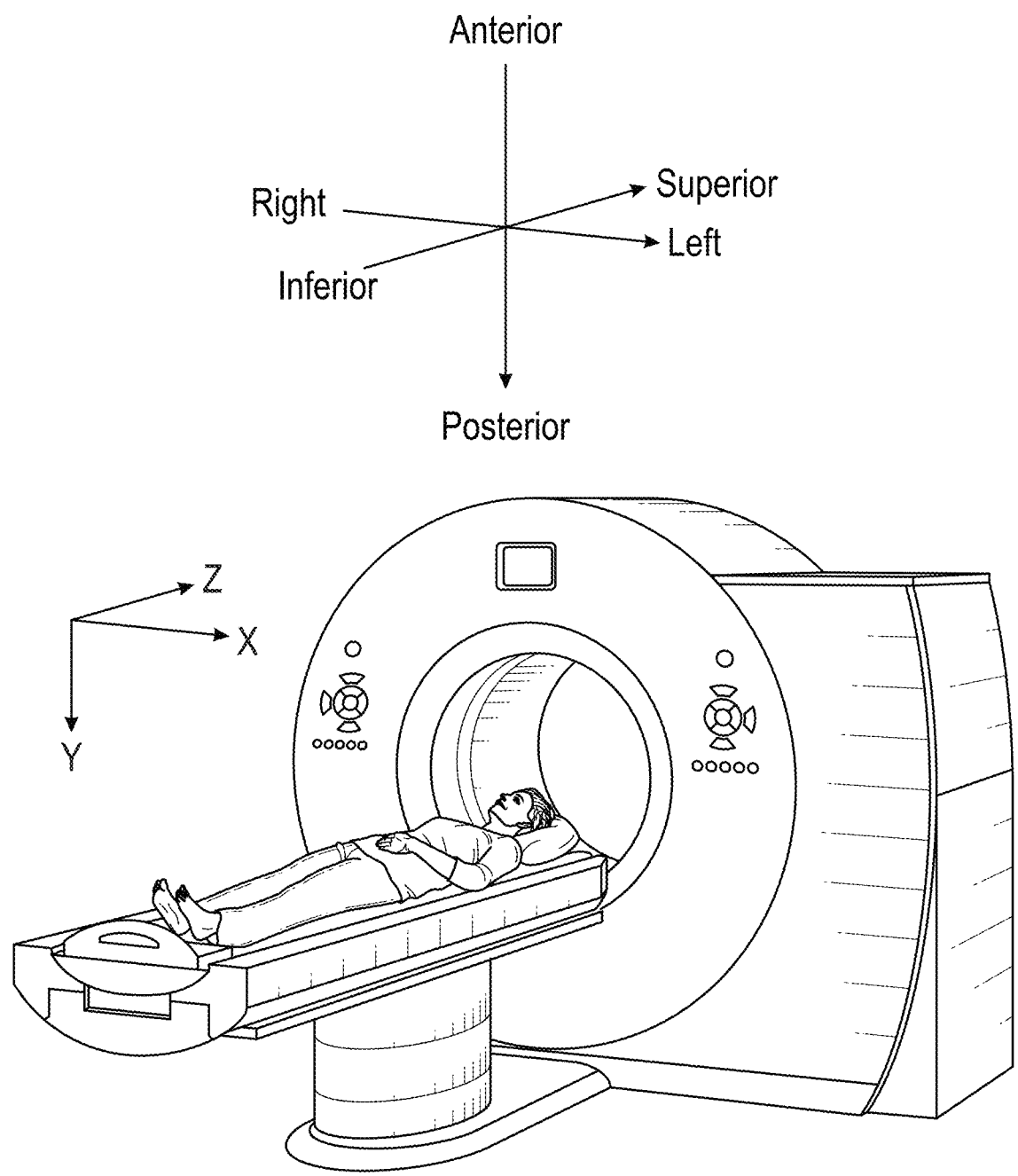
FIG. 1A is a schematic representation of the coordinate directions X, Y, and Z in relation to a human body one or both of whose legs are being imaged, e.g. via magnetic resonance imaging (MRI). The right-left, anterior-posterior, and inferior-superior directions are also shown.
Figure 1B:
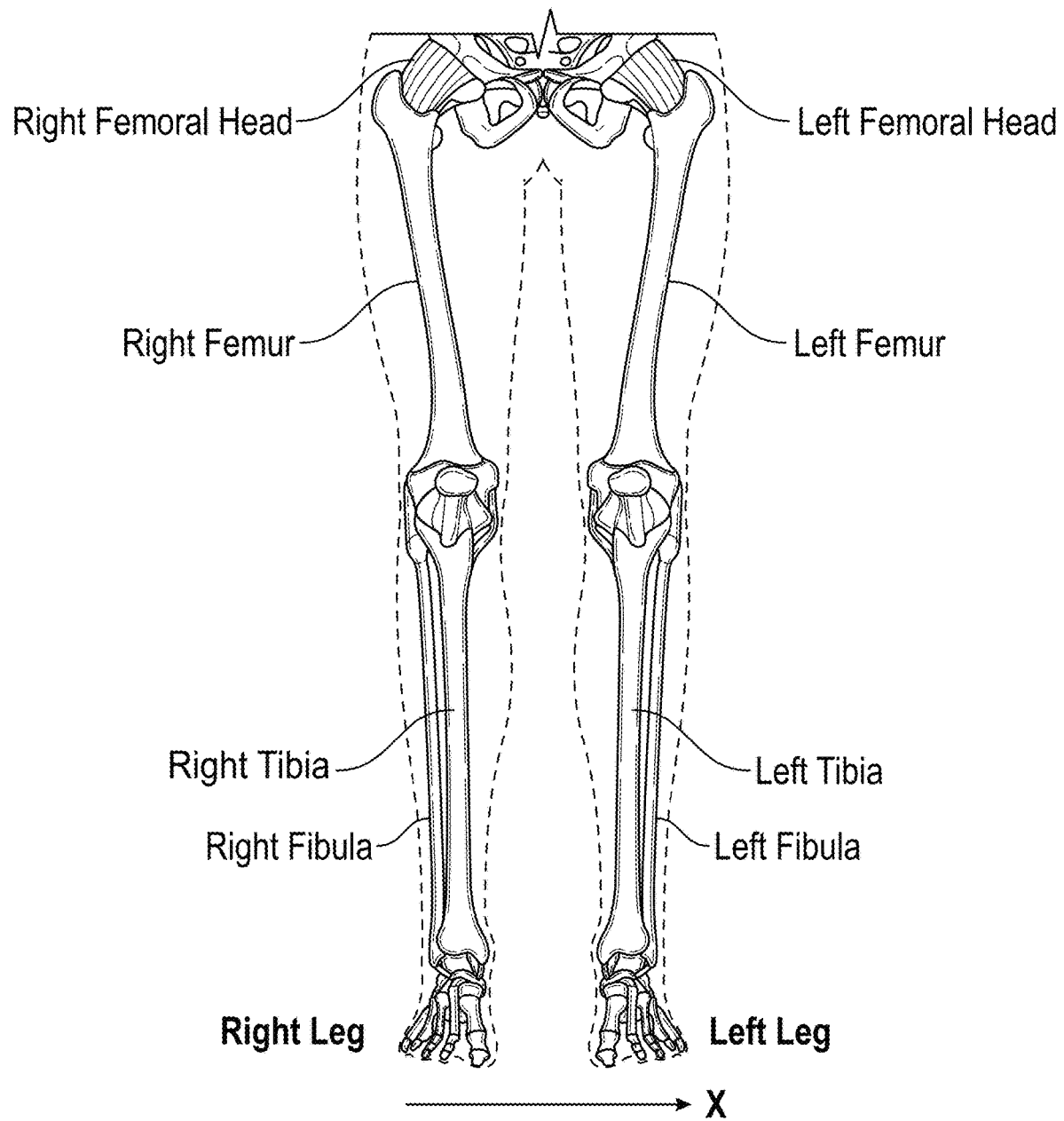
FIG. 1B is one slice of a series of whole leg coronal images, in this case of both right and left legs, only one leg of which will be subject to total knee replacement (TKR) surgery.

Beginning with a whole leg coronal image series (represented schematically in FIGS. 1A and 1B), we can identify whether the series of images are of a right or left leg. This is preferable because, if a technician were to fail to follow the prescribed imaging protocol, scanning of a patient's leg might then be performed in a reverse direction from what is expected, such that the resulting series of image slices may be presented in reverse order. Verification, while not strictly necessary for determining limb alignment angles and cut planes, is still normally performed as a reliability check. If correctly oriented: the X coordinates should increase from left to right; the Y coordinates should increase as one proceeds from anterior (front-most image) to posterior (back-most image); and the Z coordinates should increase from inferior to superior as one proceeds from the ankle region to the knee region and then to the femoral head region at the hip joint.

Figure 2A:
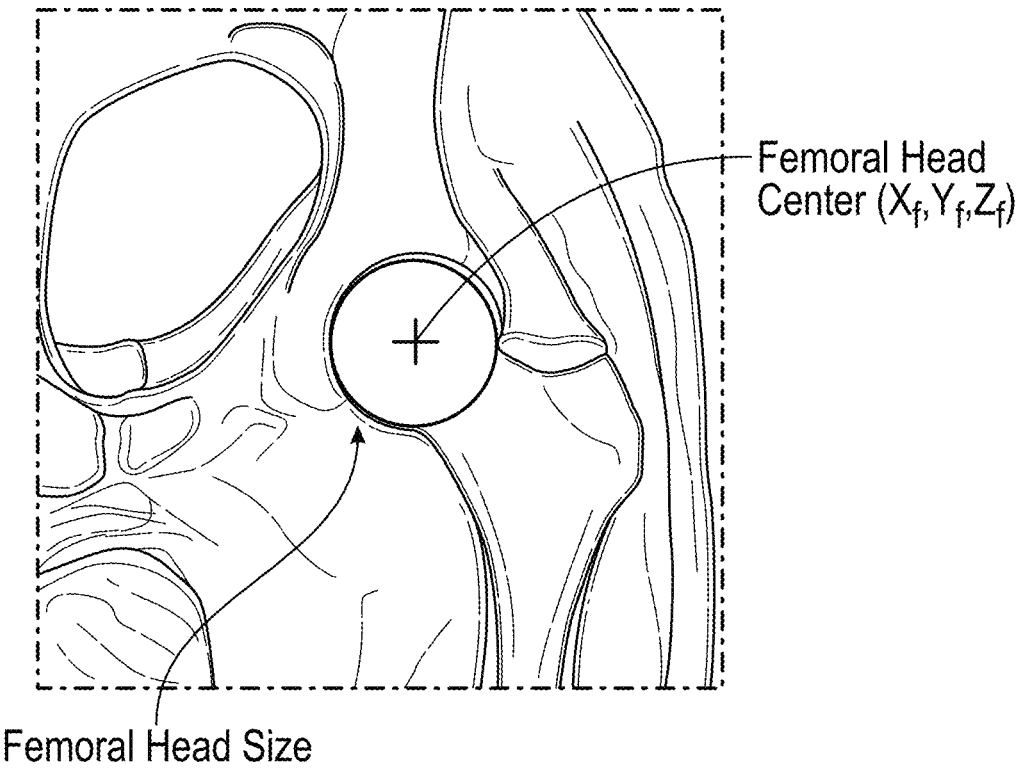
FIG. 2A is a close-up of a femoral head region coronal image slice with identified femoral head.
Figure 2B:
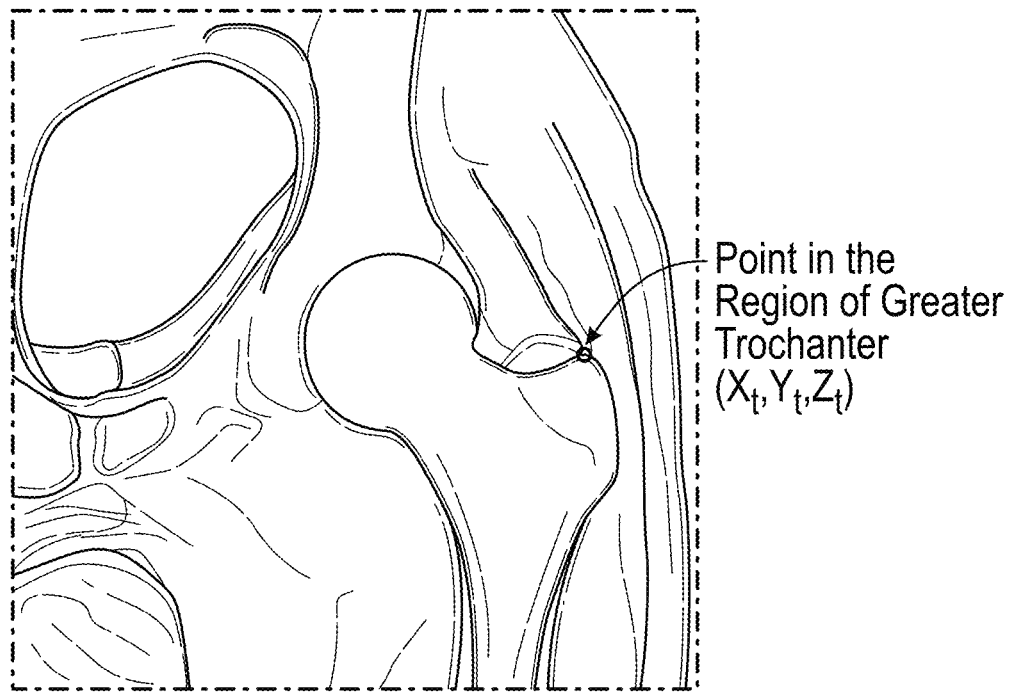
FIG. 2B is a close-up of a femoral head region coronal image slice with identified greater trochanter.
Figure 3A:
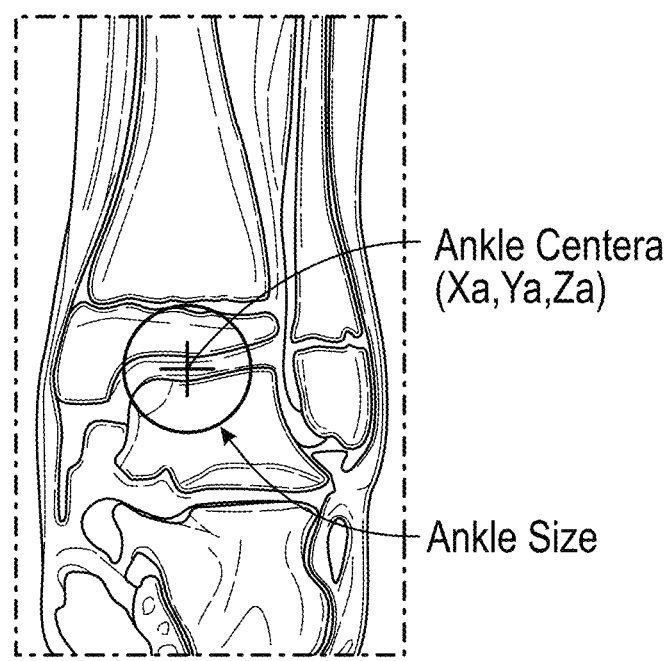
FIG. 3A is a close-up of an ankle region coronal image slice with ankle center tibia-talus interface width.

In the femoral head region (FIG. 2A), find the slice in the image series that contains the largest femoral head size (diameter) and mark the position of femoral head center (Xf, Yf, Zf), and also identify and mark the highest point (Xt, Yt, Zt) of the greater trochanter in the image series (FIG. 2B). If Xf>Xt, the image series is of a RIGHT leg; but if Xf<Xt, the image series is of a LEFT leg. Proceeding to the ankle region (FIG. 3A), one finds the widest tibia and talus interface in the image series and mark the ankle center (Xa, Ya, Za) and ankle size (as a diameter). Here, dimensions are measured based on image pixel coordinates in the series of images.

Figure 3B:
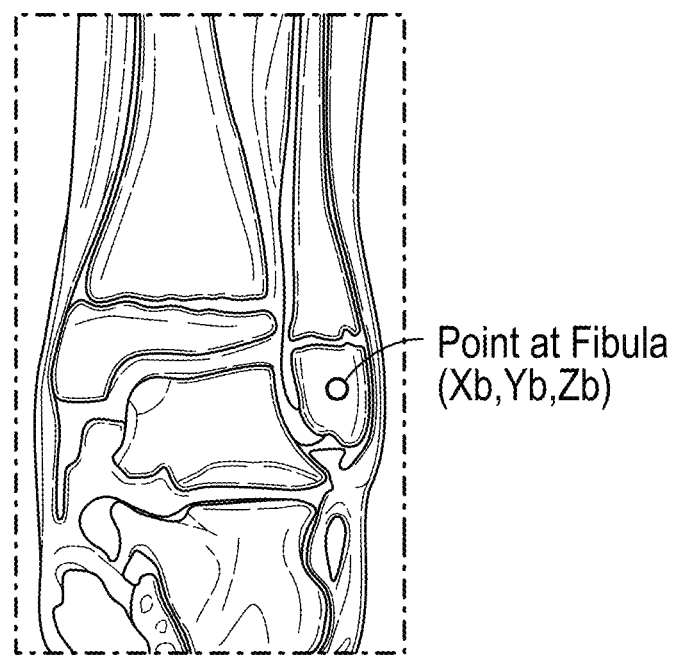
FIG. 3B is a close-up of an ankle region coronal image slice with an identified lower fibula point.

Likewise, one finds the lowest point of the fibula near the ankle in the image series (FIG. 3B) and marks its location (Xb, Yb, Zb). If Xa>Xb, the image series is of a RIGHT leg; but if Xa<Xb, the image series is of a LEFT leg.

Figure 4A:
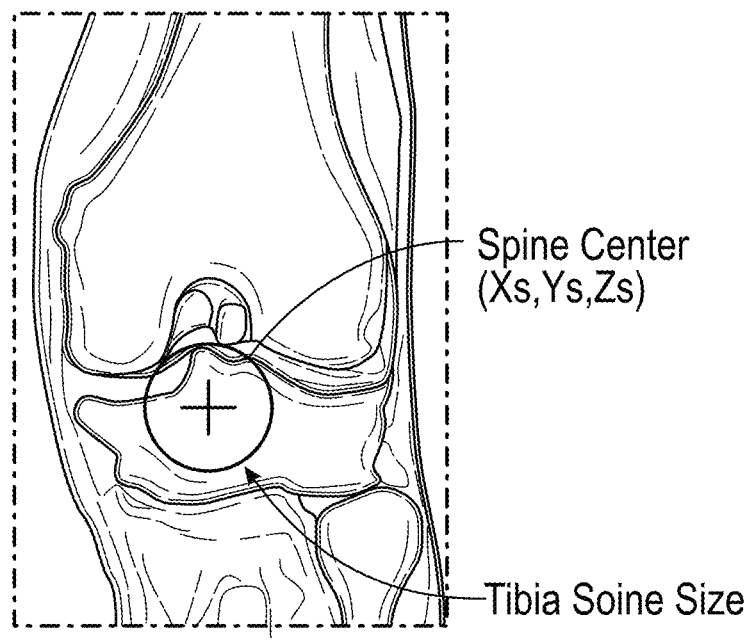
FIG. 4A is a close-up of a knee region coronal image slice with an identified tibia spine (knee joint center).
Figure 4B:
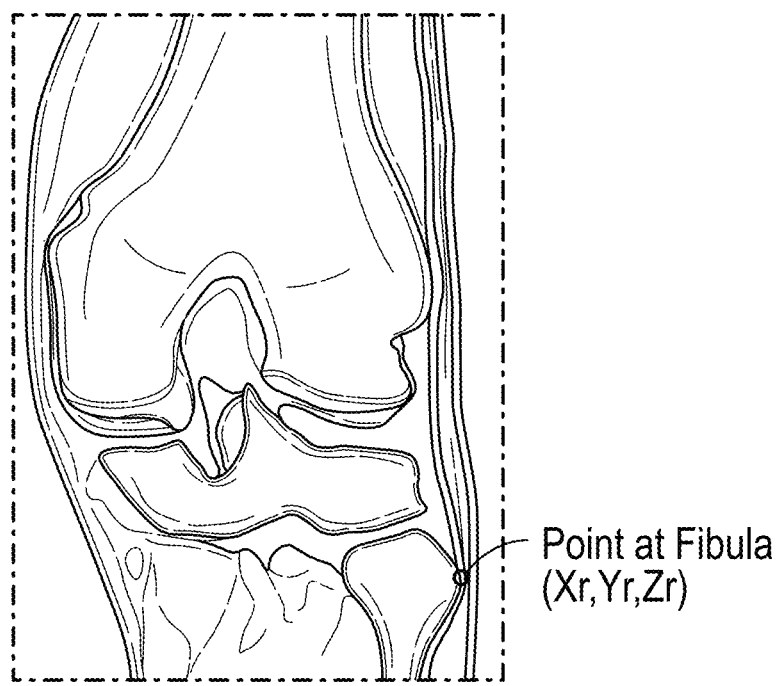
FIG. 4B is a close-up of a knee region coronal image slice with an identified most lateral upper fibula point.
Figure 5:
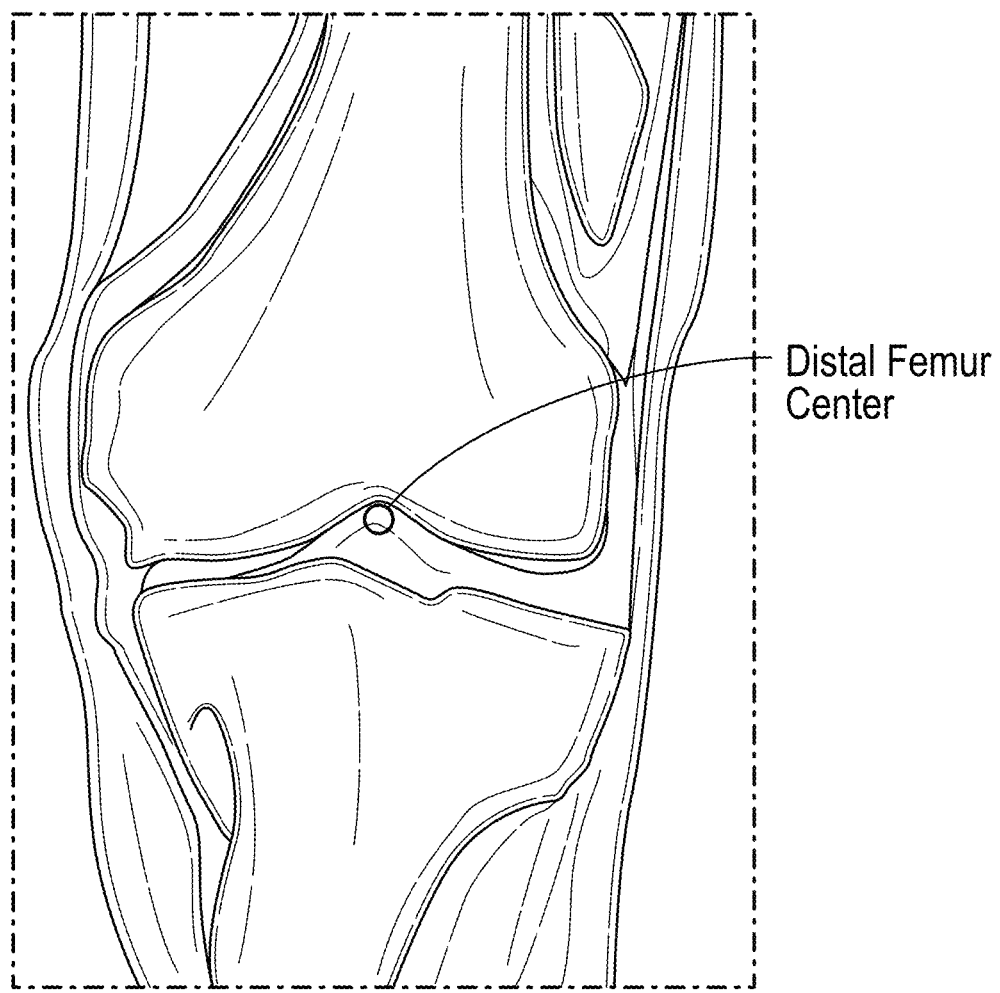
FIG. 5 is a coronal view of a knee image slice containing the distal femur center.

Proceeding finally to the knee region (FIG. 4A), one finds the knee joint center in the image series and mark the location of the tibia spine (Xs, Ys, Zs) and the tibia spine size (as a diameter). We also find the most lateral point of the upper fibula near the knee in the series (FIG. 4B) and mark its location as (Xr, Yr, Zr). Again, if Xs>Xr, the image series is of a RIGHT leg; but, if Xs<Xr, the image series is of a LEFT leg.

All three comparisons (Xf versus Xt, Xa versus Xb, and Xs versus Xr) should obtain identical RIGHT leg or LEFT leg results, thereby verifying that correct leg has been identified. Additionally, when the images are correctly oriented, both Za and Zb should be less than Zs and Zr, which in turn should be less than both Zf and Zt. All of these marked coordinate points are saved in computer memory.

Next, having completed the (optional) leg verification, one proceeds to actual planning of the knee implant dimensioning and alignment. Surgical jigs (that establish the cut planes) and corresponding implants must be correct for each bone (femur and tibia) separately to avoid possibility of inadvertent twisting between of the upper and lower leg when the implants are surgically installed.

Figure 6C:
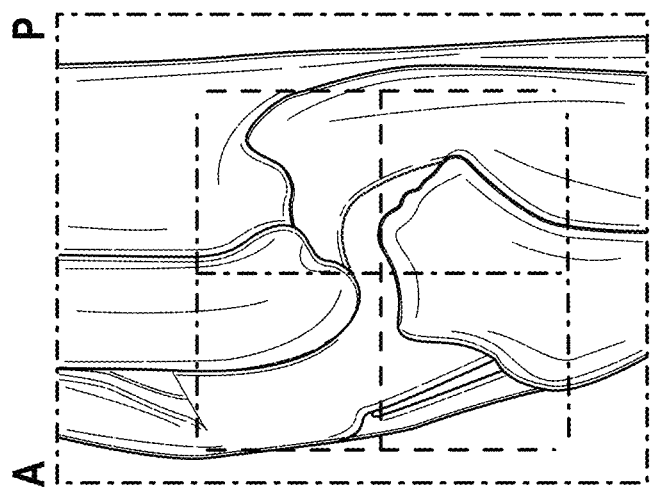
FIGS. 6A-6C are respective coronal, axial and sagittal views of the knee region after rotational transformation onto orthogonal coordinates x, y, and z.
Figure 6B:
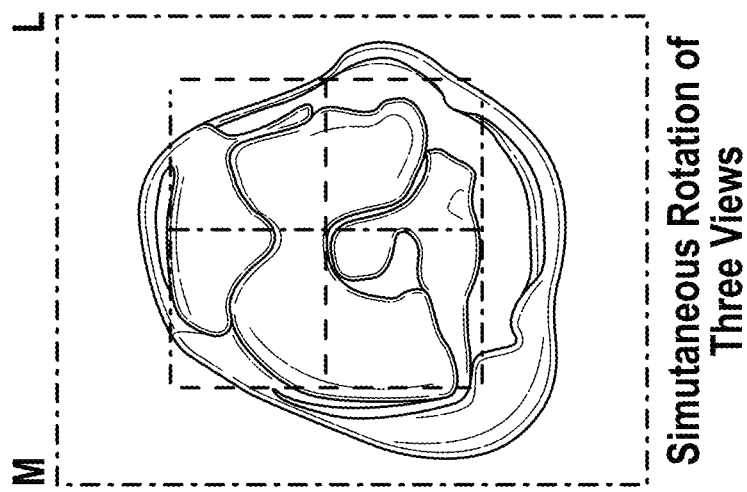
Figure 6A:
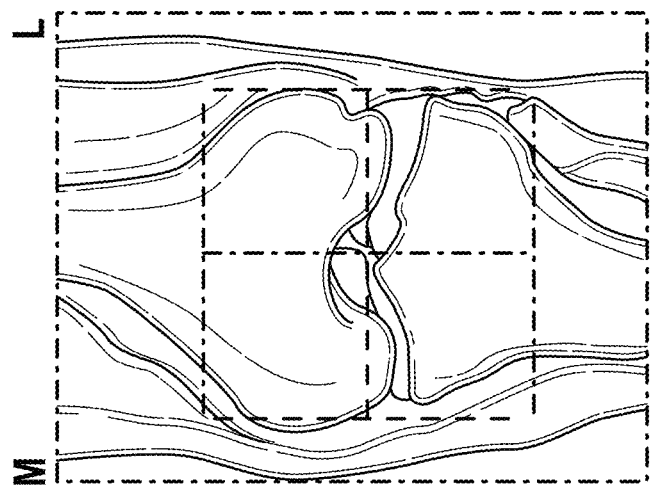
Figure 7:
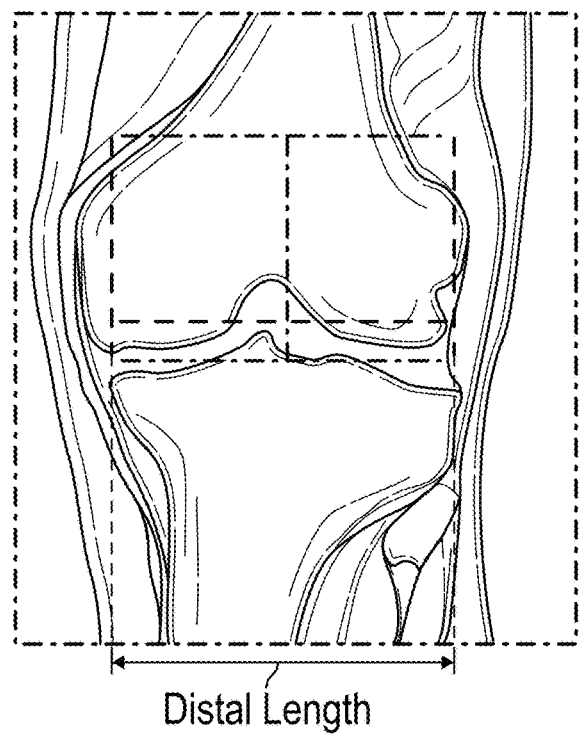
FIGS. 7 and 8 are transformed coronal images of the distal femur region of the knee illustrating measurement of distal femur length and establishing of a distal femur line between medial and lateral distal femur contact points in the image.
Figure 8:
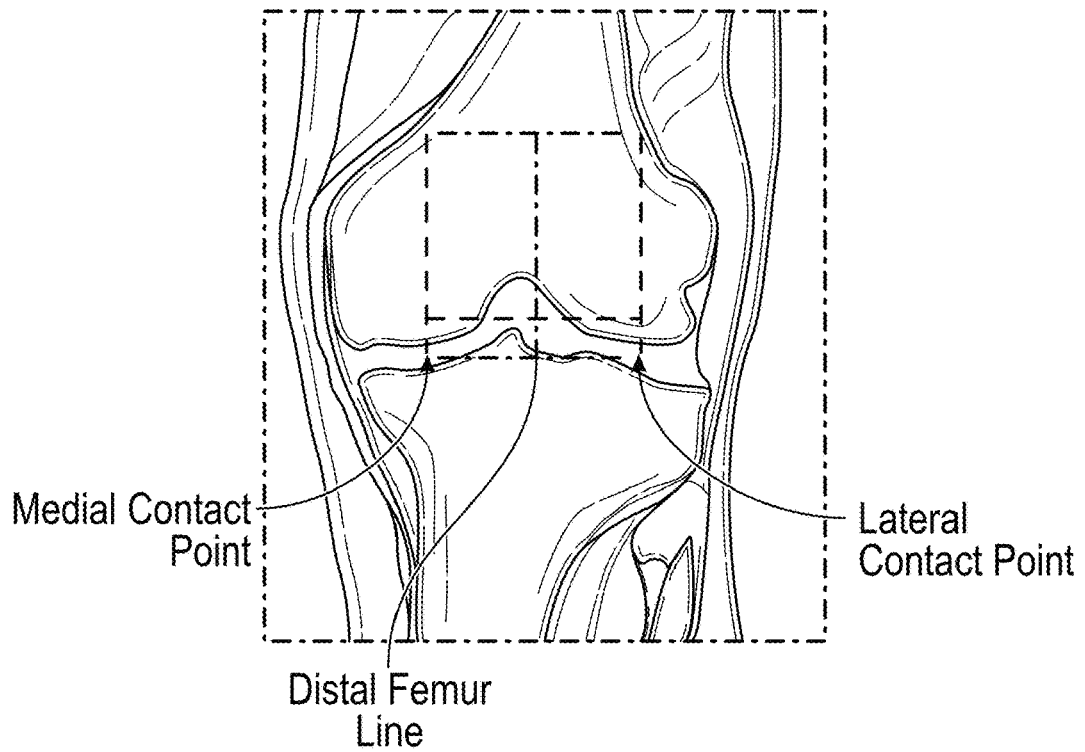
Figure 9:
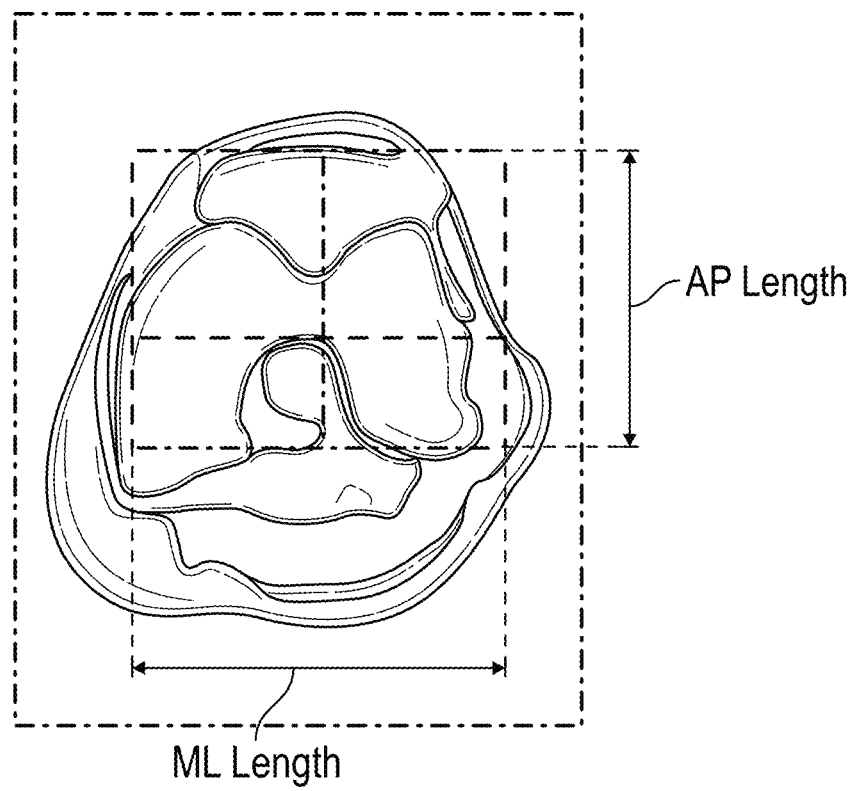
FIG. 9 is a transformed axial image of the distal femur region of the knee illustrating measurement of anterior-posterior (AP) distal femur length and medial-lateral (ML) femur length.
Figure 10:
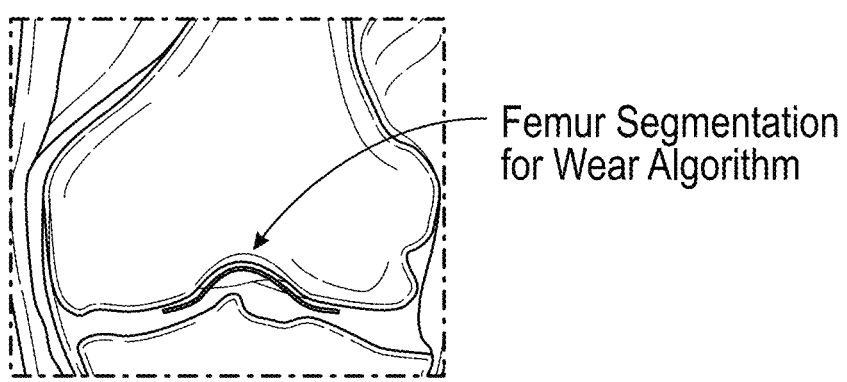
FIG. 10 is a transformed coronal image slice of the distal femur center illustrating definition of the distal femur's surface contour.

We begin by identifying the anatomical rotation center of the femur where the condyles meet. Locating the distal femur center in a coronal view of the knee, we use that point as the origin for a simultaneous three-view rotation of coronal, axial, and sagittal images (FIGS. 6A-6C) onto orthogonal x, y, and z axes for initial setup of the femur/tibia alignment. The transformed orthogonal (x,y,z) coordinates are used from this point forward. Using the transformed coronal image of the distal femur region, identify and mark medial and lateral distal femur contact points (FIG. 7), and define a distal femur line (FIG. 8) in the image between those two contact points, thereby yielding a measure of the medial-lateral (ML) distal femur length. Turning to the transformed axial view (FIG. 9), anterior-posterior (AP) endpoints are likewise marked, which yields a measure of AP distal femur length. Returning to the coronal view (FIG. 10), the image slice containing the distal femur center is used to define the contour of the distal femur surface, as shown. It is this contour (defined as a set of marked coordinates and/or corresponding polynomial equation parameters) that will be employed with curve segmentation and application of a wear algorithm to estimate a pre-arthritic contour for the distal femur surface.

Figure 11:
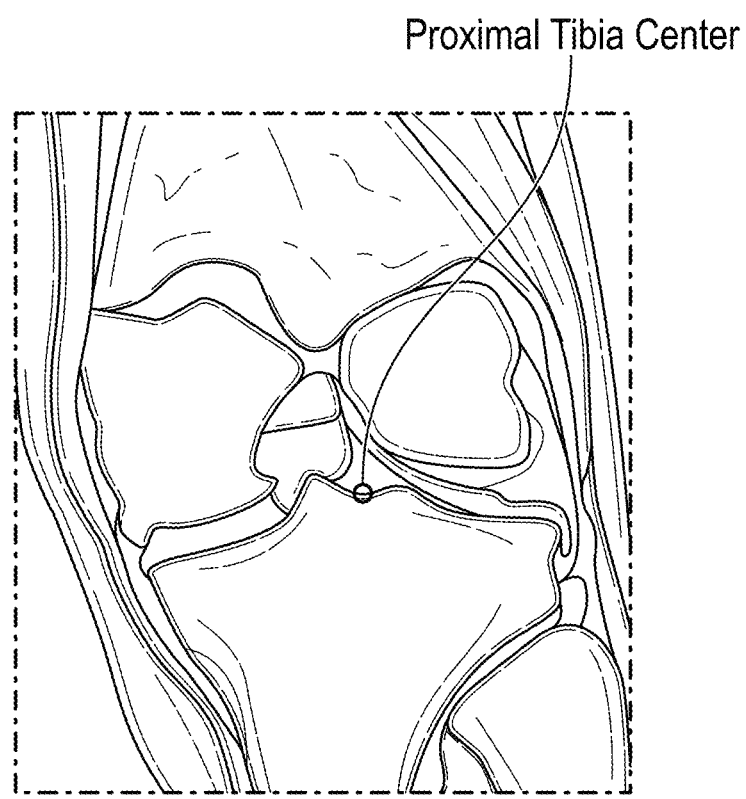
FIG. 11 is a coronal view of a knee image slice containing the proximal tibia center.
Figure 12C:
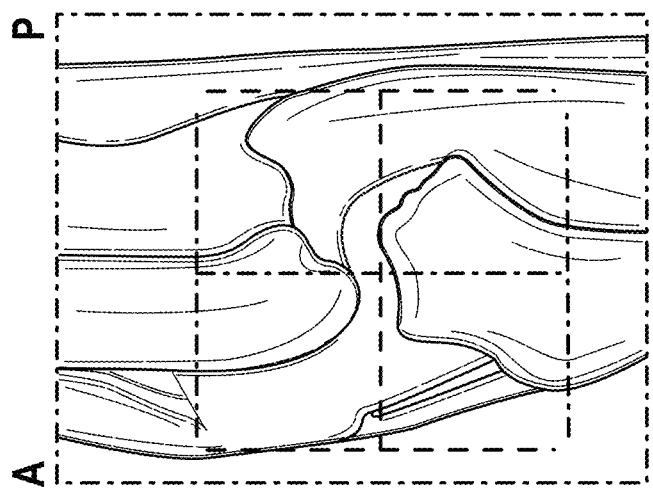
FIGS. 12A-12C are respective coronal, axial and sagittal views of the knee region after rotational transformation onto orthogonal coordinates x, y, and z.
Figure 12B:
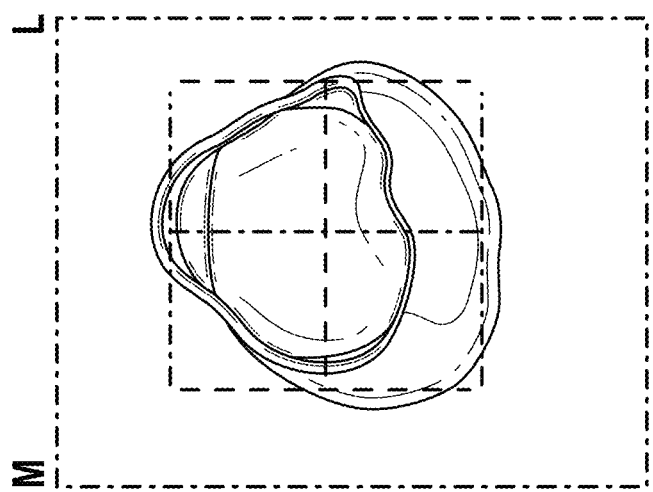
Figure 12A:
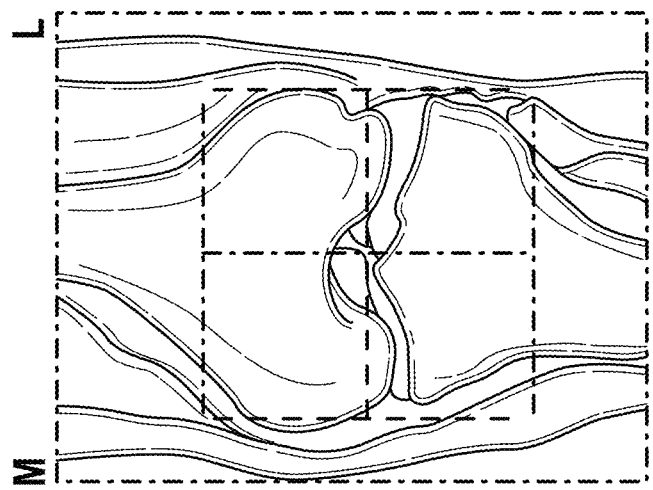
Figure 13:
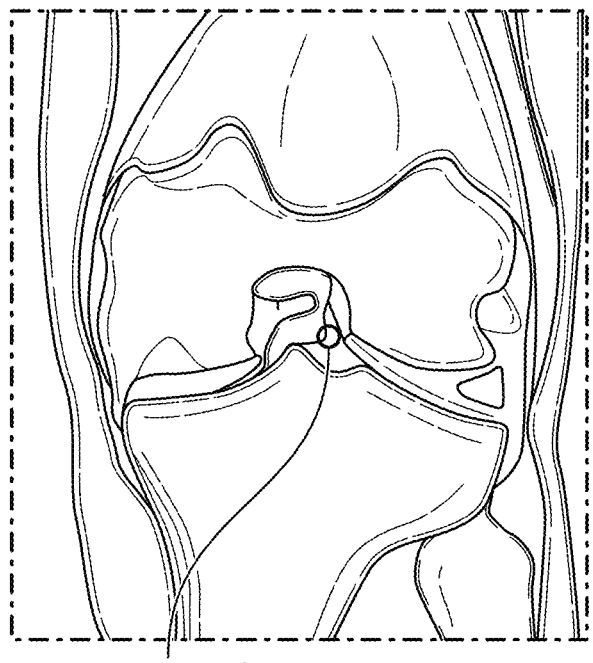
FIGS. 13 and 14 are transformed coronal images of the proximal tibia region of the knee along the proximal tibia center that illustrates establishment of a medial-lateral proximal tibia line.
Figure 14:
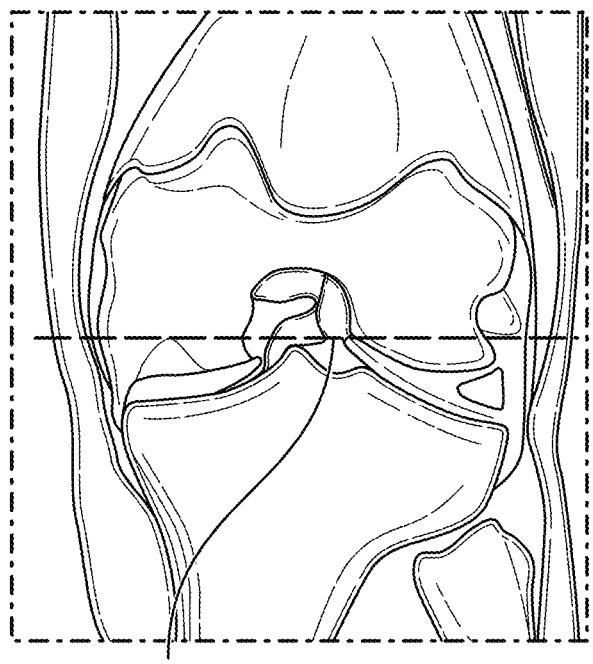
Figure 15:
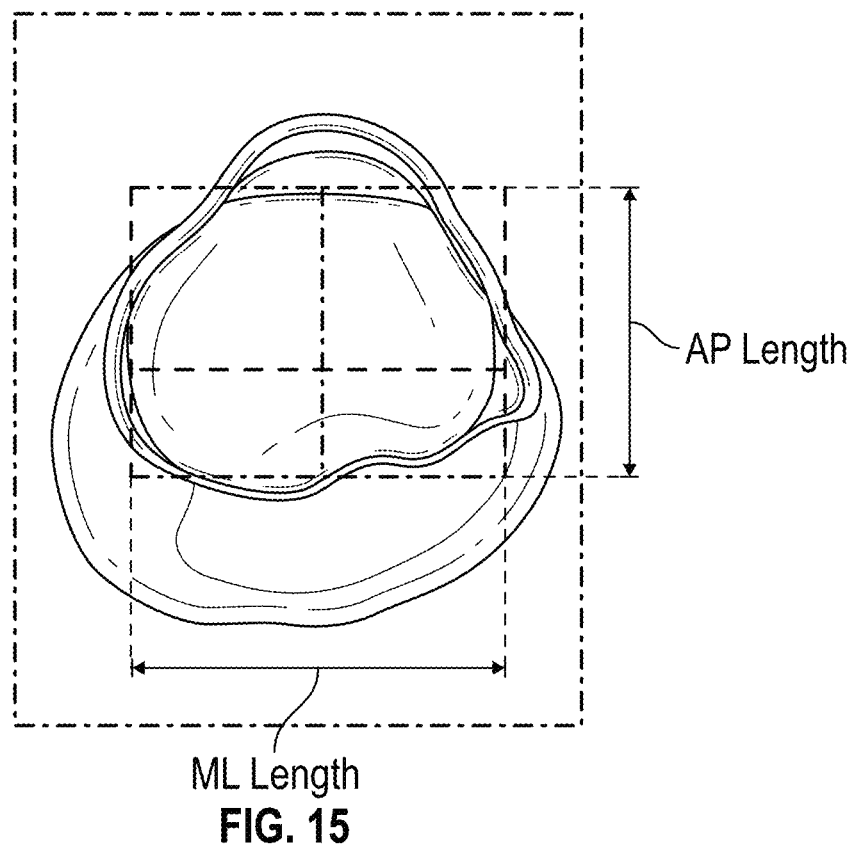
FIG. 15 is a transformed axial image of the proximal tibia region of the knee illustrating the measurement of proximal tibia dimensions (both medial-lateral (ML) and anterior-posterior (AP) lengths) using the image.
Figure 16:
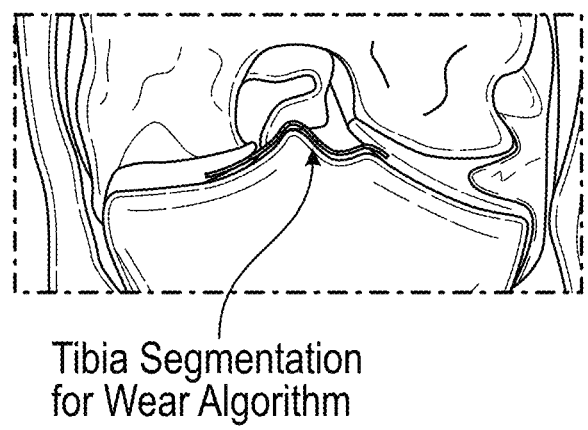
FIG. 16 is a transformed coronal image slice of the proximal tibia center illustrating definition of the proximal tibia's surface contour.

Proceeding to the proximal region of tibia, we locate the proximal tibia center (FIG. 11) and use this center as the origin for a simultaneous three-view rotation of coronal, axial, and sagittal images (FIGS. 12A-12C) onto orthogonal x, y, and z axes. The proximal tibia center is again seen in the transformed coronal view in FIG. 13 and we then define a medial-lateral proximal tibia line (FIG. 14) in a manner substantially similar to that for the distal femur line of FIG. 8. Likewise, using an axial view (FIG. 15) of the anterior end of the tibia located some specified distance (e.g. approximately 11mm) below the established proximal tibial line, establish tibia dimensions (medial-lateral and anterior-posterior lengths). Again, returning to the coronal view, the tibia surface contour is defined, as shown in FIG. 16. As with the femoral contour, the tibial contour definition will be used with curve segmentation and the application of a wear algorithm to estimate a pre-arthritic contour for the proximal tibia surface.

Various biomechanical wear models for joints, including knee joints, have been developed. Tribology (the study of friction, lubrication, and wear) presents several wear mechanisms due to a combination of joint loading (longitudinal or compressive stresses) with rolling and/or sliding motion of joint members (tangential or shear stresses) leading to one or more of: joint surface deformation and fatigue, adhesion and/or cohesion of joint members, frictional contact from damaged joint fragments of bone or cartilage, and abrasive wear or fretting. The resulting wear can be characterized using physical parameters of the articular surface joint (ASJ) structure, such as longitudinal (compression) stress modulus $E_0$ and tangential (shear) stress modulus $G_0$, analysis of images of the existing joint element shapes to obtain wear vectors $w(\varphi)$ associated with orientations along the ASJ structure, and application of wear coefficients or parameters from a chosen wear model (e.g. the Reye-Archard-Khrushchov wear law, wherein the total volume of material removed due to wear is proportional to the work done by friction forces). Any suitable wear model for the knee may be chosen, including various finite element computational models.

In FIG. 16, the joint contour may be represented as a collection of two-dimensional curves, $\chi(x,y)=0$ in the image slice planes. Portions of each curve $\chi$ may be approximated by numerical analysis as triplets points $(x_{m-1},y_{m-1})$, $(x_m,y_m)$, $(x_{m+1},y_{m+1})$, each of which in turn can be characterized as portions of a parabola, $y=p(x)$, defined by coefficients $\{a_0, a_1, a_2\}$ of a quadratic polynomial $y=p(x)=a_0+a_1x+a_2x^2$. However, the curves $y=p(x)$ are defined for ease of calculation, wear vectors $w(\varphi)$ are associated with each point along the curves based on the orientation of the curve at that point. Both a normal component of wear due to longitudinal stresses at each point and a tangential component of wear due to shear stresses at each point can be determined. Femur and tibia cut planes, $P_f$ and $P_t$, can be independently modified to identify minimum wear orientations for each cut plane. The wear analysis and recommended cut plane orientations can be made available to the orthopedic surgeon to see whether that proposed planes are suitable from a surgical perspective or some corrections (within defined limits) are needed.

Estimation of Optimal Offset Angle

The method provides an estimate of an angle correction, associated with a two-dimensional curve representing an ASJ structure in a Magnetic Resonance Image (MRI) or Computer Axial Tomography (CT) image. The correction should be introduced to balance expected wear and/or combined gravitational forces on that ASJ structure.

Figure 17:
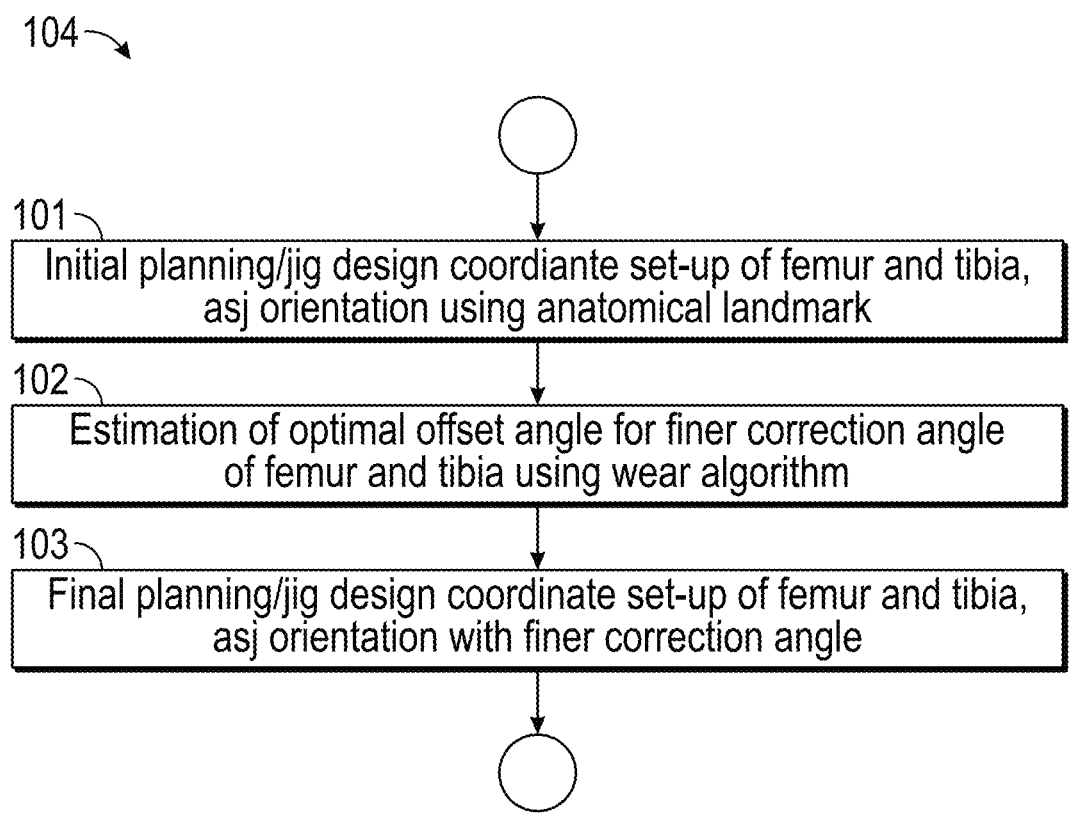
FIG. 17 illustrates the flow chart of the overall procedure of the estimation of optimal offset angle.

FIG. 17 illustrates a flowchart 104 to establish a planning/jig coordinate system. A first step 101 of this procedure is to manually or automatically orient coronal, axial and sagittal images of the ASJ structure using knee anatomical features or landmarks, such as distal reference line, posterior reference line, tibial plateau reference line, etc., leading to the initial planning/template design coordinate system. Due to arthritis damage on knee joint, the precise alignment is seldom achieved in the first step 101. The second step 102 is introduced for finer adjustment of the coordinate system using wear algorithms. The final step 103 orients the images of ASJ structure by the optimal offset angle achieved in the second step 102.

Furthermore, due to arthritic damages of femur tibia, the planning/template design coordinate system for femur and tibia is analyzed separately, and the femur and tibia coordinate systems are combined.

Figure 18A:
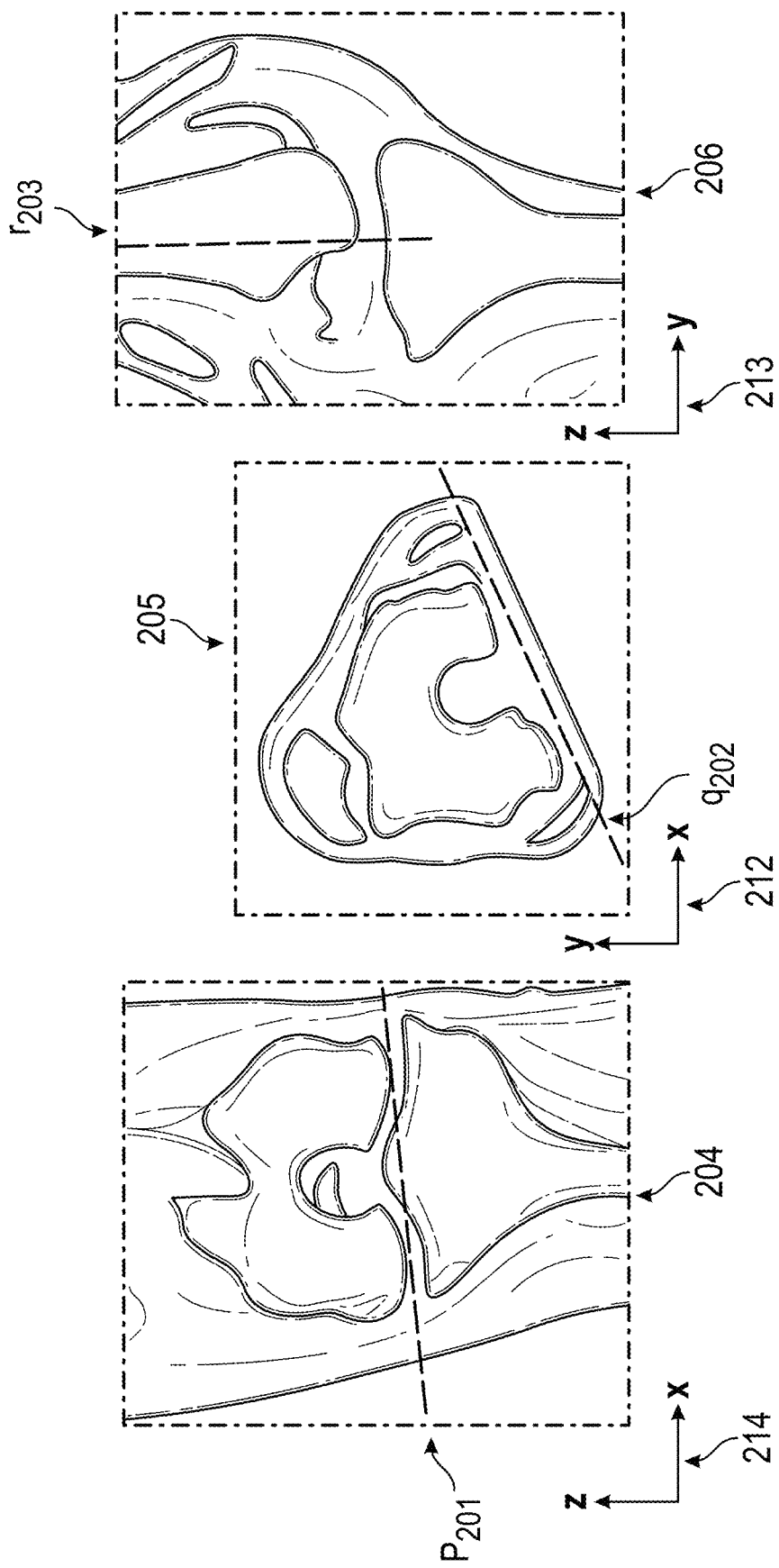
FIGS. 18A and 18B illustrate three orthogonal projections of a single line segment LS, representing an ASJ component, onto an xz-plane, a yz-plane, and an xy-plane.
Figure 18B:
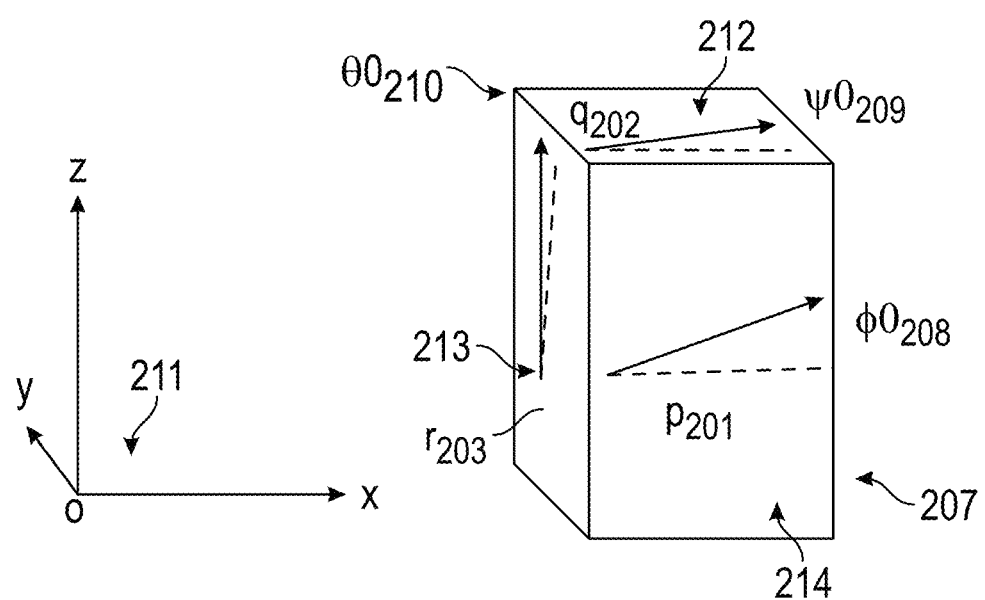

FIGS. 18A and 18B illustrate three orthogonal projection vectors, p 201, q 202 and r 203, of a line segment LS, representing an ASJ component 207 in the original image coordinate system 211, onto an xz-plane 214, a yz-plane 213 and an xy-plane 212, respectively, and representing a projection of LS onto the xz, -yz- and xy-planes. The line segment LS is associated with a component of an articular surface joint ("ASJ") structure of interest and these projections may be oriented at arbitrary angles, $\varphi 0$ 208, $\psi 209$ and $\theta 210$ relative to the x-axis, the y-axis and the z-axis, respectively. The angles, $\varphi 0$, $\psi 0$ and $\theta 0$, and the projection vector lengths, |p|, |q| and |r| are known or measurable, and the projection vector lengths may be equal but are generally not equal.

The vector p 201 is a distal reference line of the coronal image approximately representing the coronal femur slice 204. The vector q 202 is a posterior reference line of the axial image approximately representing axial femur slice 205. The r 203 is a femur shaft line of the sagittal image approximately representing sagittal femur slice 206. As shown in MRI overall voxel diagram 207, the angles made by these vectors with the relevant x-, y- and z-coordinate axes 210 are independent so that the vector lengths, |P|, |q|, and |r|, are not necessarily equal, and as yet have no relationships to each other. Unit length vectors, p0, q0 and r0, are formed as in Eqs. (1-1), (1-2) and (1-3).

The projection vectors p, q and r have true lengths L1=|p|, L2=|q| and L3=|r|, respectively, and for notational convenience, normalized vectors $$p0=p/|p|=i_x \sin\varphi 0+i_z \cos\varphi 0 \qquad (1\text{-}1)$$

$$q0=q/|q|=i_y \cos\psi 0+i_z \sin\psi 0 \qquad (1\text{-}2)$$

$$r0=r/|r|=i_x \cos\theta 0+i_y \sin\theta 0 \qquad (1\text{-}3)$$

are used here. The angles $\varphi 0$, $\psi 0$ and/or $\theta 0$ may be measured directly. Alternatively, these angles may be determined from ratios of components of vector cross products, such as $$(p0\hat{\,}q0)_z/(p0\hat{\,}q0)_y=\cot\psi 0 \qquad (2\text{-}1)$$

$$(p0\hat{\,}q0)_z/(p0\hat{\,}q0)_x=\tan\varphi 0 \qquad (2\text{-}2)$$

$$(q0\hat{\,}r0)_z/(q0\hat{\,}r0)_y=\cot\psi 0 \qquad (2\text{-}3)$$

$$(q0\hat{\,}r0)_x/(q0\hat{\,}r0)_y=\tan\theta 0 \qquad (2\text{-}4)$$

$$(r0\hat{\,}p0)_x/(r0\hat{\,}p0)_y=-\tan\theta 0 \qquad (2\text{-}5)$$

$$(r0\hat{\,}p0)_z/(p0\hat{\,}p0)_x=-\tan\varphi 0 \qquad (2\text{-}6)$$

Other ratios of components of vector cross products, $(p0\hat{\,}q0)$, $(q0\hat{\,}r0)$ and $(r0\hat{\,}p0)$, can also be used here to determine or estimate the angles and angle signums.

The projection vectors p0, q0 and r0 are rotated by an ordered sequence of orthogonal transformations, $R_y(\varphi_n)$, $R_x(\psi_n)$ and $R_z(\theta_n)$ (n=1, 2, ...), where the individual angles $\varphi_n$, $\psi_n$, and $\theta_n$, are chosen so that the resulting transformed vectors lie in specified xz-, yz- and xy-planes. The scalar products, p.q, q.r and r.p, of the transformed projection vectors are invariant under the orthogonal transformations, but relationships of these transformed projection vectors to each other and to the coordinate axes can be improved by this procedure. The procedure is terminated when certain threshold conditions are satisfied. The end products of the resulting multiply-transformed projection vectors are used to determine adjustments to angular orientation of a cut plane to be used to replace part or all of an ASJ structure.

A second step determines a final optimal offset angle (correction angle) of the planning/jig design coordinate for finer adjustments of alignment in order to compensate for arthritis damages that are not addressed by the first step of alignment procedures. The ASJ structure is represented as a two-dimensional curve, $\chi(x,y)=0$ lying in a plane $\Pi$, which is approximated by a finite collection of spaced apart points with location coordinates $(x_m, y_m)$, based on one or more MRI images or CT images ("slices") of the ASJ structure of interest. A "wear vector" $w(\phi)$ for a temporarily fixed orientation angle $\phi$ is computed for consecutive sequences of the locations $\{(x_m, y_m)\}_m$, for which sequences overlap at the sequence ends. For each partial curve $\chi(x,y)_p$, consisting of a curvilinear segment of the curve $\chi(x,y)=0$ that extends between a first location $(x_{m1}, y_{m1})$ and a second location $(x_{m2}, y_{m2})$, the wear variable $w(\phi)$ is estimated for that segment. The contributions to a numerical wear vector $w(\phi)$ from all of the segments corresponding to a selected orientation angle ($\phi$) (fixed), are estimated, and a (net) wear value is minimized with respect to choice of the orientation angle ($\phi$), It is anticipated that the minimum wear angle value $\phi$(min), corresponding to minimum wear value w(min), will be no more than a few degrees, for a given MRI slice or CT slice, and that this minimum wear value will vary slowly, if at all, from one slice to an adjacent slice.

An arithmetical average or other statistical average of the minimum wear angle $\phi$(min) can be estimated for a collection of curves $\chi(x,y)=0$ and/or slices. Optionally, this average value $\phi$(avg; min) can be taken to approximately represent an optimum angle adjustment for an entire collection of the corresponding ASJ structure slices.

The wear vector can be estimated and minimized numerically by: (1) representing an ASJ structure curve $\chi(x,y)=0$ as a sequence of two dimensional polynomials representing different segments of the curve; and (2) associating a wear parameter $w(\phi)$ with a projection of a numerically estimated virtual force (e.g., gravitational effects), oriented at a fixed angle ($\phi$), computed at each of a sequence of spaced apart locations $(x_m, y_m)$ on the curve $\chi(x,y)=0$. This numerical sum is minimized with respect to the choice of a numerical value for the wear angle $\phi$. Computation of a wear vector is performed in two dimensions, yielding a vector sum.

A first orthogonal transformation, $R_1=R_y(\phi 1)$, $$R_y(\phi 1) = \begin{bmatrix} \cos\phi 1 & 0 & \sin\phi 1 \\ 0 & 1 & 0 \\ -\sin\phi 1 & 0 & \cos\phi 1 \end{bmatrix}, \quad (3)$$

representing a rotation about the initial y-axis, is applied to each of the projection vectors p0, q0 and r0 to produce first stage projection vectors, $$p1=R_y(\varphi 1), p0=[\sin(\varphi 0+\varphi 1), 0, \cos(\varphi 0+\varphi 1)]^{tr}, \quad (4\text{-}1)$$

$$q1=R_y(\varphi 1), q0=[\sin^*\psi 0\ \sin\varphi 1, \cos\psi 0, \sin^*\psi 0\ \cos\varphi 1]^{tr}, \quad (4\text{-}2)$$

$$r1=R_y(\varphi 1), r0=[\cos\theta 0\ \cos\varphi 1, \sin\theta 0, -\cos\theta 0\ \sin\varphi]^{tr}, \quad (4\text{-}3)$$

where the rotation angle $\varphi 1$ is to be determined so that the rotated projection vector p1 lies as close as possible to a selected coordinate axis, here the x-axis $[\pm 1, 0, 0]^{tr}$ or the z-axis $[0, 0, \pm 1]^{tr}$. The first choice corresponds to $\varphi 0+\varphi 1=\pi/2$ or $\varphi 0+\varphi 1=3\pi/2$, with $p1=[\pm 1, 0\ 0]^{tr}$; the second choice corresponds to $\varphi 0+\varphi 1=0$ or $\varphi 0+\varphi 1=\pi$ with $p1=[0,0,\pm 1]^{tr}$. If, for example, the x-axis is chosen, the optimum angle choice for the first stage is $\varphi 0+\varphi 1=\pi/2$ or $\varphi 0+\varphi 1=3\pi/2$, with $p1=[\pm 1,0,0]$. An optimized first transformation stage produces a 3×3 matrix with components [p1, q1, r1] with $p1=[\pm 1, 0, 0]^{tr}$. The orthogonal transformation $R_y(\varphi 1)$, with $\varphi 1$ equal to its optimal value (for example $\varphi 0+\varphi 1=\pi/2$ or $3\pi/2$), is applied to produce the first stage projection vectors, p1, q1 and r1, set forth in Eqs. (4-1), (4-2) and (4-3).

A second orthogonal transformation, $$R_2 = R_x(\psi 1) = \begin{bmatrix} 1 & 0 & 0 \\ 0 & \cos\psi 1 & -\sin\psi 1 \\ 0 & \sin\psi 1 & \cos\psi 1 \end{bmatrix}, \quad (5)$$

representing a rotation around a second rotation axis (x-axis), is applied to each of the projection vectors p1, q1 and r1 to produce second stage projection vectors, $$p2=R_x(\psi 1)\ p1=[0,-\sin\psi 1,\cos\psi 1]^{tr}, \quad (6\text{-}1)$$

$$q2=R_x(\psi 1), q1=[\sin\psi 0\ \sin\phi 1, \cos\psi 0\ \cos\psi 1-\sin\psi 0\ \cos\phi 1\ \sin\psi 1,\ \cos\psi 0\ \sin\psi 1-\sin\psi 0\ \cos\phi 1\ \cos\psi 1]^{tr}, \quad (6\text{-}2)$$

$$r2=R_x(\psi 1), r1=[\cos\psi 0\ \cos\phi 1, \sin\theta 0\ \cos\psi 1+\cos\theta 0\ \sin\phi 1\ \sin\psi 1,\ \sin\theta 0\ \sin\psi 1-\cos\theta 0\ \sin\phi 1\ \cos\psi 1]^{tr}. \quad (6\text{-}3)$$

Here the rotation angle $\psi 1$ is to be determined so that the rotated projection vector q2 lies in the xy-plane:

$$(q2)_z=\cos\psi 0\ \sin\psi 1-\sin\psi 0\ \cos\phi 1\ \cos\psi 1=0, \quad (7)$$

where the only variable in this relation is the angle $\psi 1$.

For this second stage (n=2), Eq. (7) is rewritten as $$(q_2)_z = A_2\sin\psi 1 + B_2\cos\psi 1 + C_2 \quad (8)$$

$$= [A_2^2 + B_2^2]^{1/2}\sin[\psi 1 + \alpha 2] + C_2 = 0,$$

$$A_2=\cos\psi 0, \quad (9\text{-}1)$$

$$B_2=-\sin\psi 0\ \cos\phi 1, \quad (9\text{-}2)$$

$$C_2=0 \quad (9\text{-}3)$$

$$\alpha 2=\tan^{-1}(B_2/A_2)=-\tan^{-1}[\sin\psi 0\ \cos\phi 1/\cos\psi 0]. \quad (9\text{-}4)$$

For Eq. (9) (with C=0), an optimum solution for this second stage is $$\psi 1+\alpha 2=0 \text{ or } \pi. \quad (10)$$

A third orthogonal transformation, $$R_3 = R_z(\theta 1) = \begin{bmatrix} \cos\theta 1 & -\sin\theta 1 & 0 \\ \sin\theta 1 & \cos\theta 1 & 0 \\ 0 & 0 & 1 \end{bmatrix}, \quad (11)$$

representing a rotation around a third rotation axis (z-axis), is applied to each of the projection vectors p2, q2 and r2 to produce third stage projection vectors, $$p3=R_z(\theta 1)\ p2=[0,-\sin\psi 1\ \sin\theta 1,-\cos\psi 1\ \cos\theta 0]^{tr}, \quad (12\text{-}1)$$

$$q3=R_z(\theta 1)\ q2=[\sin\psi 0\ \sin\phi 1\ \cos\theta 1-(\cos\psi 0\ \cos\psi 1-\sin\psi 0\ \cos\phi 1\ \sin\psi 1\ \sin\theta 1, \sin\psi 0\ \sin\phi 1\ \sin\theta 1+(\cos\psi 0\ \cos\psi 1-\sin\psi 0\ \cos\phi 1\ \sin\psi 1)\ \cos\theta 1, \cos\psi 0\ \sin\psi 1-\sin\psi 0\ \cos\phi 1\ \cos\psi 1]^{tr} \quad (12\text{-}2)$$

$$r3=R_z(\theta 1)\ r2=[\cos\theta 0\ \cos\phi 1\ \cos\theta 1-(\sin\theta 0\ \cos\psi 1-\cos\theta 0\ \sin\psi 0\ \sin\psi 1)\sin\theta 1, \cos\theta 0\ \cos\phi 1\ \sin\theta 1-(\sin\theta 0\ \cos\psi 1-\cos\theta 0\ \sin\phi 1\ \sin\psi 1)\cos\theta 1, \sin\theta 0\ \sin\psi 1-\cos\theta 0\ \sin\phi 1\ \cos\psi 1]^{tr}. \quad (12\text{-}3)$$

The rotation angle $\theta 1$ is to be determined so that the rotated projection vector r3 lies in the xz-plane:

$$(r3)_y = A_3\sin\theta 1 + B_3\cos\theta 1 + C_3 = 0 \quad (13)$$

$$= [A_3^2 + B_3^2]^{1/2}\sin[\theta 1 + \alpha 3] + C_3 = 0,$$

$$A3 = \cos\theta 0 \cos\phi 1, \quad (14\text{-}1)$$

$$B_3 = -(\sin\theta 0 \cos\psi 1 - \cos\theta 0 \sin\phi 1 \sin\psi 1), \quad (14\text{-}2)$$

$$C_3 = 0, \quad (14\text{-}3)$$

$$\alpha 3 = \tan^{-1}(B_3/A_3), \quad (14\text{-}4)$$

$$\theta 1 + \alpha 3 = 0 \text{ or } \pi. \quad (15)$$

A fourth orthogonal transformation $$R_y(\varphi 2) = \begin{bmatrix} \cos\phi 1 & 0 & \sin\phi 1 \\ 0 & 1 & 0 \\ -\sin\phi 1 & 0 & \cos\phi 1 \end{bmatrix}, \quad (16)$$

representing a rotation around a fourth rotation axis (y-axis), is applied to each of the projection vectors p3, q3 and r3 to produce fourth stage projection vectors, $$p4 = R_y(\phi 2)\, p3 = [\cos\psi 1 \cos\theta 1 \sin\phi 2, -\sin\psi 1 \sin\theta 1, \cos\psi 1 \cos\theta 1 \cos\phi 2]^T, \quad (17\text{-}1)$$

$$q4 = R_y(\phi 2)\, q3 = [\{\sin\theta 0 \sin\phi 1 \cos\theta 1 - (\cos\psi 0 \cos\psi 1 - \sin\psi 0 \cos\phi 1 \sin\psi 1)\sin\theta 1\}\cos\phi 2\} + \{\cos\psi 0 \sin\psi 1 - \sin\psi 0 \cos\phi 1 \cos\psi 1\}\sin\theta 2, \{\sin\psi 0 \sin\phi 1 \sin\theta 1 + (\cos\psi 0 \cos\psi 1 - \sin\psi 0 \cos\phi 1 \sin\psi 1)\cos\theta 1\}, -\{\sin\psi 0 \quad \sin\phi 1 \quad \cos\theta 1 - (\cos\psi 0 \cos\psi 1 - \sin\psi 0 \cos\phi 1 \sin\psi 1)\sin\theta 2 + \{\cos\psi 0 \sin\psi 1 - \sin\psi 0 \cos\phi 1 \cos\psi 1\}\cos\phi 2]^T, \quad (17\text{-}2)$$

$$r4 = R_y(\phi 2)\, r3 = \{\cos\theta 0 \cos\phi 1 \cos\theta 1 - (\sin\theta 0 \cos\psi 1 - \cos\theta 0 \sin\phi 1 \sin\psi 1)\}\cos\phi 2 + \{\sin\theta 0 \sin\psi 1 - \cos\theta 0 \sin\phi 1 \cos\psi 1\}\sin\phi 2, \{\cos\theta 0 \cos\phi 1 \sin\theta 1 - (\sin\theta 0 \cos\psi 1 - \cos\theta 0 \sin\phi 1 \sin\psi 1)\cos\theta 1\}, -\{\cos\theta 0 \cos\phi 1 - (\sin\theta 0 \cos\psi 1 - \cos\theta 0 \sin\phi 1 \sin\psi 1)\sin\theta 1\}\sin\phi 2 + \{\sin\theta 0 \sin\psi 1 - \cos\theta 0 \sin\phi 1 \cos\psi 1\}\cos\phi 2]^T. \quad (17\text{-}3)$$

The corresponding choice of the coordinate value becomes $$(p4)_x = \cos\psi 1 \cos\theta 1 \sin\phi 2 = 0, \quad (18)$$

which requires that $\cos\psi 1 = 0$ and/or $\cos\theta 1 = 0$ and/or $\sin\phi 2 = 0$.

More generally, a coordinate axis c (=x or y or z) is chosen, a rotation $R_c(\chi_n)$ by an angle $\chi_n$ about the c-coordinate axis is carried out on a rotated projection vector $s_n = p_n$ or $q_n$ or $r_n$ (stage n=2, 3, . . . ), a corresponding plane, $\beta_n = xz$ or yz or xy (normal to the c-coordinate axis) is determined, and a value of a selected coordinate c' (c'=x or y or z; c'≠c) of the rotated projection, $R_c(\chi_n)\, s_{n+1} = p_{n+1}$ or $q_{n+1}$ or $r_{n+1}$, (stage n=2, 3, . . . , on the $\beta_n$-plane) is set equal to 0; equivalent to requiring that the c'-coordinate of the rotated projection $R_c(\chi_n)s_n$, expressible as $$R_c(\chi_n)(s_n)_{c'} = A_n\sin\chi n + B_n\cos\chi n + C_n \quad (19)$$

$$= [A_n^2 + B_n^2]^{1/2}\sin[\chi n + \alpha n] + C_n$$

$$= 0,$$

where $A_n$, $B_n$ and $C_n$ and $\alpha_n$ are determined from preceding relations, the quantity $[A_n^2 + B_n^2]^{1/2}$ is constrained by $$|C_n| \le [A_n^2 + B_n^2]^{1/2}, \quad (20)$$

(unless $A_n = B_n = 0$), and the only variable in Eq. (19) is the angle $\chi n$, which is chosen to satisfy Eq. (19). The numerical values of $A_n$, $B_n$ and $C_n$ depend upon the previously determined angle values. For stage n, the orthogonal transformation $R_x(\chi n)$, with $\chi n$ equal to its optimal value, is applied to produce the second stage projection vectors, p(n+1), q(n+1) and r(n+1), dependent upon $\chi n$ and upon the previously determined angles $\phi 0$, $\phi 1$, $\psi 0$, $\psi 1$, $\theta 0$ $\theta 1$, $\phi 2$, etc.

Generally, the nth stage projection vectors, pn, qn and rn are determined using orthogonal transformations, $$p(n+1) = R_c(\chi n)pn, \quad (21\text{-}1)$$

$$q(n+1) = R_c(\chi n)qn, \quad (21\text{-}2)$$

$$r(n+1) = R_c(\chi n)rn, \quad (21\text{-}3)$$

where $\chi n$ is a rotation angle to be determined and the index c indicates the rotation axis (c=x, y, or z) to be used for the nth stage orthogonal transformation.

At stage n=2 and beyond, in the iterative rotation procedure, the rotation angles $\phi 1$, $\psi 1$, $\theta 1$ and $\phi 2$ are to be determined according to criteria that are not yet identified. Careful analysis of the expressions for pn, qn and rn (e.g., n=2, 3, 4 and beyond) indicates that, for each of these stages, at least one (anomalous) vector component for each of pn, qn and rn does not provide for adjustment of the corresponding rotation angle $\chi n$, because the anomalous vector component does not explicitly depend upon the corresponding rotation angle $\chi n$. For stages n=1, 2, 3, 4, for example, the anomalous vector components are $$n=1: (p1)_y, (q1)_y, (r1)_y;$$

$$n=2: (P2)_x, (q2)_x, (r2)_x;$$

$$n=3: (p3)_z, (q3)_z, (r3)_z;$$

$$n=4: (p4)_y, (q4)_y, (r4)_y.$$

$$n=5: (P5)_x, (q5)_x, (r2)_x;$$

$$n=6: (p6)_z, (q6)_z, (r4)_z.$$

$$n=7: (p7)_y, (q7)_y, (r4)_y.$$

etc.

In each stage, the anomalous vector component corresponds to the orthogonal rotation axis.

Because of these anomalies, the rotation angles $\phi 1$, $\psi 1$, $\theta 1$ and $\phi 2$ will be determined as follows:

(1) $\phi 1$ is chosen so that the projection vector p1 lies in the xz-plane; more particularly along the z-axis ($\phi 0 + \phi 1 = 0$ or $\pi$) or along the x-axis ($\phi 0 + \phi 1 = \pi/2$ or $3\pi/2$);

(2) $\psi 1$ is chosen so that q2 lies in the xy-plane (z-component of q2 is 0); or (3) $\theta 1$ is chosen so that r3 lies in the xz-plane (y-component of r3 is 0); and so on.

After termination of this sequential procedure (at stage n), the resulting vector triple, pn, qn, rn, collectively provides an estimation of the original vector triple, p0, q0, r0, as transformed by the preceding rotations to a modified angular configuration or perspective that may be more convenient to apply a subsequent analysis. In the modified perspective, the triple of projections, pn, qn, rn, lies in a plane that is defined by two of the three coordinate axes. This is useful in estimating the actual three-dimensional length L of the initial vector that corresponds to the triple p0, q0, r0.

This procedure is applied at each of N stages (n=2, 3, ..., N) to provide stage n projection vectors and corresponding rotation vectors $\chi_n$, $$p_{n+1}=R_c(\chi_n)p_n, \quad (22\text{-}1)$$

$$q_{n+1}=R_c(\chi_n)q_n, \quad (22\text{-}2)$$

$$r_{n+1}=R_c(\chi_n)r_n, \quad (22\text{-}3)$$

where a selected c-coordinate of $s_{n+1}$ is 0. Optionally, the process terminates when the optimum angle of rotation $\chi_{n+1}$ at stage n satisfies a threshold criterion, such as $$|\chi_{n+1}| \leq \chi(\text{thr}) \quad (23)$$

for a selected positive angle value $\chi(\text{thr})$. The anticipated result is a set of Nth stage projection vectors that approximately represent optimal views of this ASJ component, referenced to the coronal, axial and sagittal perspectives.

One goal here is estimation of an actual length L and an angular orientation of the line segment LS from the measured lengths, $L_{xz}=|p|$, $L_{yz}=|q|$, and $L_{xy}=|r|$, and corresponding angular orientations, $\phi 0$, $\psi 0$, and $\theta 0$, associated with the projections. Ideally, the projection vectors, p, q and r, would be aligned with the y-axis, the y-axis and the z-axis, respectively, which would correspond to $\phi 0=0$, $\psi 0=0$, and $\theta 0=0$. Application to the three projection vectors, p0, q0 and r0, of a three dimensional orthogonal transformation T, satisfying $T^{tr} \cdot T = T \cdot T^{tr} = I$ (identity matrix), will preserve the scalar product values, p0·q0, q0·r0 and r0·p0, so that no orthogonal transformation will convert non-orthogonal vectors p0, q0 and r0 into an orthogonal vector triad. However, iteration of a sequence of orthogonal transformations associated with rotations about the x- y- and z-axes may transform the initial vector triad {p0, q0, r0} into a vector triad that is "optimal" in some sense for that stage.

As an example, a (truncated) sequence of orthogonal transformations, $$R_y(\phi 2)R_z(\theta 1)R_x(\psi 1)R_y(\phi 1)$$

(applied from right to left according to the conventional rules for matrix multiplication) is applied to individual members of the vector triad {p0, q0, r0}. At each stage the corresponding rotation angle, $\phi 1$, $\psi 1$, $\theta 1$, $\phi 2$, etc., is chosen to provide an optimal (in some sense) correspondence to a suitable coordinate axis, x, y or z. Each of the rotation angles, $\phi 1$, $\psi 1$, $\theta 1$, $\phi 2$, etc., is chosen to provide a further optimization, relative to the corresponding x-, y- or z-axis so that each individual rotation $R_c(\chi_n)$ (c=x, y or z; $\chi = \phi 1$, $\psi 1$, $\theta 1$, $\psi 2$, etc.) implements an additional rotation of the triad {p0, q0, r0} that is at least as optimal as the immediately preceding rotation $R_c(\chi_{n-1})$. After termination of the procedure, the resulting sequence of rotations provides an estimate of the angular orientation of the original line segment LS. This orientation can be applied to estimate a preferred angular orientation of a cut plane for orthopaedic joint replacement, for example, normal to direction of the line segment LS.

In order to achieve efficiency, the rotation axes associated with two consecutive rotations, $R_c(\chi_n)$ and with $R_c(\chi_{n-1})$ (c=x, y or z) do not coincide with each other. For the example discussed in the preceding, the first rotation axis RA1 associated with $R_c(\chi)$ may be the x-, y- or z-axis; the second rotation axis RA2 is chosen from among the two rotation axes not chosen for RA1; the third rotation axis RA3 is chosen from among the two rotation axes not chosen for RA2; and, more generally, the rotation axis RAn (n=2, 3, ...) is chosen from among the two rotation axes not chosen for RA(n−1). Thus, the first rotation axes RA1 is chosen from any of the three axes, x- y- and z; and the nth rotation axis RAn (n≥2) is chosen from the two axes not chosen for RA(n−1).

FIGS. 19, 19A and 19B illustrate a two-dimensional curve $\chi(x,y)=0$, 302A/301B, representing one MRI slice 301A of an ASJ structure, and angles associated with angles, ($\psi_m$, $\theta_m$, $\varphi_m$) on a curve associated with each selected location on the curve. The angles, $\psi_m$ and $\theta_m$, may vary with the location coordinates ($x_m, y_m$), but the angle $\varphi$ is temporarily fixed for each computation of $w(\varphi)$.

With reference to an (x,y) coordinate system, a wear vector $w(\varphi)$ is applied with an associated angle $\varphi$ (temporarily fixed) to each location on the curve $\chi(x,y)=0$ with coordinates ($x_m, y_m$). The curve $\chi(x,y)=0$ is assumed to be well approximated by a continuously differentiable curve having an associated unit length tangent vector $T(\theta_m)$ with corresponding x- and y-coordinates ($\cos(\psi_m)$, $\sin(\psi_m)$). The curve $\chi(x,y)=0$ at the location ($x_m, y_m$) also has a unit length vector $N(\theta_m)$ normal to this curve, and the wear vector $w(\varphi)$ is oriented at an angle $\psi_n$ relative to the normal vector $N(\theta_m)$ at the location ($x_m, y_m$). The angle $\psi_m$ is a measure of angular difference between a vector $N(\theta_m)$ that is normal to the curve $\chi(x,y)=0$ at the location ($x_m, y_m$) and the wear vector $w(\varphi)$. The angle $\theta_m$ is a measure of angle between the normal vector $N(\theta_m)$ and a fixed direction, such as the y-axis (fixed). From the illustrations of the angles in FIG. 19, one verifies that $$\varphi = \theta_m - \psi_m. \quad (24)$$

Each segment of the curve $\chi(x,y)=0$ extending between ($x_{m-1}, y_{m-1}$) and ($x_{m+1}, y_{m+1}$) is approximated by a quadratic polynomial, $y(x)=a_0+a_1 x+a_2 x^2$, where measurable y-values satisfy $$y(x=x_{m-1})=y_{m-1}, \quad (25\text{-}1)$$

$$y(x=x_m)=y_m, \quad (25\text{-}2)$$

$$y(x=x_{m+1})=y_{m+1}, \quad (25\text{-}3)$$

At any location (x,y) on the curve $\chi(x,y)$, the tangent vector $T(\theta_m)=(-\cos(\pi/2-\theta_m), \sin(\pi/2-\theta_m))=i\cos\theta_m + j\sin\theta_m$ and the x-derivative of the curve $\chi$ are related by $$dy/dx = a_1 + 2a_2 x = \tan\theta(x), \quad (26)$$

where the values $a_0$, $a_1$ and/or $a_2$ may vary from one segment to the next. A unit length vector $$N(\theta_m) = (-\sin(\theta_m), \cos(\theta_m)) \quad (27)$$

$$= -i\sin\theta_m + j\cos\theta_m,$$

which is normal to the curve $\chi(x,y)=0$ at $(x_m,y_m)$, is also defined. The unit length vectors, i and j, are parallel to the x-axis and y-axis, respectively.

Figure 20:
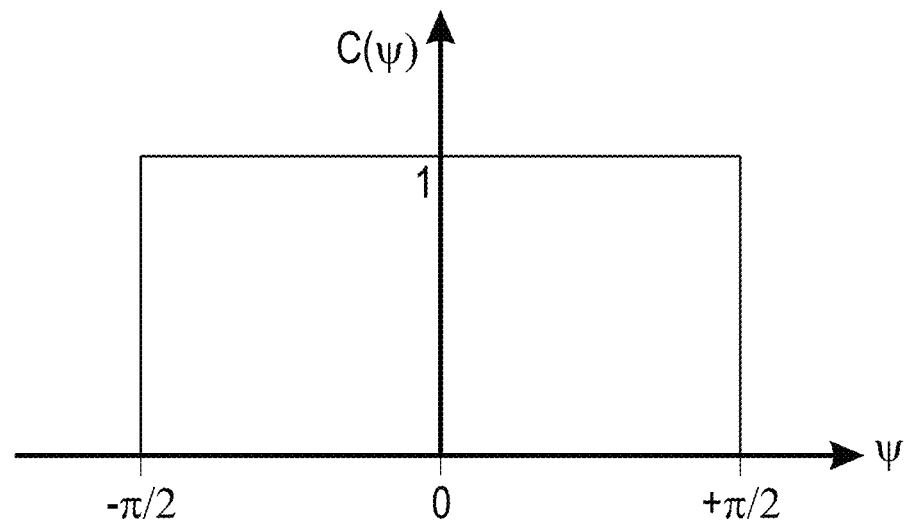
FIG. 20 graphically illustrates an opacity curve that is applied to an analysis of the curve $\chi(x,y)=0$.

Using the geometrical quantities illustrated in FIGS. 19, 19A and 19B and the Equations (24), (26) and (27), a normal component of wear vector, $E0\{N(\theta_m)\cdot w\}\ N(\theta_m)=E0\cos(\theta_m)$ for a curvilinear segment $\chi(x,y)=0$ can be expressed as a sum, $\varphi=\theta_m-\varphi_m$, $$w(\phi) = \sum_{p=m-1}^{m+1} E0N(\theta_p)\cos\psi_p C(\psi_p) \tag{28}$$

$$= \sum_{p=m-1}^{m+1} E0(-i\sin\theta_p + j\cos\theta_p)\cos(\phi-\theta_p)C(\phi-\theta_p)$$

$$= iw1(\varphi) + jw2(\varphi),$$

$$w1(\phi) = -\sum_{p=m-1}^{m+1} E0\sin(\theta_p)\cos(\phi\,\theta_p)C(\phi\,\theta_p), \tag{29A}$$

$$w2(\phi) = -\sum_{p=m-1}^{m+1} E0\cos(\theta_p)\cos(\phi-\theta_p)C(\phi-\theta_p), \tag{29B}$$

$$C(\psi) = 1 \quad (|\psi| < \pi/2), \tag{30A}$$

$$= 0 \quad (|\psi| \geq \pi/2),$$

where the index in Eqs. (29A) and (29B) is summed over consecutive coordinate triples, $\{(x_{m-1},y_{m-1}), (x_m,y_m), (x_{m+1},y_{m+1})\}$, $E0$ is a non-zero physical constant representing a reference (normal) value of wear, and $C(\psi)=C1(\cos\psi)$ is an opacity factor (graphically illustrated in FIG. 20 that takes account of the fact that a contribution to wear vector $w(\varphi)$ vanishes for values of $\psi$ directed from the "inside" of the curve $\chi(x,y)=0$, corresponding to values $|\psi|\geq\pi/2$. The opacity factor $C(\psi)$ in Eq. (26) can be replaced by an equivalent opacity factor $$C1(\cos\psi) = 1 \quad (\cos\psi) > 1 \tag{30B}$$
$$\quad\quad\quad\quad 0 \quad (\cos\psi) \leq 1$$

Optionally, the opacity factor, $C(\psi)$ or $C1(\cos\psi)$, can be replaced by a constant value, such as 1, if variable opacity is ignored, or by another function of the variable $\psi$.

The wear vector $w(\varphi)$ for the curve $\chi(x,y)=0$ of interest (e.g., Eq. (26)) can be minimized by requiring that $$W(\varphi) = w(\varphi)\cdot w(\varphi) = w1(\varphi)^2 + w2(\varphi)^2, \tag{31A}$$

$$\{\partial/\partial\varphi\}W(\varphi) = \{\partial/\partial\varphi\}\{w(\varphi)\cdot w(\varphi)\} \tag{31B}$$

$$= 2\{w1(\varphi)\{\partial/\partial\varphi\}w1 + w2(\varphi)\{\partial/\partial\varphi\}w2\}$$

$$= -2\sum_{p,q=m-1}^{m+1} E0^2\cos(\theta_p+\theta_q)\cos$$

$$(\phi-\theta_q)C(\phi-\theta_p),$$

-continued $$= -2\sum_{p,q=m-1}^{m+1} E0^2\cos(\theta_p+\theta_q)$$

$$\{\sin(2\phi-\theta_p-\theta_q)+\sin(\theta_p-\theta_q)\}$$

$$C(\phi-\theta_p)C(\phi-\theta_q),$$

where the index m is summed over consecutive coordinate triples (p, q=m−1, m, m+1), and $\partial C/\partial\varphi=0$, except on a set of coordinates of measure zero. The physical constant quantity $E0$ can be deleted in Eqs. (27A), (27B), (31A) and (31B).

Figure 21:
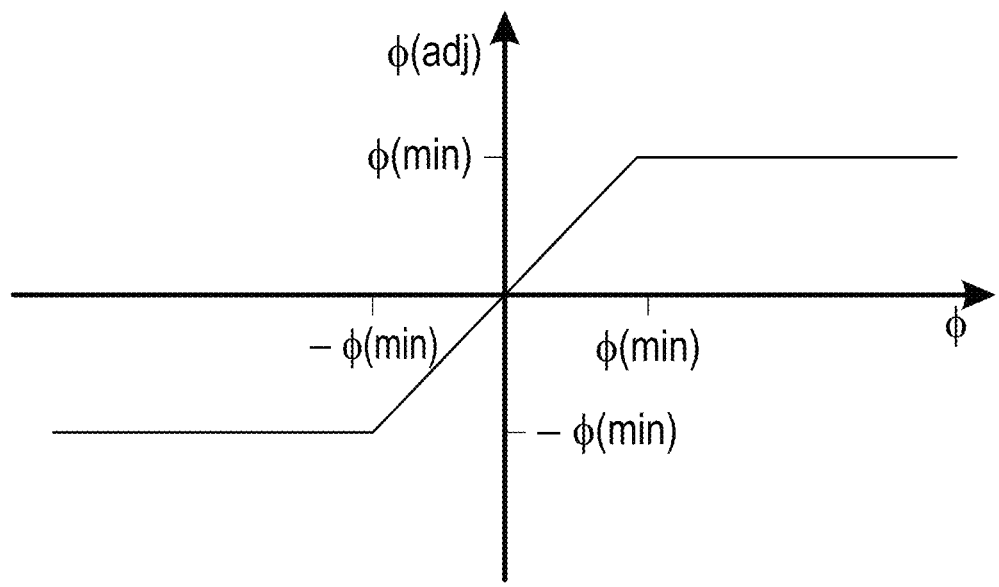
FIG. 21 graphically illustrates an approach for limiting a range of an optimal offset value $\varphi(min)$.

The sum over a coordinate triple (p, q=m−1, m, m+1) in Eq. (28) is extended from the range, $x_{m-1}\leq x\leq x_{m+1}$, to the entire curve $\chi(x,y)=0$, by appropriately adjusting the upper index limit and/or the lower index limit in the double sum. Where the magnitude of the optimal wear solution value, $z=\phi=\phi(\min)$, is no larger than a maximum value, $\phi(\text{MAX})$ (e.g., a few degrees), the optimal value can be used to adjust angular orientation of an ASJ cutting jig. Where this magnitude is greater than $\phi(\text{MAX})$, one may use an adjusted value, defined by $$\phi(z;adj) = (0.5)\{|z-z1|-|z-z2|\} \tag{32}$$

$$= (0.5)\{|\phi-z1|-|\phi-z2|\}$$

$$z1=-z2=-\phi(\min), \tag{33}$$

and illustrated in FIG. 21, which is constant above $\phi=+\phi(\min)$, is constant below $\phi=-\phi(\min)$ and is continuous and monotonically increasing with increasing $\phi$ between values z1 and z2.

Figure 22:
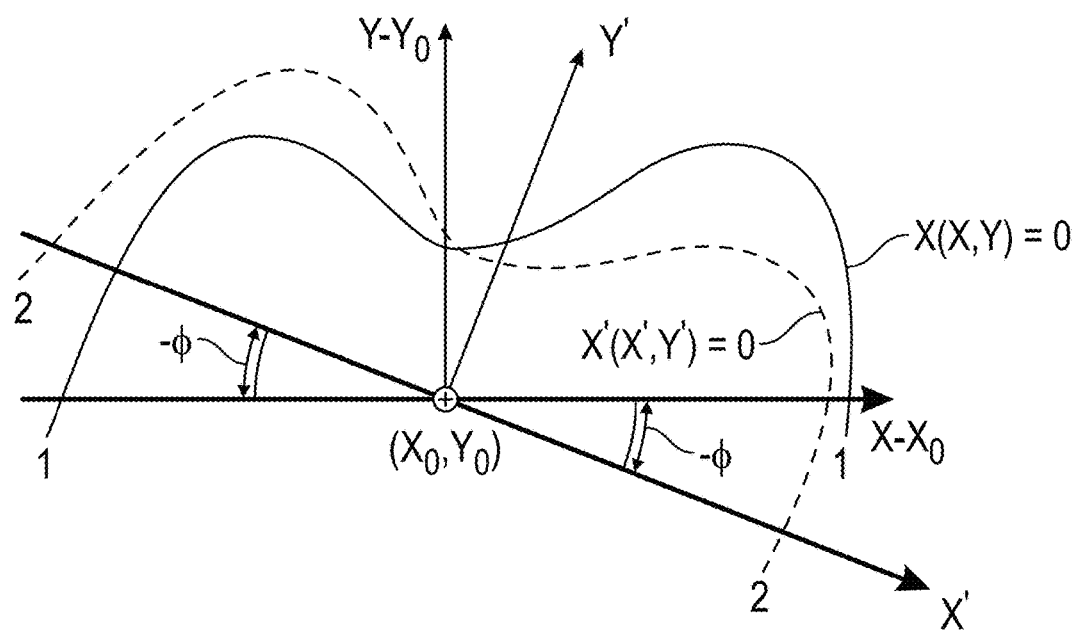
FIG. 22 illustrates implementation of angle correction by an amount $-\varphi$.

The x-axis and y-axis of the coordinate system are re-aligned (rotated) by an offset angle $-\varphi$ in order to adjust the wear vector to a minimal value, as illustrated in FIG. 22.

$$x'=(x-x0)\cos\varphi-(y-y0)\sin\varphi, \tag{34A}$$

$$y'=(x-x0)\sin\varphi+(y-y0)\cos\varphi, \tag{34B}$$

where (x0,y0) are coordinates of a center of rotation, such as $$(x0, y0) = \sum_p (x_p, y_p)/N \tag{35}$$

Definition of coordinates (x0,y0) for the center of rotation is arbitrary but should not affect the value p(min) determined herein. Under this rotation, the original curve $\chi(x,y)=°$ becomes a rotated curve $\chi'(x',y')=0$. Assuming that the solution, $\phi=\phi(\min)$, of Eq. (31B) is no more than a few degrees (±), this minimum angle value is interpreted as a correction angle to be applied to an ASJ structure, represented by a slice. Each of several (approximately parallel) image slices, numbered k=1, 2, . . . , K, may have a different associated minimization angle, $\phi=\phi(k;\min)$ (k=1, . . . , K). A suitable representative value, $\phi=(\text{rep;min})$, may be a statistical average, for example, a weighted arithmetic average or a median value, $\phi(\text{avg;min})$, where only values, $\phi=\phi(\min;k)$, with magnitudes no greater than a threshold value $\phi(\text{MAX})$ (e.g., ≤3° or ≤6°) are used to form a statistical average. The minimization relations, Eqs. (32) and (33), are preferably applied separately to each independent ASJ structure or slice (e.g., separately to a femur slice, to a tibia slice, and/or to a shoulder slice), in determining an optimal offset angle $\phi$ that may be applied to an angular orientation of a cutting jig for a femur, a tibia, a femur neck, an acetabulum, a shoulder component, or another ASJ structure of interest.

FIGS. 19A and 19B illustrate slices that might be obtained for a femur (e.g., medial and lateral condyles of a knee) 301A and for a tibia, respectively. A wear vector $w(\phi)$ in FIG. 19B would be analyzed in the same manner that a wear vector is analyzed in FIG. 19A.

Another embodiment takes account of variation of distances and angles, $$\Delta s_m = [(x_{m+1} - x_{m-1})^2 + (y_{m+1} - y_{m-1})^2]^{1/2}, \quad (36A)$$

$$\eta_m = \tan^{-1}\{(y_{m+1} - y_{m-1})/(x_{m+1} - x_{m-1})\} \quad (36B)$$

between ends of different line segment triples (represented by unit vectors $H_m = (\cos \eta_m, \sin \eta_m)$, as illustrated in FIG. 19, and variations of angular orientation $\eta_m$ of the vector $H_m$, relative to a local tangent vector $T (\theta_m)$ for the curve $\chi(x,y)=0$. For this embodiment, the expression for an intermediate wear vector $w(\phi)$ is multiplied by a factor $\{\Delta s_m \tan (\theta_m - \theta_m)\}$, where $(\theta_m - \eta_m)$ is an angular difference between the unit vector $H_m$ and a tangent line vector, $T_m = (\cos\theta_m, \sin\theta_m)$ for the curve $\chi(x,y)=0$, as illustrated in FIGS. 19A, 19B and 22. For this second embodiment, the wear vector $w'(\phi)$ is expressed as $$w'(\phi) = \sum_{p=m-1}^{m+1} E0 N(\theta_p) \cos^2 \psi_p \cos(\theta_p - \eta_p) \Delta s_p (C(\psi_p)) \quad (37)$$

$$w'(\phi) = \sum_{p=m-1}^{m+1} E0\{-i \sin\theta_p + j \cos\theta_p\} \cos^2$$
$$(\theta - \phi_p) \cos(\theta_p - \eta_p) \Delta s_p C(\theta - \phi_p)$$
$$= i w1'(\varphi) - j w2'(\varphi),$$

$$w1'(\phi) = -\sum_{p=m-1}^{m+1} E0 \cos(\theta - \phi_p) \sin\theta_p \cos(\theta_p - \eta_p) \Delta s_p C(\theta - \phi_p) \quad (38)$$

$$w2'(\phi) = -\sum_{p=m-1}^{m+1} E0 \cos(\theta - \phi_p) \cos\theta_p \cos(\theta_p - \eta_p) \Delta s_p C(\theta - \phi_p) \quad (39)$$

$$N(\theta_p) = -i \sin\theta_p + j \cos\theta_p, \quad (40)$$

$$\tan (\eta_m) = (y_{m+1} - y_{m-1})/(x_{m+1} - x_{m-1}), \quad (41)$$

$$\Delta s_m \cos \eta_m = x_{m+1} - x_{m-1}, \quad (42)$$

$$\Delta s_m \sin \eta_m = y_{m+1} - y_{m-1}. \quad (43)$$

The normal vector $N(\theta_m)$ is a unit length vector oriented in a direction of momentum transfer associated with the (incremental) wear vector $w(\phi)$. The quantity $\cos(\theta_m - \eta_m)$ is a scalar product of a unit length tangent vector $T(\theta_m) = (\cos\theta_m, \sin\eta_m)$ and a unit length vector $H_m$ that is parallel to a line segment joining the locations $(x_{m-1}, y_{m-1})$ and $(x_{m+1}, y_{m+1})$, shown in FIGS. 19A, 19B and 23. Note that only the terms $\cos (\varphi - \theta_m)$ and $C(\varphi - \theta_m)$ involve the angle variable $\varphi$.

A scalar product (magnitude squared)

$$W(\varphi) = w'(\varphi) \cdot w'(\varphi) = w1'(\varphi)^2 + w2'(\varphi)^2, \quad (44)$$

of the normal wear vector $w(\varphi)$, set forth in Eqs. (36), (37) and (38), is formed, and an optimal value of an offset value, $\varphi = \varphi(\min)$, is estimated from a solution of the equation $$\partial W/\partial\varphi = 2\{w1'(\varphi)\partial w1'/\partial\varphi + w2'(\varphi)\partial w2'/\partial\varphi\} \quad (45A)$$

$$W(\varphi) = w1'(\varphi)^2 + w2'(\varphi)^2. \quad (45B)$$

In a third embodiment, independent first and second optimal angles, $\varphi = \varphi1(\min)$, and $\varphi = \varphi2(\min)$, can be estimated as solutions of the respective equations $$\partial w1/\partial\varphi(\varphi = \varphi1(\text{Min})) = 0, \quad (46)$$

$$\partial w2/\partial\varphi(\varphi = \varphi2(\min)) = 0, \quad (47)$$

or a weighted sum or other linear or nonlinear combination of $\varphi1$ (min) and $\varphi2$ (min) can be used to estimate $\varphi(\min)$, corresponding to the respective constant vector directions i and j. Estimation of an optimal offset angle is not limited to the values of $\varphi$ satisfying one or more of the Eqs. (45A), (46) and/or (47).

The first and second embodiments may be integrated by re-expressing Eq. (37) as $$w'(\phi) = \sum_{p=m-1}^{m+1} E0\{-i \sin\theta_p + j \cos\theta_p\} \cos^2(\phi - \theta_p)[\text{mod}] C(\phi - \theta_p) \quad (48\text{-}1)$$
$$= i w1'(\varphi) - j w2'(\varphi),$$

where the user chooses $$[\text{mod}] = \cos (\theta_p - \eta_p) \Delta s_p \text{ or} \quad (48\text{-}2)$$

$$[\text{mod}] = 1. \quad (48\text{-}3)$$

Figure 23:
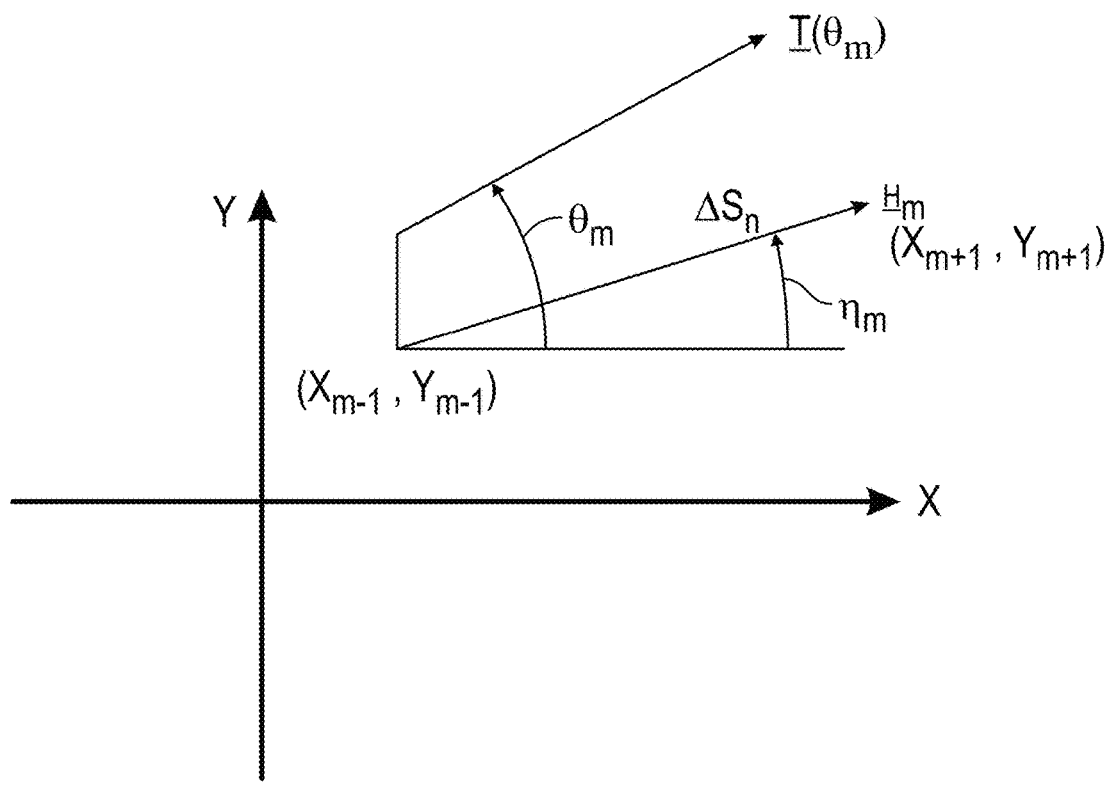
FIG. 23 graphically illustrates a geometric relationship between a slope of the curve $\chi(x,y)=0$ and an angle $\theta$ in FIGS. 19A and 19B.

The preceding development focuses on analysis of embodiments of normal (perpendicular-oriented) wear for an ASJ structure, directed normal to the local ASJ structure that is represented by the curve $\chi(x,y)=0$. Where the ASJ structure of interest is a tibia, for example, interest may also focus on shear stress, involving a combination of a normal component of wear and a tangential component of wear. FIG. 23 illustrates elastic stress components of interest here, where stress, corresponding to a modified wear vector, is now expressed as a vector sum of: (1) a stress component oriented normal to the curve $\chi(x,y)=0$, expressed as E0 $(\sigma \cdot N)N$, and (2) a stress component oriented tangent to the curve $\chi(x,y)=0$, expressed as G0 $\{\sigma - (\sigma \cdot N)N\}$, where c is a dimensionless vector associated with $w(\varphi)$ and G0 is a non-zero physical constant representing a shear component of wear. Tangent stress component is represented here by $G0 T(\theta_p)$.

The normal and tangential stress components include a longitudinal stress modulus E0 (constant) and a shear stress modulus G0 (constant), respectively, at least one of which is non-zero, which may be but need not be equal. A wear vector $w(\varphi)$ associated with shear stress for a curve segment (p=m−1, m, m+1) is expressed as a sum $$w(\phi) = \sum_{p=m-1}^{m+1} E0\cos(\phi - \theta_p) n1(\theta_p) C(\phi - \theta_p) + \quad (49)$$
$$\sum_{p=m-1}^{m+1} G0 \sin(\phi - \theta_p) n2(\theta_p) C(\phi - \theta_p)$$

Here, $$n1(\theta_p) = -i \sin \theta_p + j \cos \theta_p = N(\theta_p), \quad (50A)$$

$$n2(\theta_p) = i \cos \theta_p + j \sin \theta_p = T(\theta_p), \quad (50B)$$

are unit length vectors oriented in the vector directions N and T, respectively, in FIGS. 19A, 19B and 24, and i and j are unit length vectors, fixed in direction and oriented along the x-axis and y-axis, respectively. The wear vector w(φ) in this embodiment is expressed as $$w(\phi) = \sum_{p=m-1}^{m+1} \{N(\theta_p)E0\cos\psi_p + T(\theta_p)G0\sin\psi_p\}C(\psi_p) \quad (51)$$

$$= \sum_{p=m-1}^{m+1} \{(-i\sin\theta_p)E0\cos\psi_p + (i\cos\theta_p G0\sin\psi_p)\}C(\phi - \theta_p) +$$

$$\sum_{p=m-1}^{m+1} \{(j\cos\theta_p)E0\cos\psi_p + (j\sin\theta_p G0\sin\psi_p)\}C(\phi - \theta_p)$$

$$= iw1''(\varphi) - jw2''(\varphi).$$

An optimal wear angle value, φ=φ(min), is estimated using the relationships $$W''(\varphi)=w1''(\varphi)^2+w2''(\varphi)^2, \quad (52)$$

$$\partial W''/\partial \varphi=2\{w1''(\varphi)\partial w1''/\partial\varphi+w2''(\varphi)\partial w2''/\partial\varphi\}=0 \quad (53)$$

Estimating an optimal angle φ using the expressions in Eqs. (50A), (50B), (51), (52) and (53) is more challenging, because one deals simultaneously with vectors with two physical parameters, $E_0$ and $G_0$, or with $E_0$ and $G_0/E_0$, or with $G_0$ and $E_0/G_0$, which are assumed to be known but may vary from one patient to another.

In another embodiment, independent first and second optimal angles, φ=φ1(min), and φ=φ2(min), can be estimated as solutions of the equations $$\partial w1''/\partial\varphi(\varphi=\varphi1(\min))=0, \quad (54)$$

$$\partial w2''/\partial\varphi(\varphi=\varphi2(\min))=0, \quad (55)$$

$$\min\{\varphi1(\min),\varphi2(\min)\}\leq\varphi\leq\max\{\varphi1(\min),\varphi2(\min)\}. \quad (56)$$

A weighted sum or other combination of φ1(min) and φ2(min) can be used to estimate φ(min), corresponding to the respective constant vector directions i and j.

An offset angle, φ=φ(min), estimated according to one of the embodiments set forth in the preceding, or an equivalent embodiment, is preferably applied to adjust orientation angle of a cutting jig mechanism that will assist in defining an orthopedic joint replacement associated with an ASJ structure, as indicated in FIG. 23. Use of a single offset angle may be sufficient. Alternatively, first and second corresponding offset angles may be estimated and applied to first and second ASJ structures, for example, partial or full replacements for a femur and for a corresponding tibia. Preferably, the offset angle(s) φ should be estimated or otherwise determined before a cutting jig mechanism is implemented for an ASJ structure.

Figure 24A:
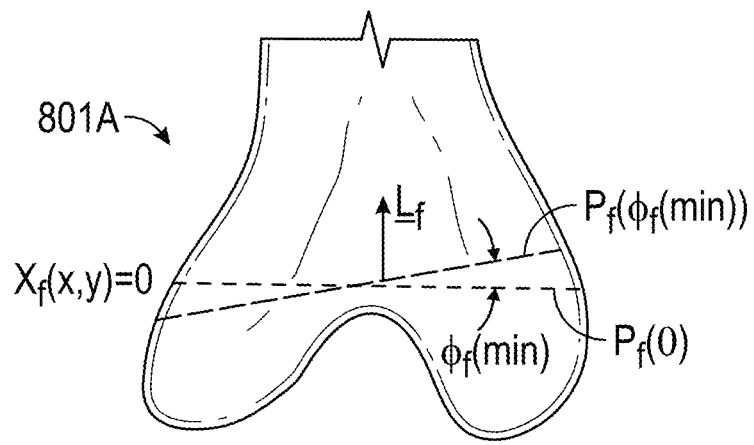
FIGS. 24A and 24B illustrate two situations in which angular misalignment of unit vectors associated with the optimal wear vector angles, $\varphi_f(min)$ and $\varphi_t(min)$, are small and are relatively large, respectively.
Figure 24B:
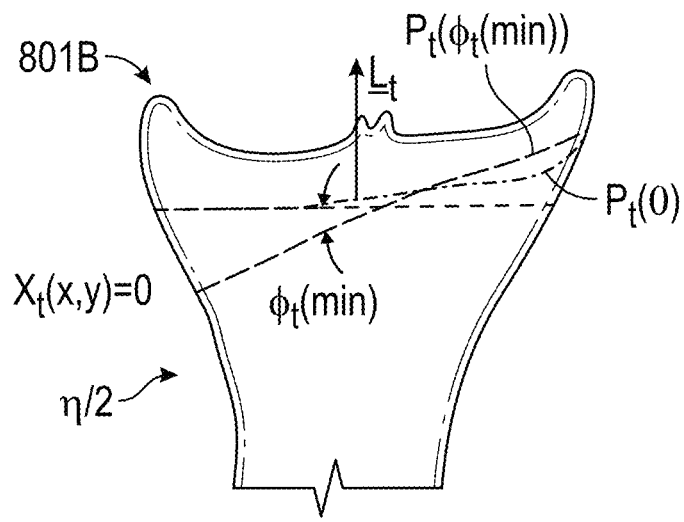
Figure 24C:
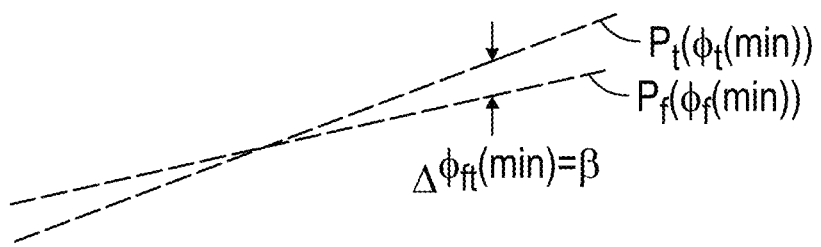
FIG. 24C illustrate scalar products and angles associated with the optimal wear vector angles, $\varphi_f(min)$ and $\varphi_t(min)$, corresponding to FIGS. 24A and 24B, respectively.

The (minimum) scalar normal wear vector value for the femur ($\chi_f(x,y)=0$), corresponding to an angle φ=φ$_f$(min), which is estimated in the preceding, or an estimated tangent (shear) wear value, is preferably used to estimate an offset angle relative to an initial choice of angular orientation of the femur ASJ structure 801A in FIGS. 24A-24C, indicated by an initial femur plane P$_f$(0). The initial plane P$_f$(0), which is determined in the procedure 101 in FIG. 17 as the femur initial planning/jig design coordinate system, does not take into account a femur minimum wear angle, φ=φ$_f$(min), determined in the preceding. A modified plane P$_f$(φ$_f$(min)), having an angular orientation rotated by an amount depending upon φ$_f$(min) relative to the initial femur plane P$_f$(0), is provided or determined.

Figure 25A:
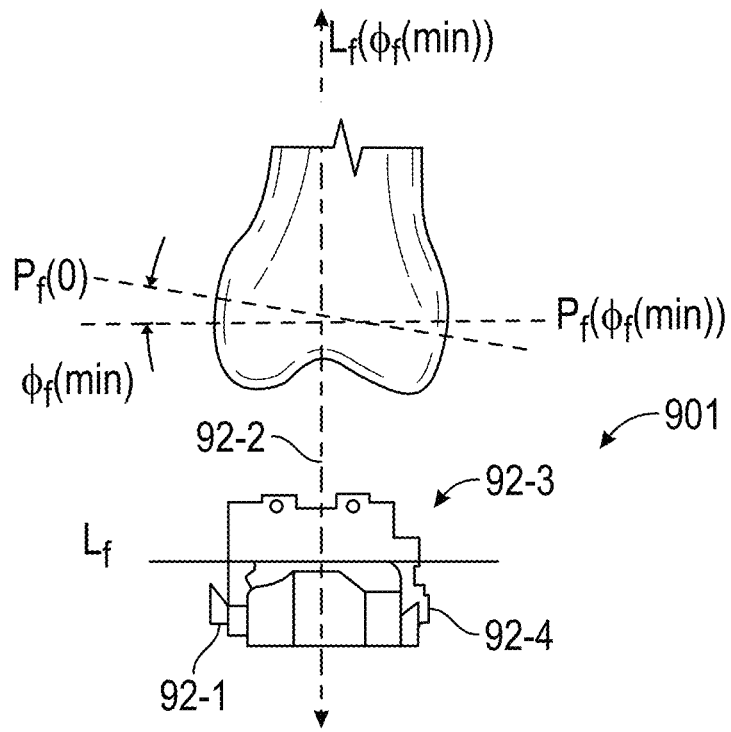
FIGS. 25A and 25B illustrate angular relationships between first and second cutting jig mechanisms associated with the femur and with the tibia, respectively.
Figure 25B:
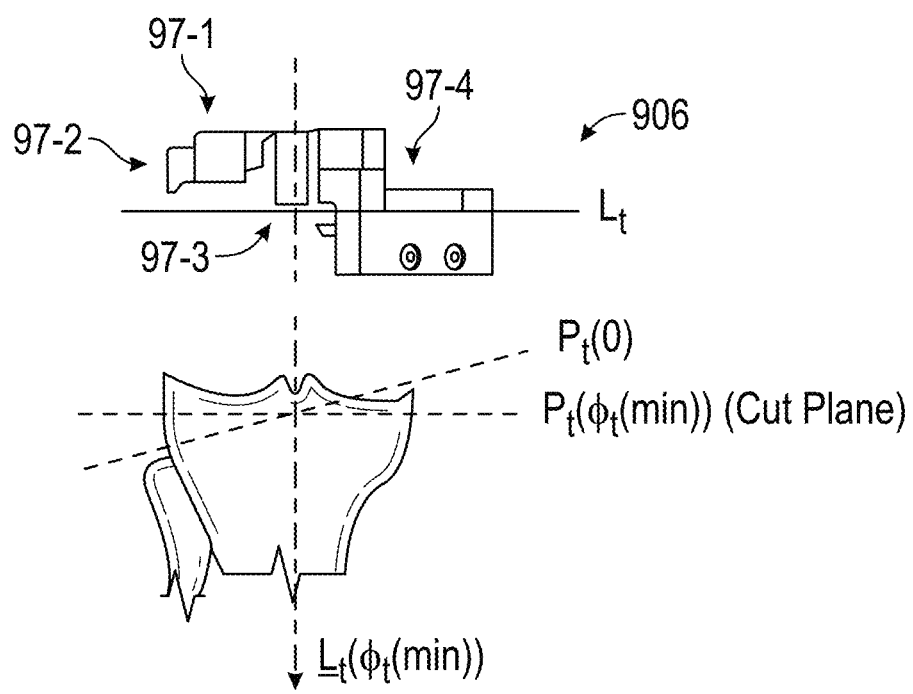

The (minimum) scalar normal wear vector value for the tibia ($\chi_t(x,y)=0$), corresponding to an angle φ=φ$_t$(min), which is estimated in the preceding, or an estimated tangent (shear) wear value, is preferably used to estimate an offset angle relative to an initial choice of angular orientation of the tibia ASJ structure 801B in FIG. 24B, indicated by an initial tibia plane P$_t$(0) in FIG. 25B. The initial plane P$_t$(0), which is determined in the procedure 101 in FIG. 17 as the tibia initial planning/jig design coordinate system, does not take into account a tibia minimum wear angle, φ=φ$_t$(min), determined in the preceding. A modified plane P$_t$(φ$_t$(min)), having an angular orientation rotated by an amount depending upon φ$_t$(min) relative to the initial tibia plane P$_t$(0), is provided or determined. The modified planes, P$_f$(φ$_f$(min)) and P$_t$(φ$_t$(min)), are estimated or determined from measurements taken from one or more MRI slices and from the optimal offset angles, φ$_f$(min) and φ$_t$(min), determined according to the preceding discussion.

The planes, P$_f$(0), P$_f$(φ$_f$(min)), P$_t$(0), and P$_t$(φ$_t$(min)), are represented in FIG. 24C by lines (e.g., as projections of these planes on one or more planes that do not lie in the plane of the paper). The initial tibia planes, P$_f$(0) and P$_t$(0), are determined by one or more MRI images (unmodified slices), with no account being taken of rotation of a slice by an optimal wear vector, φ$_f$(min) or φ$_t$(min), determined according to the preceding discussion. The modified planes, P$_f$(φ$^f$(min)) and P$_t$(φ$_t$(min)), have respective unit length normal vectors, L$_f$(φ$_f$(min)) and L$_t$(φ$_t$(min)), perpendicular to these modified planes, and the normal vectors, L$_f$(φ$_f$(min)) and L$_t$(φ$_t$(min)), are oriented at a differential angle β determined by $$L_f(\varphi_f(\min))\cdot L_t(\varphi_t(\min))=\cos\beta \quad (33)$$

as illustrated in FIG. 24C. The differential angle β=Δφ$_f$(min) is also a measure of angular misalignment of the modified planes, P$_f$(φ$_f$(min)) and P$_t$(φ$_t$(min)), relative to each other. Each of the normal vectors, L$_f$(φ$_f$(min)) and L$_t$(φ$_t$(min)), can be constructed from a vector cross product, (a^b)/|a^b|, of two non-aligned, non-zero vectors, a and b, lying in the plane, P$_f$(φ$_f$(min)), or in the plane P$_t$(φ$_t$(min)).

The normal vectors, L$_f$(φ$_f$(min)) and L$_t$(φ$_t$(min)), differ by a differential angle, β that is relatively small (e.g., magnitude |β| no greater than about 1°). This corresponds to a configuration in which a normal vector, L$_f$(0), of the femur ASJ 801A and a normal vector, L$_t$(0), of the tibia ASJ 801B are also approximately aligned, as illustrated in FIG. 25A. Two cutting jig mechanisms, 901 and 906, represented in FIGS. 25A and 25B, are introduced for the femur ASJ 801A and for the tibia ASJ 801B, respectively, which optionally compensate for the (small) differential angle β in the procedure 103 in FIG. 17. Alternatively, the cutting jig mechanisms, 901 and 906, are aligned in accord with the unit vectors, L$_f$(φ$_f$(min)) and L$_t$(φ$_t$(min)).

From the preceding discussion, it is clear that the wear vector optimal angle values, φ$_f$(min) and φ$_t$(min), influence, but do not necessarily wholly determine, the choice of the cutting jig orientation angles, α1 and α2, in situations where the magnitude |β| is substantial.

Figure 26A:
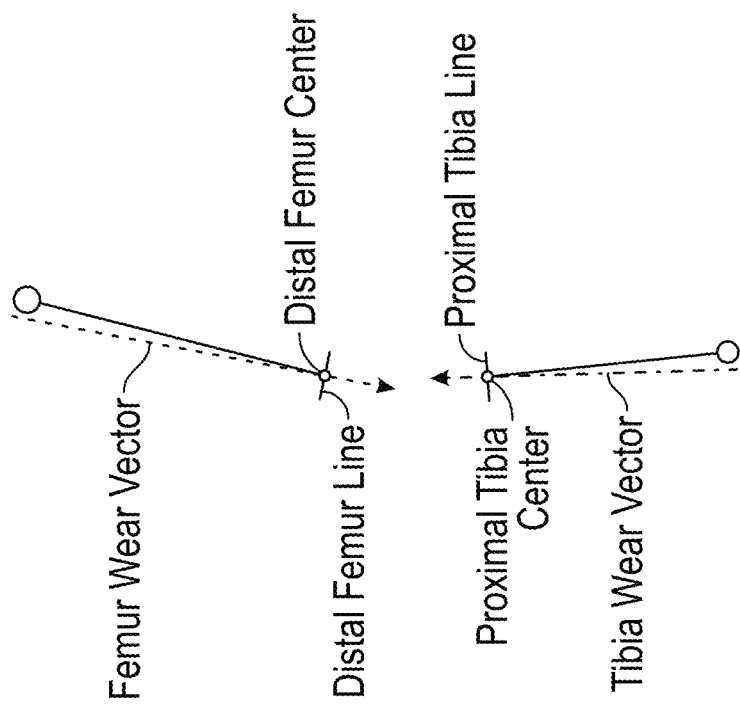
FIGS. 26A-26C are schematic views of lattice truss model of key locations already established from FIGS. 2 through 16 to illustrate application of a selected wear model.
Figure 26B:
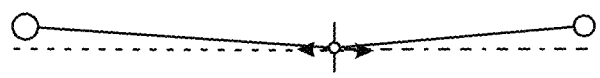
Figure 26C:
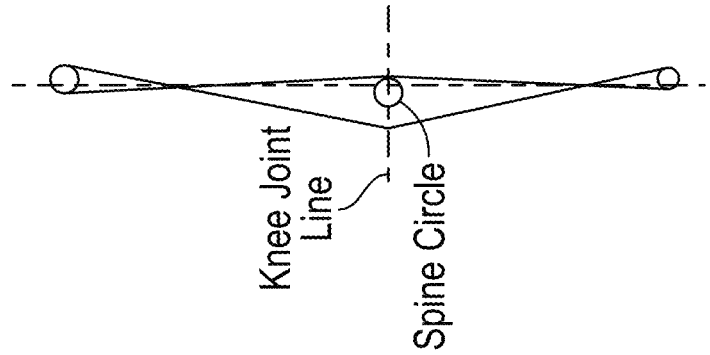

With reference to FIGS. 26A-26C, a lattice truss model derived from the marked positions from the preceding steps (FIGS. 1-25) is seen. A femur axis extends from the femoral head position (represented by the upper circle) to the distal femur center (the dot positioned at the center of the distal femur line). A femur wear vector (represented by a dashed line) is perpendicular to the distal femur line. Likewise, a tibia axis extends from the ankle center (represented by the lower circle) to the proximal tibia center (the dot positioned at the center of the proximal tibia line. A tibia wear vector (represented by another dashed line) is perpendicular to the proximal tibia line. In FIG. 26B, orientation of the femur and tibia axes have been at least partially straightened so that the distal femur line and proximal tibia line coincide at a common knee joint line and the respective femur and tibia wear vectors are aligned. In FIG. 26C, a number of additional lines are created between the femoral head, ends of the knee joint line, and ankle, and including a vertical line between femoral head and ankle. These are further specified with reference to FIGS. 28, 29, and 32A-32B.

FIG. 27A is a stand-up x-ray of the normal right leg 101 that consists of femur 115, tibia 113 and fibula 114. The proximal femur 105 exhibits the femoral head in FIG. 27B that includes the circle 106 and the center 105 representing the spherical shape of the femoral head 106. FIG. 27C shows the knee joint 103 that shows the knee joint line 109 between femur 115 and tibia 113 and the lateral and medial contact points 107 and 108. FIG. 27D shows the ankle joint that the tibia contact point 112 and fibula contact point 111 are displayed and the ankle line 110 represented by the connecting the two contact points 111 and 112. It is noted that in order to estimate the over-all limb alignment of a leg, three sets of MRI, distal femur, knee joint and ankle, are required.

Figure 28A:
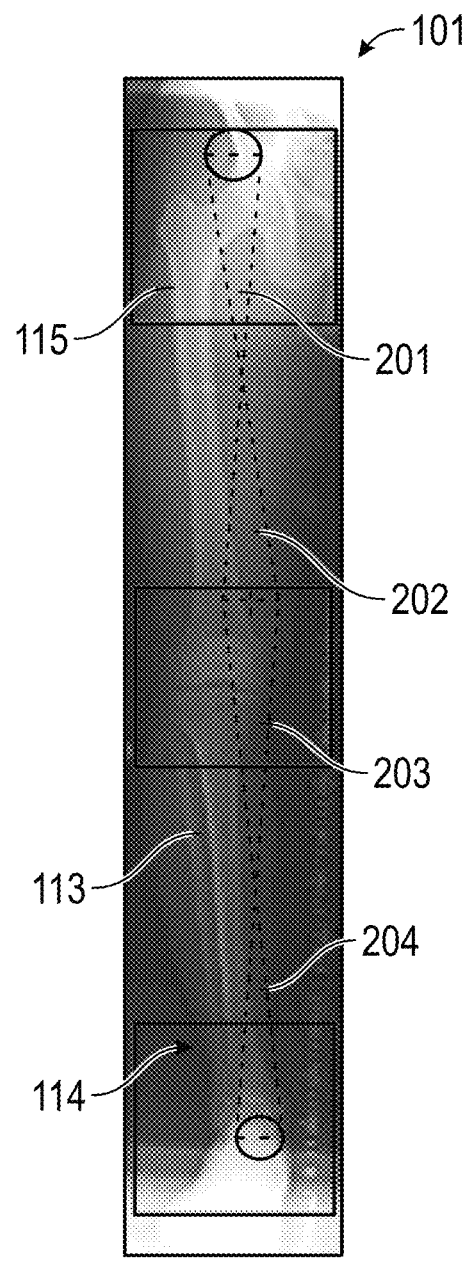
FIG. 28A shows the lattice truss set-up using the points defined in FIGS. 27A-27D.
Figure 28B:
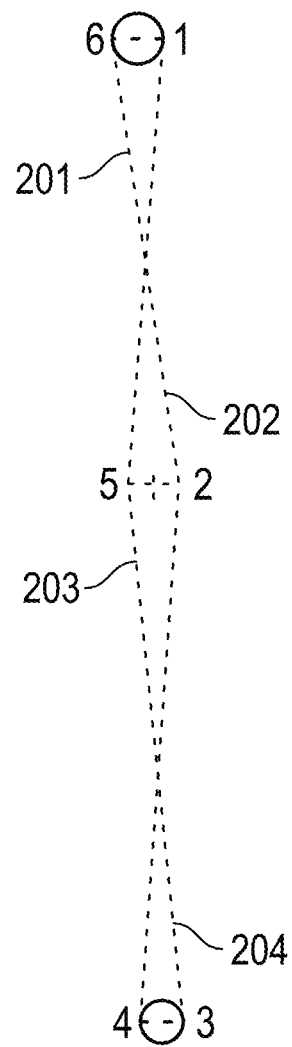
FIG. 28B is a lattice truss model of the leg.

FIG. 28 shows the lattice truss modeling procedure of the leg. The points 2 and 5 represent the medial and lateral contact points 108, and 107, respectively. The point 1 is a point that constructs the tangential line with the point 5, and the point 6 is a point that constructs the tangential line with the point 2 for femur 115. For tibia 113, the points 3 and 4 represent the medial and lateral contact points 112, and 111, respectively. By connecting each point in FIG. 2, the lattice truss structure is modeled representing over-all limb structure of the leg. Also, Line 16 and Line 34 are parallel to Line 25 representing the knee joint line.

Figure 29:
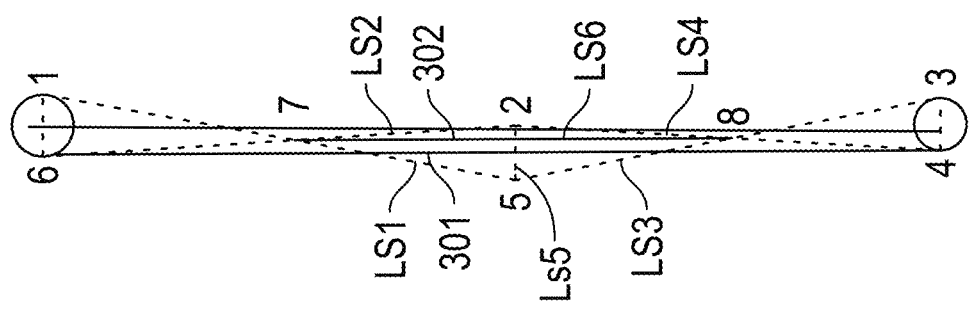
FIG. 29 shows the definition of the maximum lateral/medial bounds of the leg

FIG. 29 exhibits the further modeling of the lattice truss including the establishment of medial/lateral bounds. The points a, 2, 3, 4, 5, 6 are defined by the users on anatomies of MRI of the femoral head, knee joint and ankle. Line 25 represents the knee joint line. LS1 represents the line connecting between the points 1 and 5, and LS2 represents the line connecting between the points 2 and 6 for femur. LS3 represents the line connecting between the points 5 and 3, and LS4 represents the line connecting between the points 2 and 4 for tibia. Furthermore, the interval between the points 1 and 6 represents the femoral head bound, and the interval between the points 2 and 5 represents the knee joint bound. The interval between the point 3 and 4 represents the ankle bound. The point 7 is an intersection between the lines LS1 and LS2. The point 8 is am intersection between the lines LS4 and LS3. Finally, the knee joint line is represented by LS5. The line LS6 is a line connecting between he points 7 and 8. The lattice truss of the leg model should satisfy two major conditions for the leg stability in extension, i.e., stand-up position: (1) the line LS6 is perpendicular to the line LS5. (2) intersecting point between the lines LS5 and LS6 lies within the interval between the points 2 and 5; consequently, medial bound 302 and lateral bound 301, parallel to LS6, are formed, and the interval of which is said to be optimal in normal leg limb alignment.

Figure 30A:
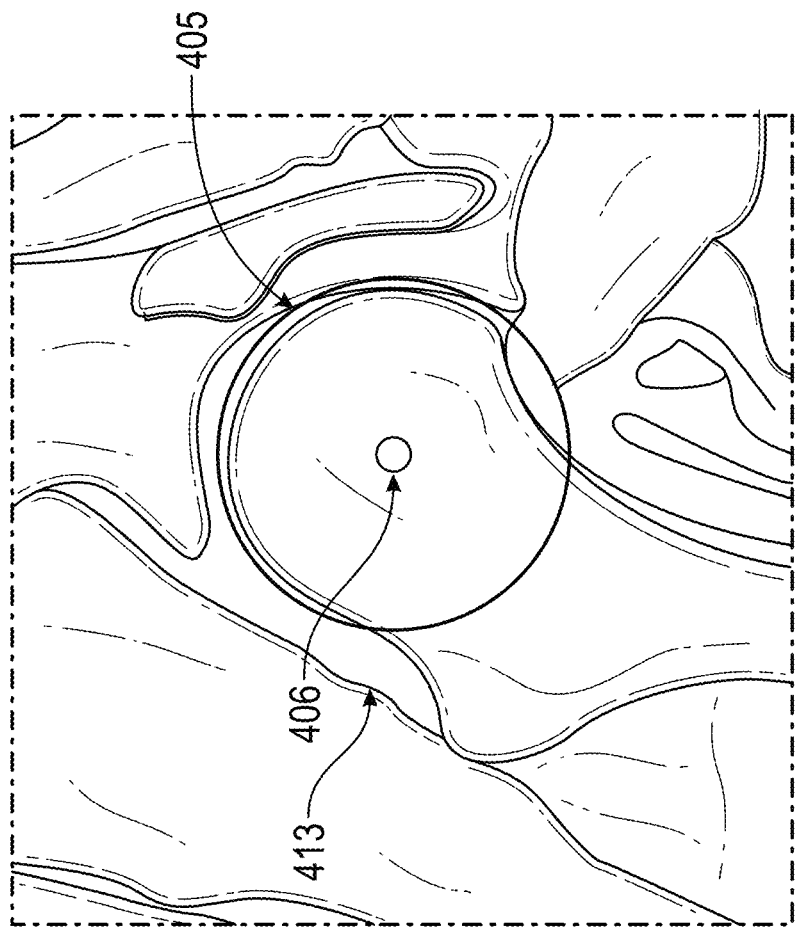
FIG. 30A is the geometric modeling of femoral head on MRI coronal view to set up lattice truss structure.
Figure 30B:
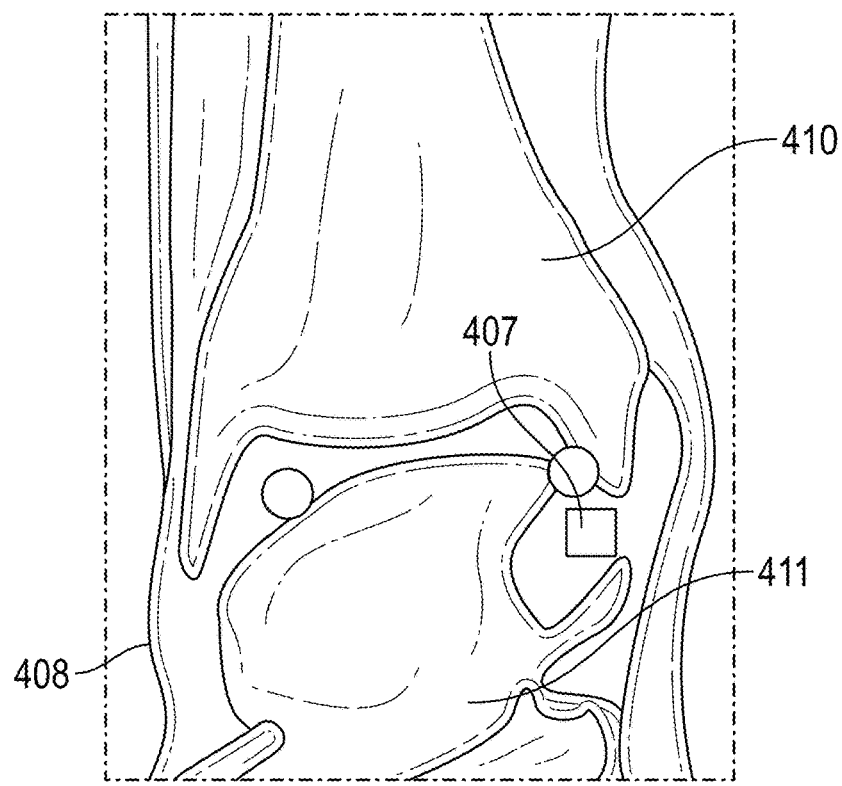
FIG. 30B is the geometric modeling of ankle on MRI coronal view to set up lattice truss structure.
Figure 30C:
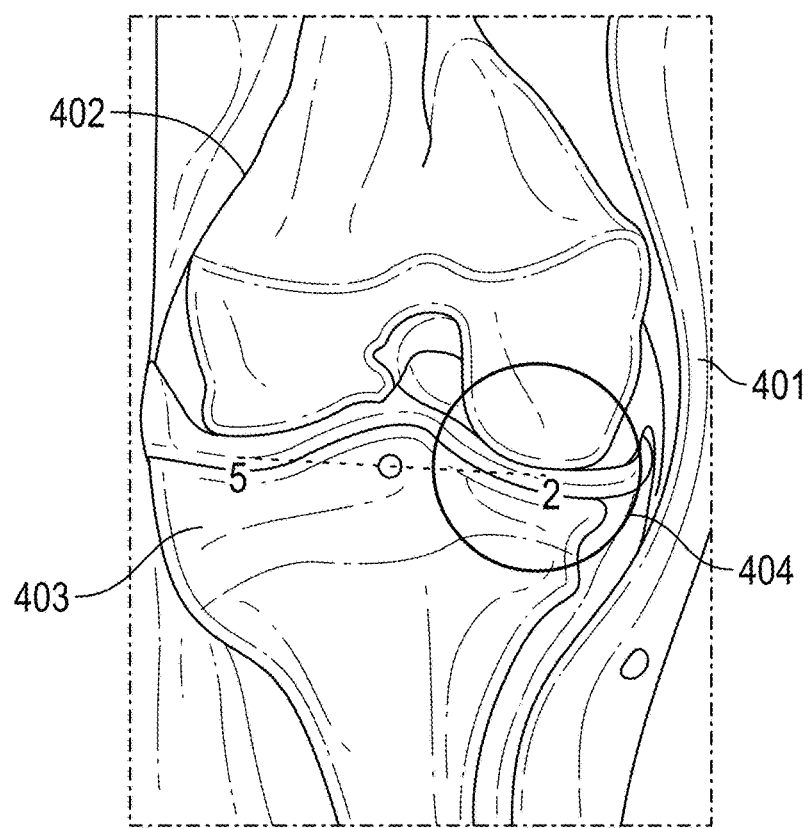
FIG. 30C is the geometric modeling of knee joint on MRI coronal view to set up lattice truss structure.

FIGS. 30A-30C show the MRI images of femoral head, ankle and knee joint, respectively. FIG. 30A displays the circle 405 with the center point 406 of femoral head 413. FIG. 30B defines the medial point 407 and lateral point 408 representing the ankle medial/lateral bounds of ankle where the distal tibia 410 and talus 411 make the contact. FIG. 30C displays a potential joint line with two medial/lateral contact points between distal femur 402 and proximal tibia 403 represented by points 5 and 6. A significant amount bone wear of the medial condyle and medial tibia plateau is visible inside the circle 404.

Figure 31A:
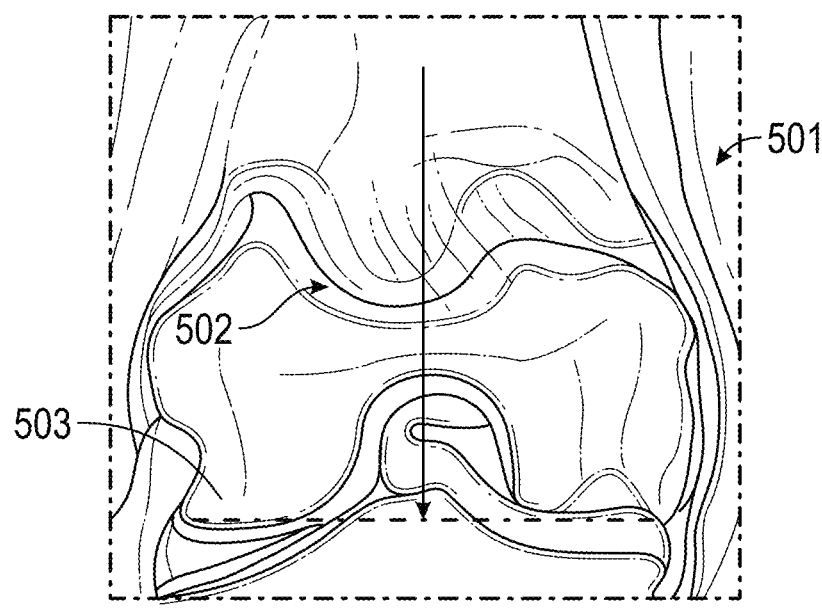
FIG. 31A displays wear vector and femoral joint line using wear algorithm.
Figure 31B:
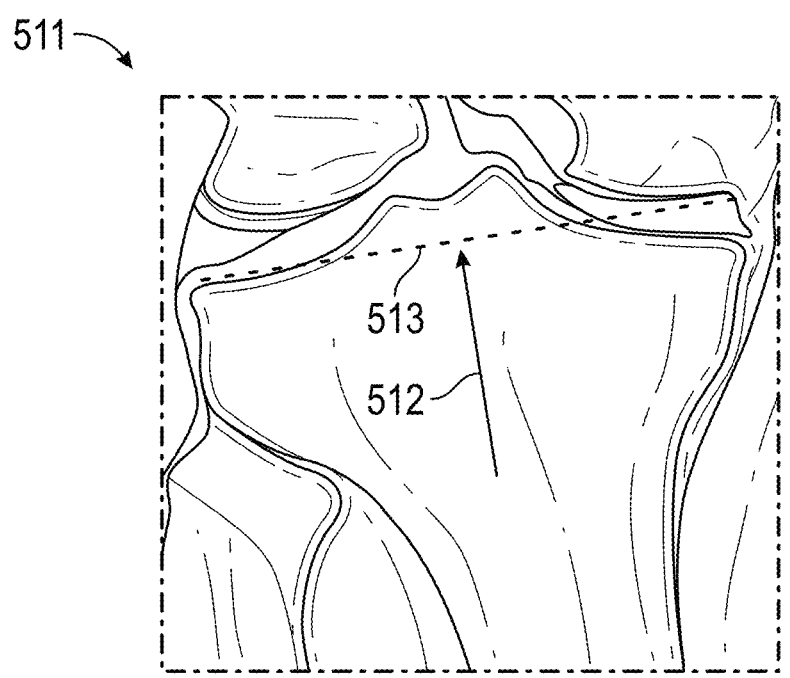
FIG. 31B displays wear vector and tibial joint line using wear algorithm.

FIGS. 31A and 31B show the estimated joint lines of 503 and 513 on distal femur 501 and on proximal tibia 511. The estimation of the two joint lines 503 and 513 is done by the wear algorithm that provides the estimated wear vectors 502, 512 of distal femur 501 and proximal tibia 511, respectively. The femoral joint line 503 and tibial joint line 513 are perpendicular to the femoral wear vector 502 and tibial wear vector 512, respectively.

FIGS. 32A and 32B are the lattice truss structure 610 and medial/lateral bounds 611 diagrams. As shown in the lattice truss structure of FIG. 23A, the estimated joint line 605 is assembled by joining femoral and tibial joint lines 503, 513 estimated by the wear algorithm with respect to the two medial/lateral contact points. The lattice truss structure 610 provides the line 605 intersecting the estimated joint line 605. Therefore, medial/lateral bounds 613 and 612 can be established by parallel to line 605. The next step is to find the gap length of medial/lateral bounds represented by Dmax. It should be noted that Lines 605 and 606 are not necessarily perpendicular each other.

FIG. 32C illustrates an application of Ptolemy's theorem to find a best fit for the lattice truss structure 610 of FIGS. 32A and 32B. Ptolemy's theorem relates the two diagonals and four sides of a cyclic quadrilateral (one whose vertices lie on a common circle). Specifically, the product of the lengths of the two diagonals is equal to the sum of products of the pairs of opposite sides of a cyclic quadrilateral. More generally, it is known that for any quadrilateral ABCD, where the diagonals are AC and BD, a first set of opposite sides are AB and CD, and a second set of opposite sides are BC and AD, $$(|AC|\cdot|BD|)/[(|AB|\cdot|CD|)+(|BC|\cdot|DA|)] \leq 1,$$

wherein the equality (=1) is only true when the vertices A, B, C and D of the quadrilateral ABCD are concircular.

Applying this to the lattice truss structure seen in FIG. 33C, a first quadrilateral BLED for a patient's femur and a second quadrilateral DEGF for a patient's tibia satisfy the corresponding relations:

$$\frac{\overline{BE}\cdot\overline{CD}}{\overline{BC}\cdot\overline{DE}+\overline{BD}\cdot\overline{CE}} = FEMNUM$$

$$\frac{\overline{DG}\cdot\overline{EF}}{\overline{DE}\cdot\overline{FG}+\overline{DF}\cdot\overline{EG}} = TIBNUM$$

$$1 - FEMNUM = \epsilon_f \tag{1}$$

$$1 - TIBNUM = \epsilon_g \tag{2}$$

$$\frac{dF}{D_f} = \varepsilon_p \tag{3}$$

$$\frac{dT}{D_t} = \varepsilon_q \tag{4}$$

Using unconstraint continuous optimization of nonlinear equations (circle), $$OP_f = \min_{\varepsilon}[\varepsilon_f^2 + \varepsilon_p^2] \tag{5}$$

-continued $$OP_t = \min_\varepsilon [\varepsilon_g^2 + \varepsilon_q^2] \quad (6)$$

best fit femur and tibia Ptolemy circles are optimized based on the four points of respective quadrilaterals BCED and DEGF. Each quadrilateral is laid on the circumference of a circle and the respective center point P or Q is laid on the femoral mechanical axis (the line HK between the center of the femoral head and the center of the knee).

Figure 33:
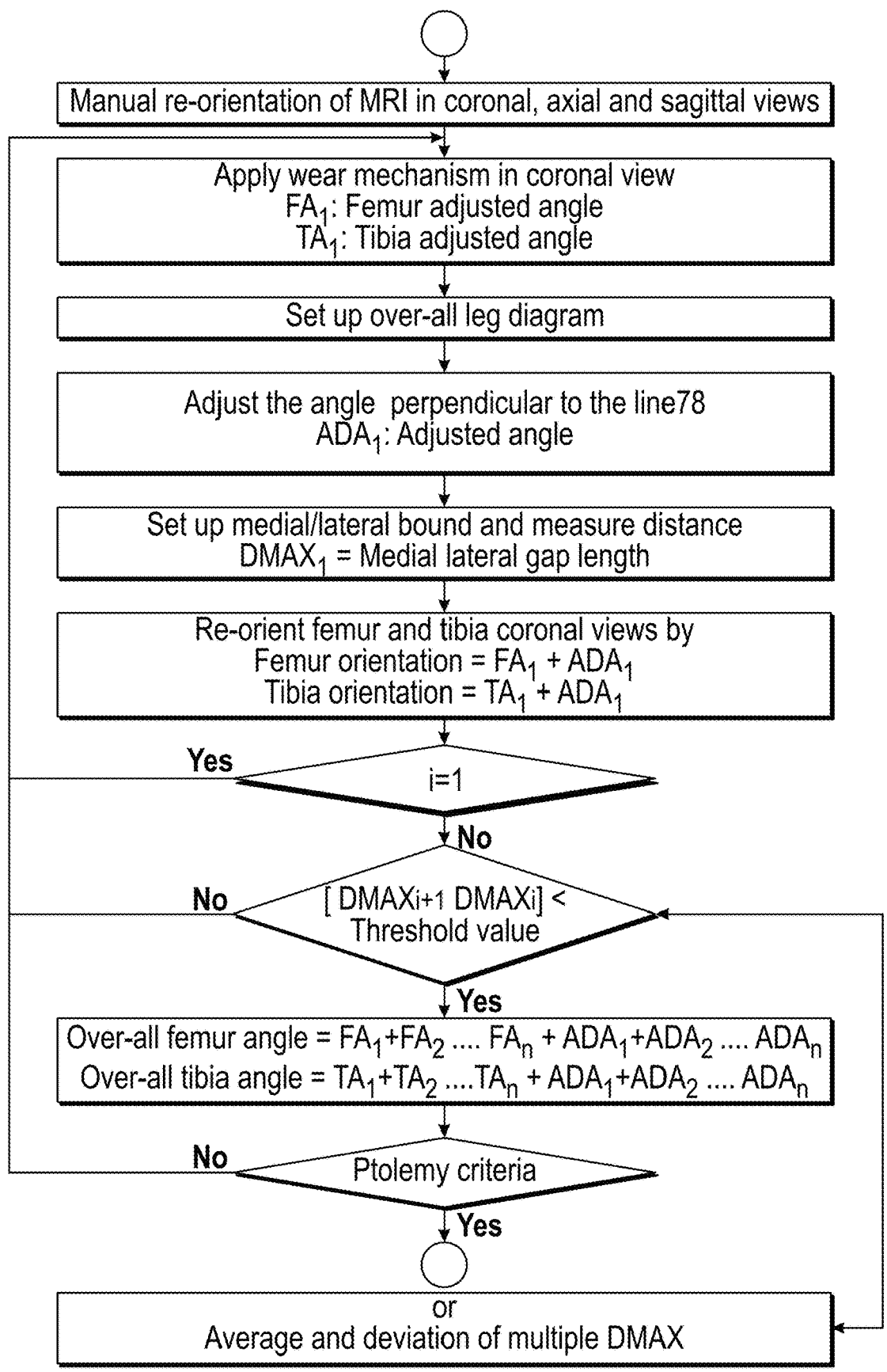
FIG. 33 is the flow chart of the over-all wear mechanism analysis process.

FIG. 33 shows a flow chart of the estimation of the knee joint line. The procedure should be repeated at least twice or more until two or more trials display a consistent result within the threshold value by comparing the two results or average and deviation after number of trails. If after the optimization in FIG. 32C, $OP_f$ and $OP_t$ are less than a threshold value (Ptolemy criteria=Yes), then proceed to the next step; otherwise, the process goes back to wear mechanism analysis.

Figure 34:
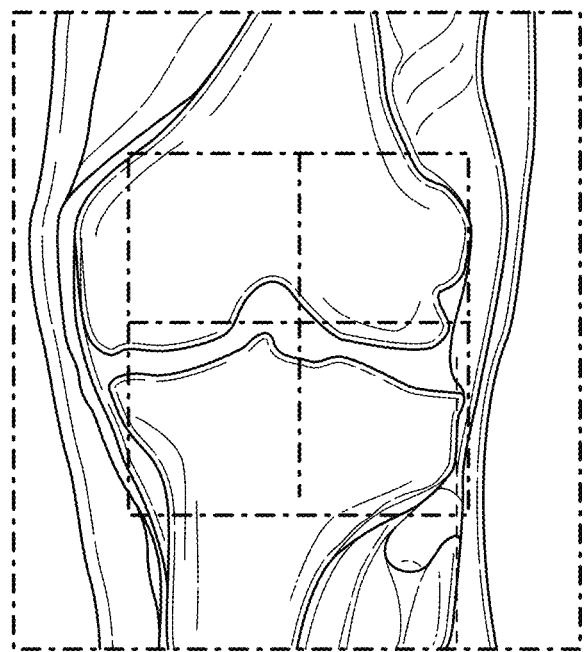
FIGS. 34 and 35 are coronal views of the femur and tibia, respectively, with superimposed implant alignment boxes.
Figure 35:
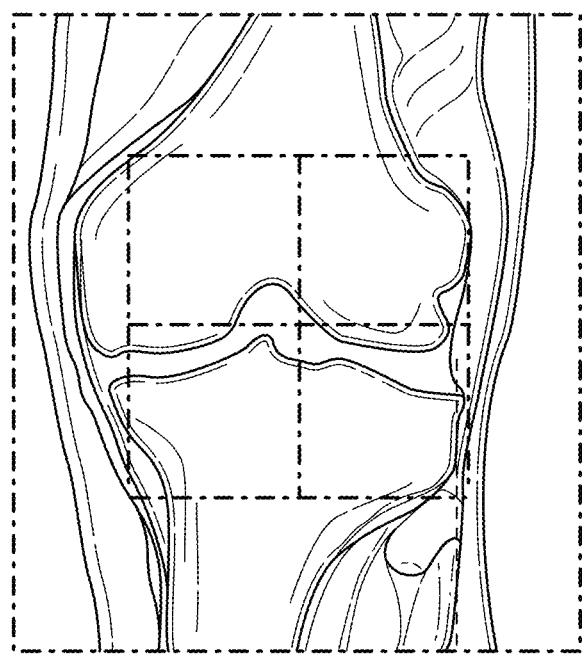
Figure 36:
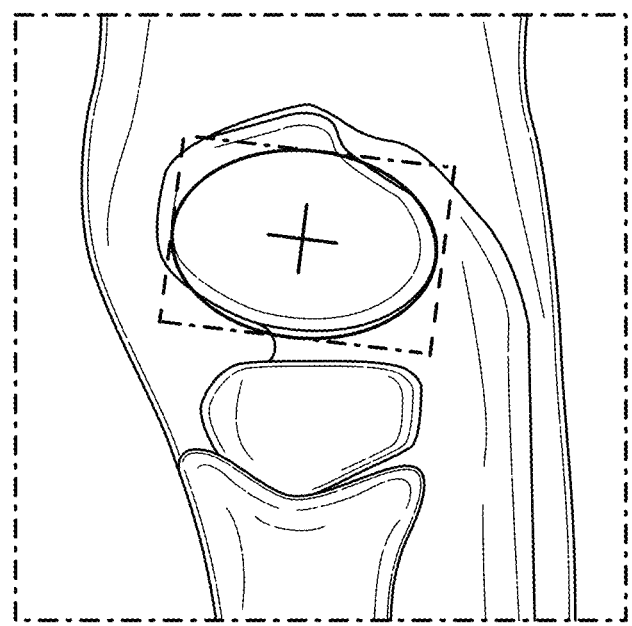
FIG. 36 is a sagittal view of the knee for sagittal implant orientation, showing a superimposed implant alignment box for the femur.
Figure 39C:
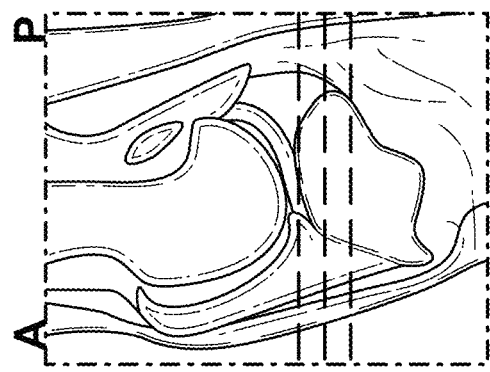
FIGS. 39A-39C are respective coronal, axial, and sagittal views of a knee joint with a choice of superior-inferior positions of the femur implant.
Figure 39B:
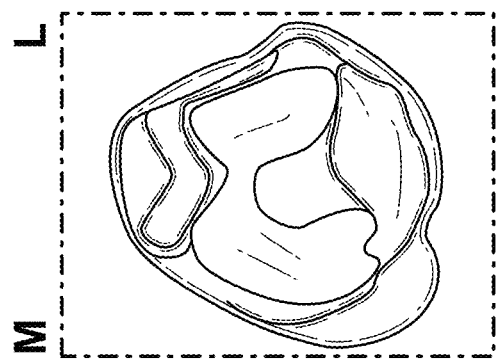
Figure 39A:
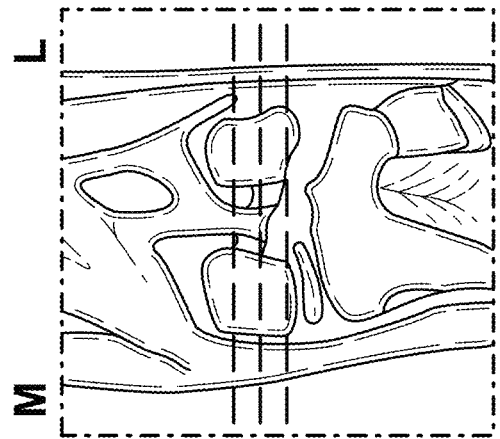
Figure 40C:
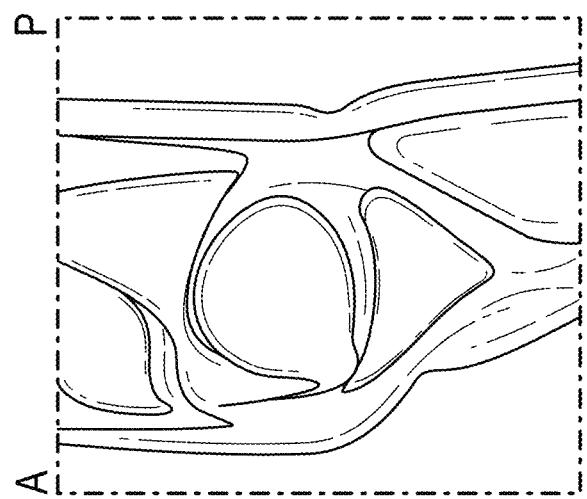
FIGS. 40A-40C are respective coronal, axial, and sagittal views of a knee joint with a choice of medial-lateral positions of the femur implant.
Figure 40B:
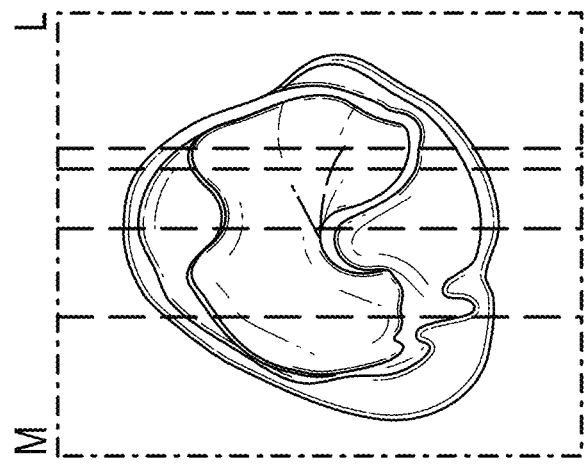
Figure 40A:
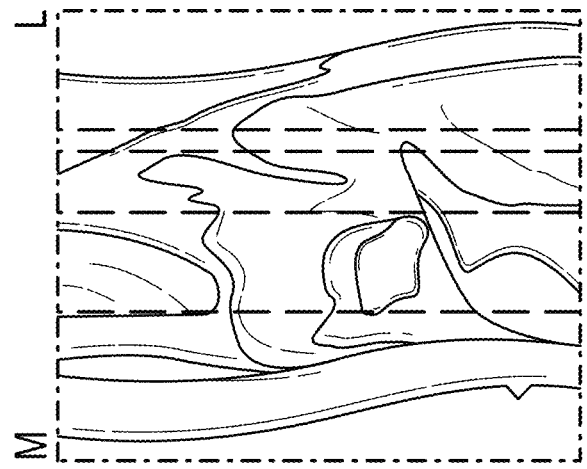

With reference to FIGS. 34 and 35, an alignment check is performed with coronal views of the knee for both the femur and tibia. The boxes superimposed upon the image represent the selected implant orientation (vertical center line) and width dimensions (vertical edge lines) for the respective implants. Likewise, a sagittal view facilitates a sagittal orientation correction. Note, for example, the anterior-posterior pitch for the femur implant shown in FIG. 36. The ellipse will be used for implant positioning in the next steps.

A web or software interface allows orthopedic surgeons to interact with the custom implant design team in order to make certain desired changes to the initial planning data and grant final approval for an implant. Such an interface presents the patient's knee information along with images of the knee and the initially planned femur and tibia implants. Relevant information can include patient's name, chief surgeon's name, date of surgery, implant manufacturer and model, proposed femur and tibia implant sizes, varus/valgus angle of the overall limb, and corresponding resection depths and angles for the femur and tibia. The display can show the respective coronal, axial and sagittal views of the knee with implant outlines superimposed upon such views.

Femoral component positioning is seen in the respective coronal, axial and sagittal views of FIGS. 37A-37C, wherein the coronal and sagittal views overlays the potential implant in outline, and the box seen in the axial view can be manipulated by the custom implant designer to establish the medial-lateral and anterior-posterior position limits for the implant. This includes a femur medial-lateral length $ML_f$ and a femur anterior-posterior length APE. Typically, a set of incremental femur implant sizes (i=1 to n) are available at this point in the implant customization, and it is a matter of selecting the best fit to the patient's femur dimensions based on the images. Starting with an initial best fit, $$I_{sf} = \text{MIN}_{i=1}^n [(ML_f - ML_{fi})^2 + (AP_f - Ap^{fi})^2],$$

the designer can then, in consultation with the surgeon, manually adjust the implant size selection up and down (+/−) if needed. FIGS. 38A-38C, 39A-39C, and 40A-40C illustrate a possible surgeon interface showing coronal, axial, and sagittal views, wherein overlaid sets of parallel lines indicate choices of respective anterior-posterior, inferior-superior, and medial-lateral positions for the implant. Normally the center option is the initially-computed best fit for the implant position; but the surgeon always is given the option of moving the position in either direction to a neighboring position (or even set an intermediate position, where the outer lines represent position limits), if in the judgment of the surgeon it would provide a better patient outcome than the computed value.

Figure 41C:
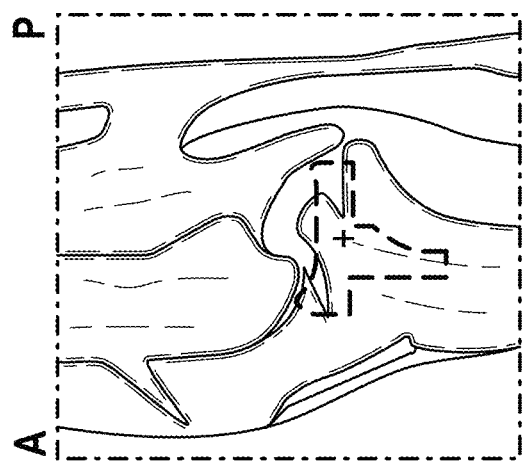
FIGS. 41A-41C are respective coronal, axial, and sagittal views for tibial implant positioning, with superimposed outlines of the planned tibia implant.
Figure 41B:
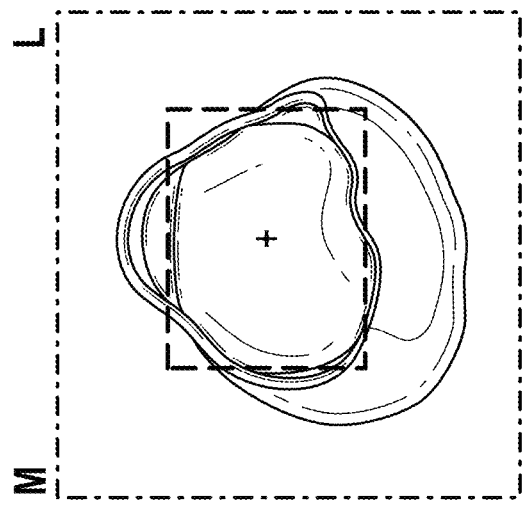
Figure 41A:
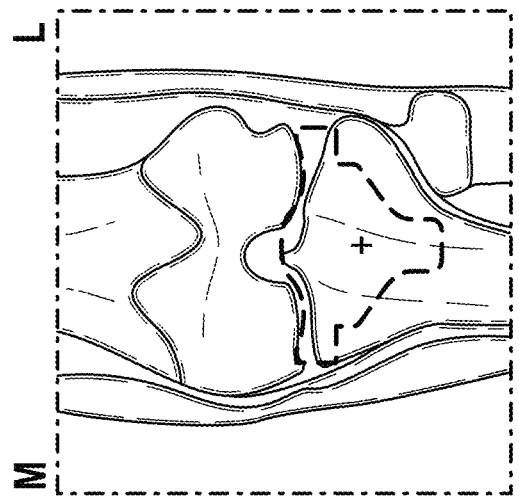
Figure 42C:
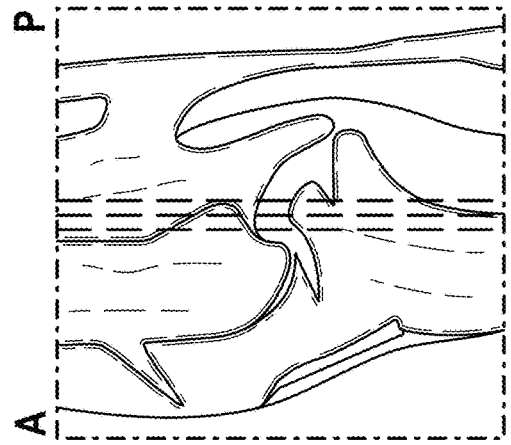
FIGS. 42A-42C are respective coronal, axial, and sagittal views of a knee joint with a choice of anterior-posterior positions for the tibia implant.
Figure 43C:
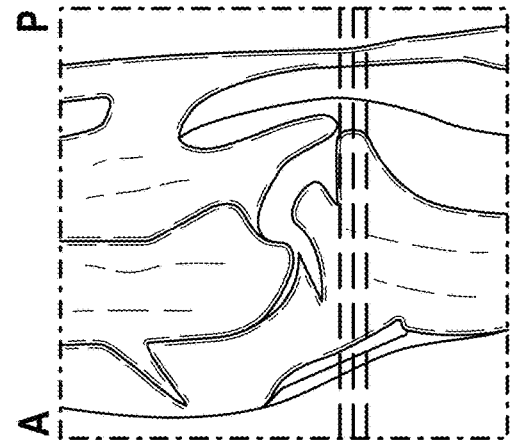
FIGS. 43A-43C are respective coronal, axial, and sagittal views of a knee joint with a choice of superior-inferior positions of the tibia implant.
Figure 42B:
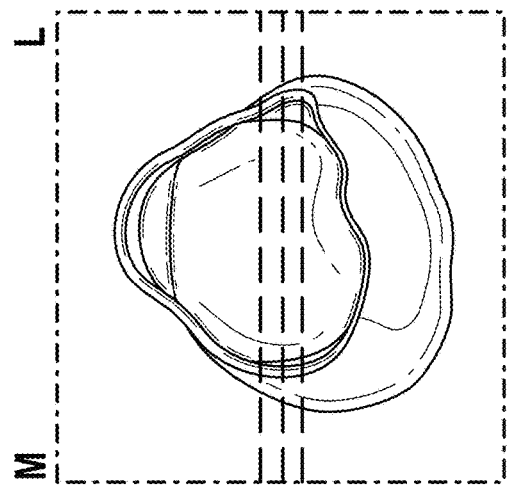
Figure 43B:
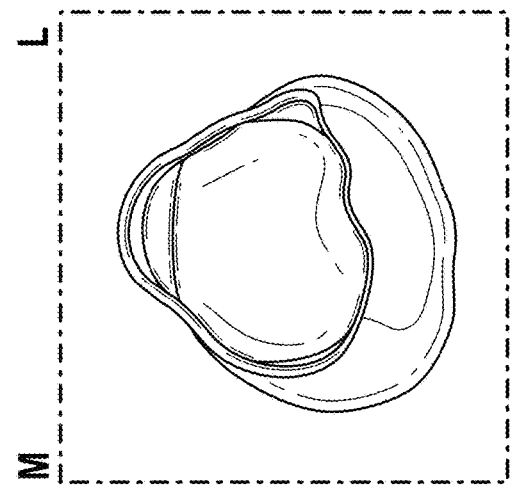
Figure 42A:
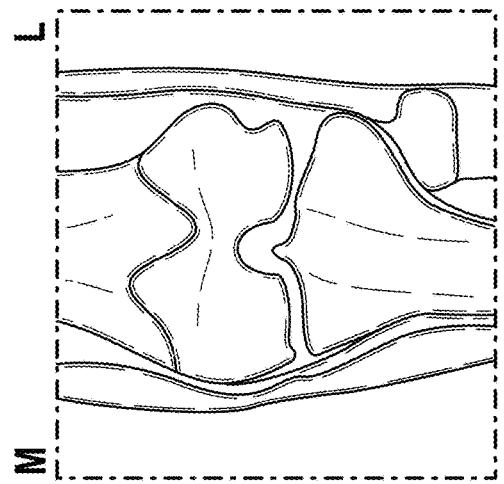
Figure 43A:
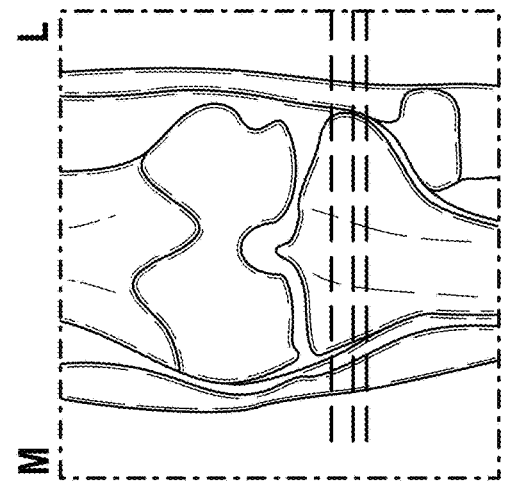
Figure 44C:
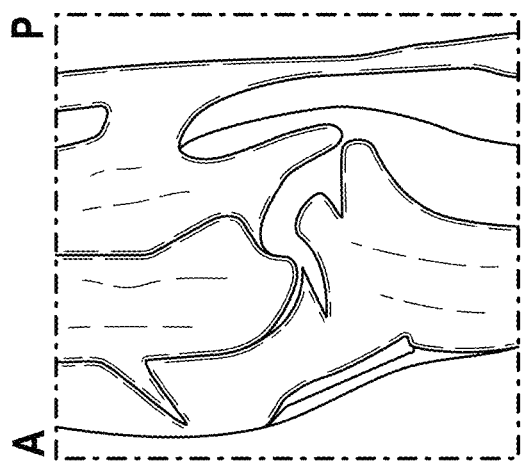
FIGS. 44A-44C are respective coronal, axial, and sagittal views of a knee joint with a choice of medial-lateral positions of the tibia implant.
Figure 44B:
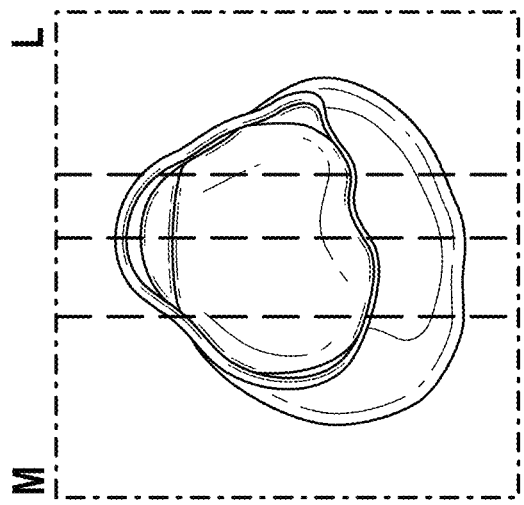
Figure 44A:
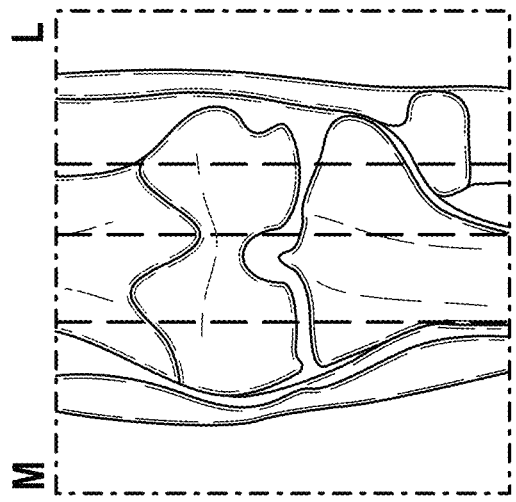

Tibial component positioning is seen in the respective coronal, axial and sagittal views of FIGS. 41A-41C, wherein the coronal and sagittal views overlays the potential implant in outline, and the box seen in the axial view can be manipulated by the custom implant designer to establish the medial-lateral and anterior-posterior position limits for the implant. This includes a tibia medial-lateral length $ML_t$ and a femur anterior-posterior length $AP_t$. Typically, a set of incremental tibia implant sizes (i=1 to n) is available at this point in the implant customization, and it is a matter of selecting the best fit to the patient's tibia dimensions based on the images. Starting with an initial best fit, $$I_{st} = \text{MIN}_{i=1}^n [(ML_t - ML_{ti})^2 + (AP_t - Ap_{ti})^2],$$

the designer can, in consultation with the surgeon, manually adjust the implant size selection up and down (+/−) if needed. FIGS. 42A-42C, 43A-43C, and 44A-44C illustrate a possible surgeon interface showing coronal, axial, and sagittal views, wherein overlaid sets of parallel lines indicate choices of respective anterior-posterior, inferior-superior, and medial-lateral positions for the implant. Normally, the center option is the initially-computed best fit for the implant position; but the surgeon always has the option of moving it in either direction to a neighboring position (or even set an intermediate position, where the outer lines represent positioning limits), if in his/her judgment it would provide a better patient outcome than the computed value.

Surgeon Web Interface in Total Knee Arthroplasty

Figure 45:
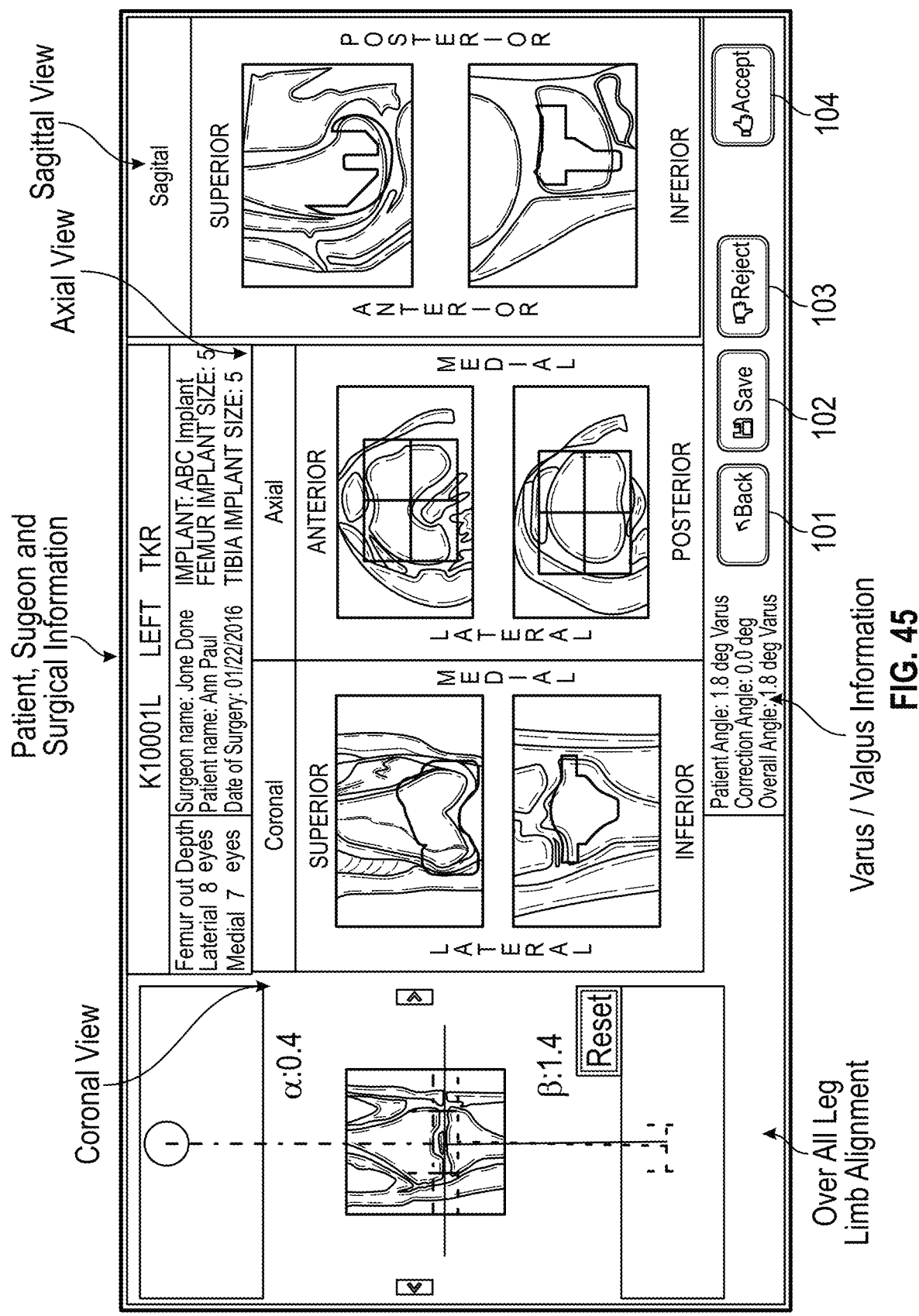
FIG. 45 is a schematic display view of surgeon web interface tool for providing patient knee information, initial alignment recommendations, and interactively providing a surgeon with options for selecting implants and cut planes for total knee arthroplasty. Seen in this view are basic identifying information, an overall leg alignment, varus/valgus information, coronal, axial and sagittal views of a patient's knee, and option/selection buttons.

The Surgeon Web Interface provides orthopaedic surgeons with the patient knee information such as varus/valgus angle, implant size, etc. As shown in FIG. 45, the Surgeon Web interface consists of Over All Leg Limb Alignment located in the left side of the screen. The surgeon and patient information is illustrated on the top of the screen. The information includes the medial/lateral femoral resection depth, surgeon's name and patient's name, date of surgery, implant's manufacturer and femur and tibia implant sizes along with Case Identification. Varus/Valgus over all knee alignment information is displayed at the bottom of the screen along with four buttons of BACK, SAVE, REJECT and ACCEPT. The BACK button displays a previous screen without saving of any surgeon's inputs. The SAVE button commands the system to save any surgeon's inputs and to override the initial planning data. The REJECT button commands the system to resect over-all initial planning or any other reasons by surgeons, and final approval of planning is done by selecting the ACCEPT button. In the middle to right positions, there are clickable coronal, axial and sagittal views with the superposition of the outlines of implant in coronal, sagittal and ML/AP length.

Figure 46:
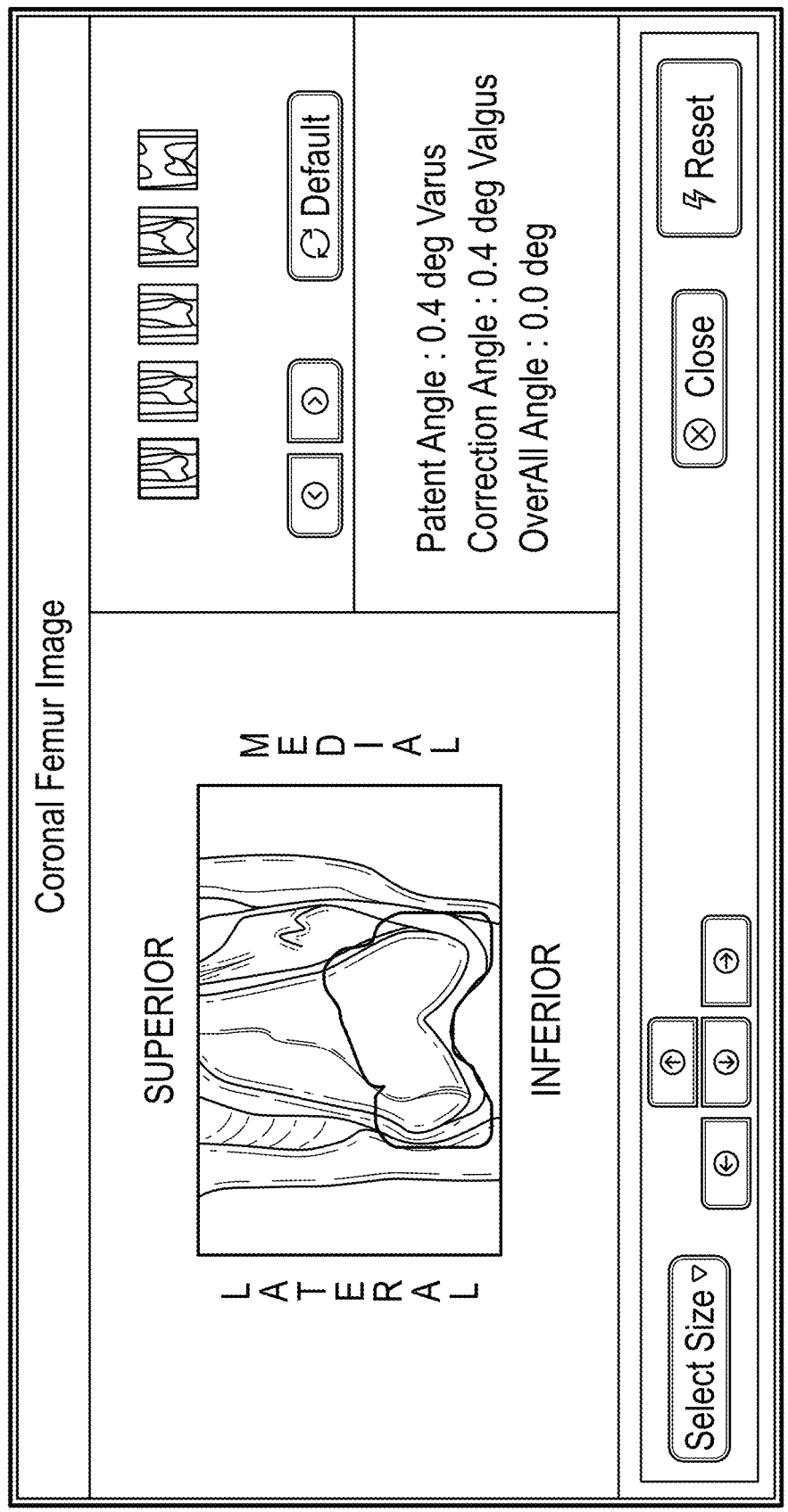
FIG. 46 is a schematic display view of a pop-up window from the web interface tool of FIG. 45, showing views of image slices to assist surgeon planning.

Once the coronal view is selected, the pop-up window is displayed (FIG. 46). The left side is the coronal view of MRI with the superposition of implant outline. The bottom of the screen display left/right and up/down implant translation buttons, the pop-up window close button and reset button. The right side illustrates additional coronal MRI slices to assist the surgeon's planning as well as Varus/Valgus angle illustration. The axial and sagittal views also display identical functions to assist surgeon's planning.

Figure 47:
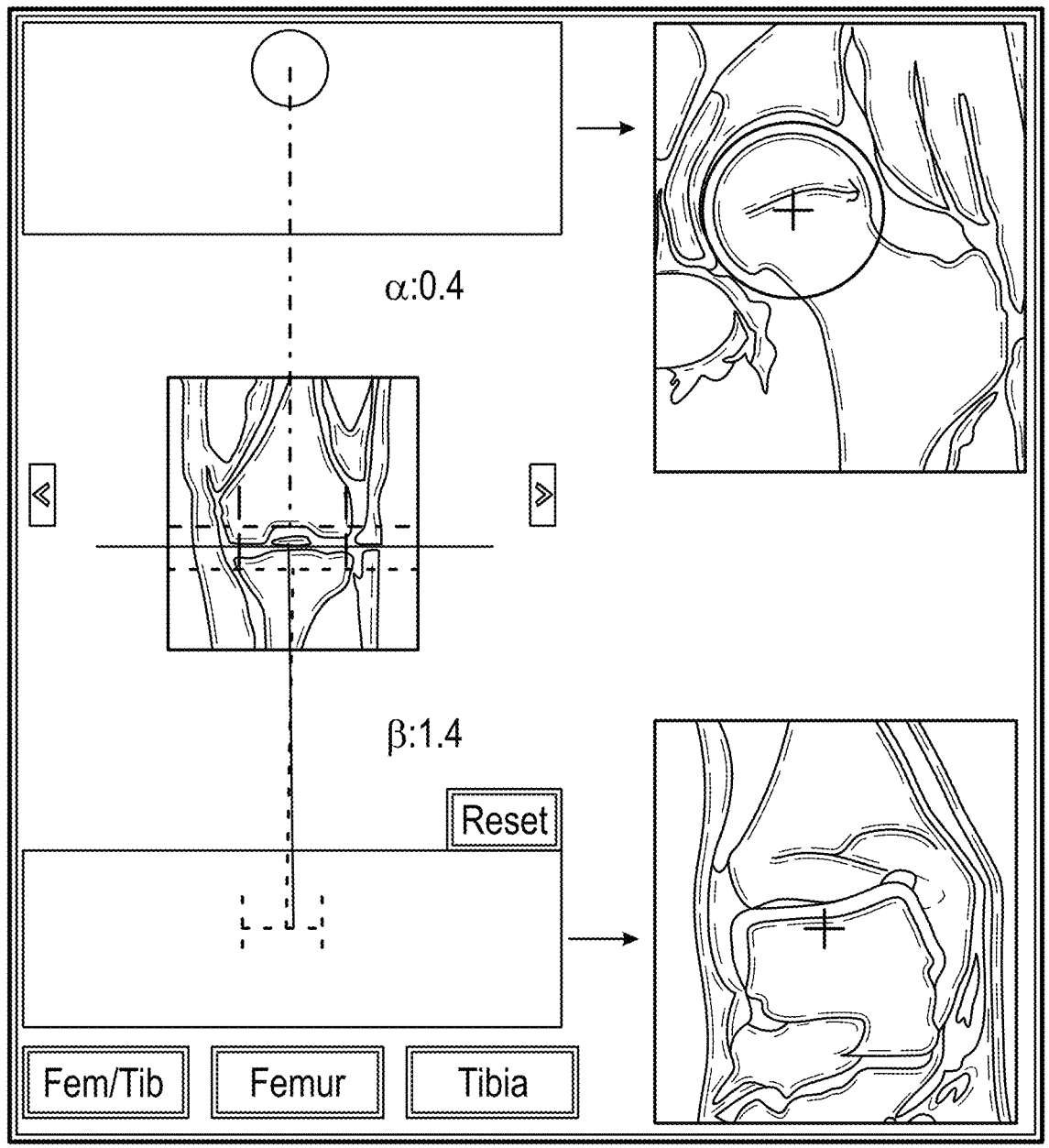
FIG. 47 is a close-up of overall leg alignment from FIG. 45 together with corresponding images of a femoral head (at the hip) and ankle.

FIG. 47 illustrates the overall limb alignment of the leg, while FIG. 51 represents the overall planning flow with the input of a surgeon via an interface. The initial leg alignment is done based on the results of the Planning 1 and Planning 2. The initial resection is set up according to the surgeon's preference, i.e., standard mechanical alignment and absolute mechanical (anatomical) alignment. If surgeon clicks on top light blue area, Pop-up window appears with patient's femoral head of MRI slice where it shows the center of femoral head and the size of the femoral head. Also, if surgeon clicks on bottom light red area, Pop-up window appears with patient's ankle of MRI slice where it shows the center of ankle.

As shown in FIG. 48, H represents the femoral head joint region, K represents Knee joint region with contact interval, and A represents Ankle joint region with contact interval. Furthermore, fm (black dotted line) represents femoral mechanical axis and tm (black dotted line) represents tibial mechanical axis according the standard definition. am represents absolute (anatomical) mechanical axis. Af is the angle between femoral mechanical axis and absolute mechanical axis and At is the angle between tibial mechanical axis and absolute mechanical axis. Surgeons have options to change the surgical angle between the angles Af and At. In other words, surgeon's choice is bounded by 0 to Af and 0 to At.

There are three buttons for surgeons to change the resection angle. The Fem/Tib button is to change the femoral and tibial angle simultaneously according to the following algorithm:
1) As=max (Af,At)
2) If As<0.5 degree, then surgeon's choice is either standard mechanical or absolute mechanical approach. N=1
3) If 0.5<As<1.0 degree, then an increment of 2 is introduced. Therefore, surgeon's choice becomes Af, Af/2 and 0 for the femur, and At, At/2 and 0 for the tibia. N=2
4) If 1.0<As<1.5 degree, then an increment of 3 is introduced. Therefore, surgeon's choice becomes Af, 2Af/3, Af/3 and 0 for the femur, and At, 2At/3, At/3 and 0 for the tibia. N=3
Consequently, if 0.5N>As >0.5N-0.5 degree, then an increment of N is introduced, and surgeon's choice is:
CAf=Af, (N−1)Af/N, (N−2)Af/N, and 0 for femur;
CAt=At, (N−1)At/N, (N−2)At/N, . . . , and 0 for tibia.

N represents the number of clicks available between standard and absolute mechanical alignment. Default position is either standard mechanical alignment or absolute mechanical alignment base on surgeon's preference. The click (arrow) buttons are positioned in the middle of diagram for surgeon's to conveniently change the varus/valgus planning. FIG. 49A illustrates the standard mechanical alignment and its resection of femur and tibia. FIG. 49C shows the absolute mechanical (anatomical) alignment resections. From standard mechanical alignment to absolute mechanical alignment resections of femur and tibia requires N number of arrow clicks. FIG. 49B shows the femoral and tibial resections between standard mechanical and absolute mechanical resections.

The Tibia button is to change the tibial angle only according to the following algorithm:
1) If At<0.5 degree, the surgeon's choice is either standard mechanical or absolute mechanical BOUND. N=1
2) If 0.5<At<1.0 degree, n increment of 2 is introduced. Therefore, surgeon's choice becomes At, At/2 and 0 for tibia ONLY. N=2
3) If At >1.0 degree, an increment of 3 is introduced. Therefore, surgeon's choice becomes At, 2At/3, At/3 and 0 for tibia ONLY. N=3

Consequently, if 0.5N>At >0.5N-0.5 degree, an increment of N is introduced. Therefore, surgeon's choice is CAt=At, (N−1)At/N, (N−2)At/N, . . . , and 0 for tibia ONLY.

FIG. 50A is standard mechanical alignment resection as surgeon's preference. By clicking Arrow buttons, surgeons change only tibial resection angle, while femoral resection angle is fixed as shown in FIG. 50B. The change of tibial resection angle is bounded between the standard and absolute mechanical angles.

The Femur button is to change the femoral angle only according to the following algorithm:
1) If Af<0.5 degree, the surgeon's choice is either standard mechanical or absolute mechanical BOUND. N=1
2) If 0.5<Af<1.0 degree, an increment of 2 is introduced. Therefore, surgeon's choice becomes Af, Af/2 and 0 for femur ONLY. N=2
3) If Af>1.0 degree, an increment of 3 is introduced. Therefore, surgeon's choice becomes Af, 2Af/3, Af/3 and 0 for femur ONLY. N=3
Consequently, if 0.5N>Af>0.5N-0.5 degree, then an increment of N is introduced. Therefore, surgeon's choice is CAf=Af, (N−1)Af/N, (N−2)Af/N, . . . , and 0 for femur ONLY.

FIG. 50A is standard mechanical alignment resection as surgeon's preference. By clicking Arrow buttons, surgeons change only femoral resection angle while tibial resection angle is fixed as shown in FIG. 50C. The change of femoral resection angle is bounded between the standard and absolute mechanical angles.

As shown in FIG. 47, the femoral angle α is the angle between femoral resection angle and absolute mechanical angle and the tibial angle β is the angle between tibial resection angle and absolute mechanical angle. If surgeon chooses the standard mechanical alignment resection, then α=Af and β=At. On the other hand, if surgeon chooses the absolute mechanical alignment resection, then α=0 and β=0.

Also, the bottom of FIG. 45 illustrates patient's overall limb alignment.

Patient Angle (PA) is the absolute values of the sum of Af and At, where the positive value represents varus and negative value represents valgus:

$$PA = |Af + At|$$

If Af>0, then femoral angle is varus.
If Af<0, then femoral angle is valgus.
If At>0, then tibial angle is varus.
If At<0, then tibial angle is valgus.
If Af+At>0, then overall limb alignment angle is varus.
If Af+At<0, then overall limb alignment angle is valgus.

Correction Angle (CA=CAf+CAt) represents the surgeon's change on the overall limb alignment.

$$\text{Overall Angle } (OA) = CA$$

If the surgeon's choice is a standard mechanical alignment, then OA=0. On the other hand, if the surgeon's choice is an absolute mechanical alignment, then OA=PA.

If the surgeon selects the <RESET> Button, the planning goes back to the initial setting.

Figure 52:
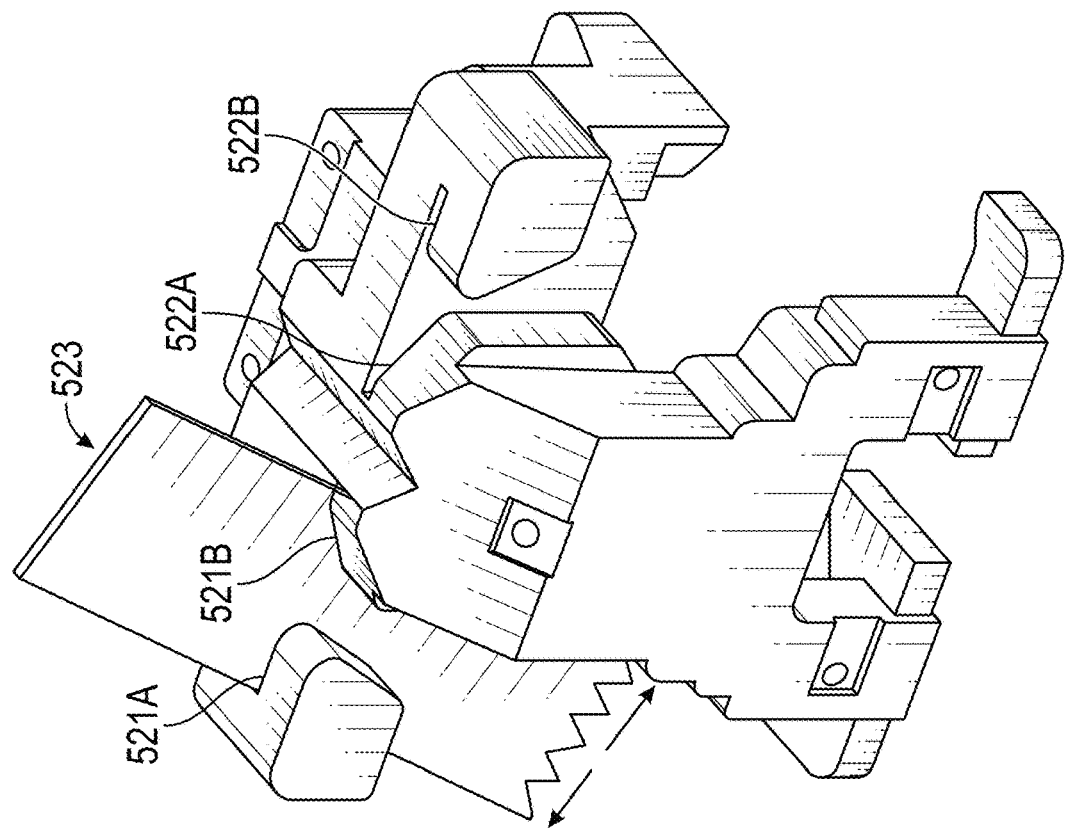

With reference to FIG. 52, a femur jig constructed using the parameters determined by the present invention may have any of several options provided as special features according to the surgeon's choice. Among these optional features are double slits 521A and 521B (or 522A and 522B for the opposite side of the femur) that engage both sides of a reciprocal saw 523 and allow for oscillatory motion of the saw 523 while remaining in the defined cut plane because of those double slits 521A and 521B (or 522A and 523B).

Figure 53:
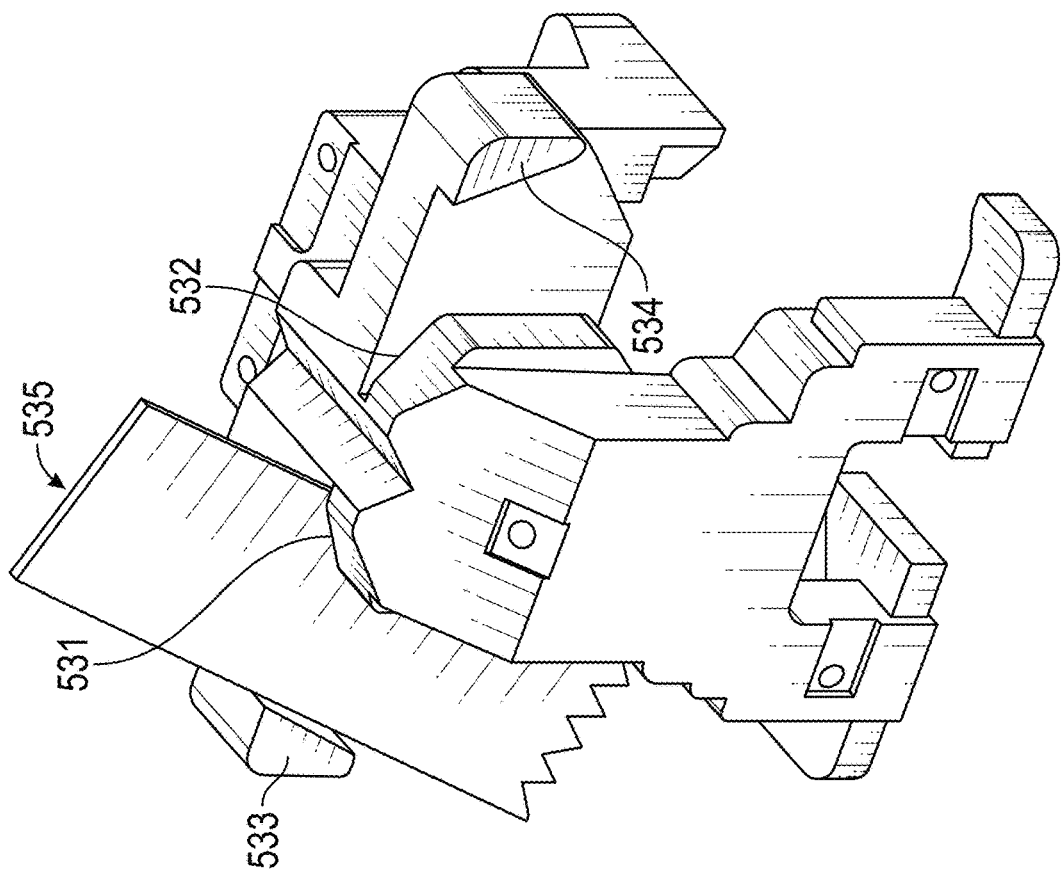
FIGS. 52-54 are perspective views of three possible femur jig embodiments sized according to parameters defined by the present invention.

FIG. 53 shows another femur jig having a single slit 531 (or 532 for the opposite side of the femur) which is combined with a corresponding saw blocker 533 (or 534 for the opposite side of the femur). Together the slit and saw blocker allow a reciprocal saw 535 to provide a cutting motion against the femur while being limited in motion in one direction by the saw blocker 533 (or 534). The single slit 531 (or 532) still provides sufficient definition of the cut plane for the saw 535.

Figure 54:
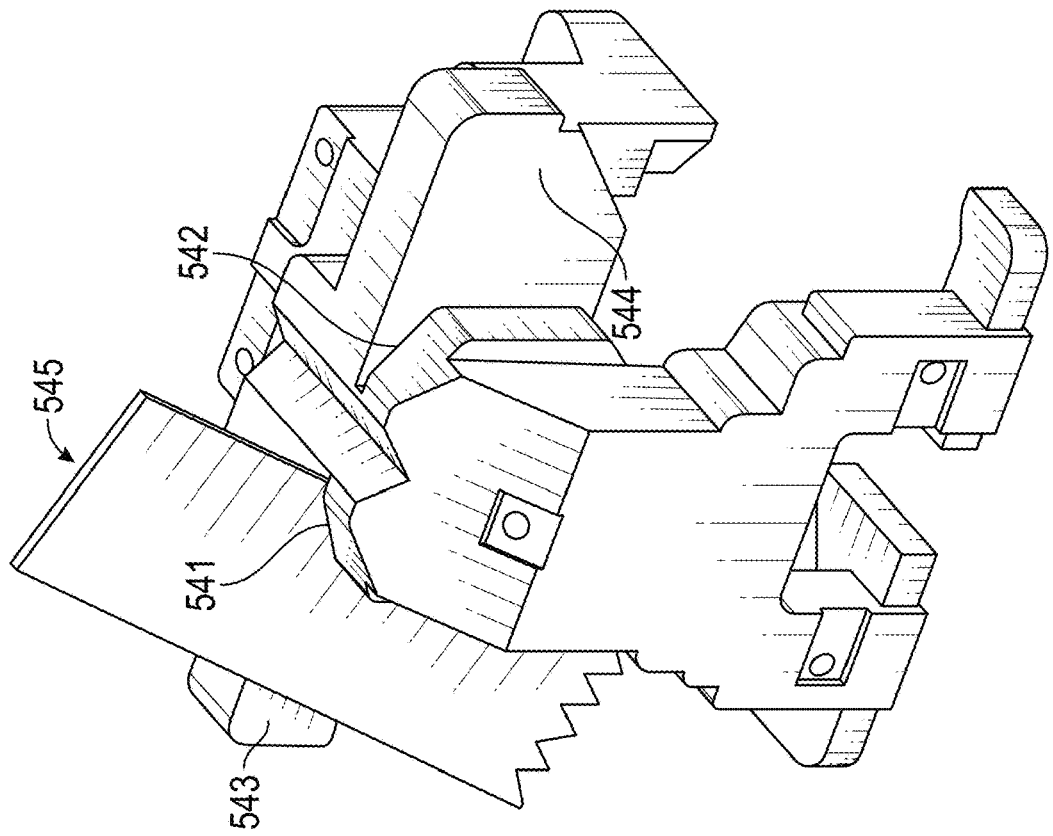

FIG. 54 shows yet another femur jig provided with open ends 543 and 544 for maximum degree of freedom for the saw 545. The jig still contains a set of slits 541 and 542 for engaging the saw 545 on each side of the femur.

Figure 55:
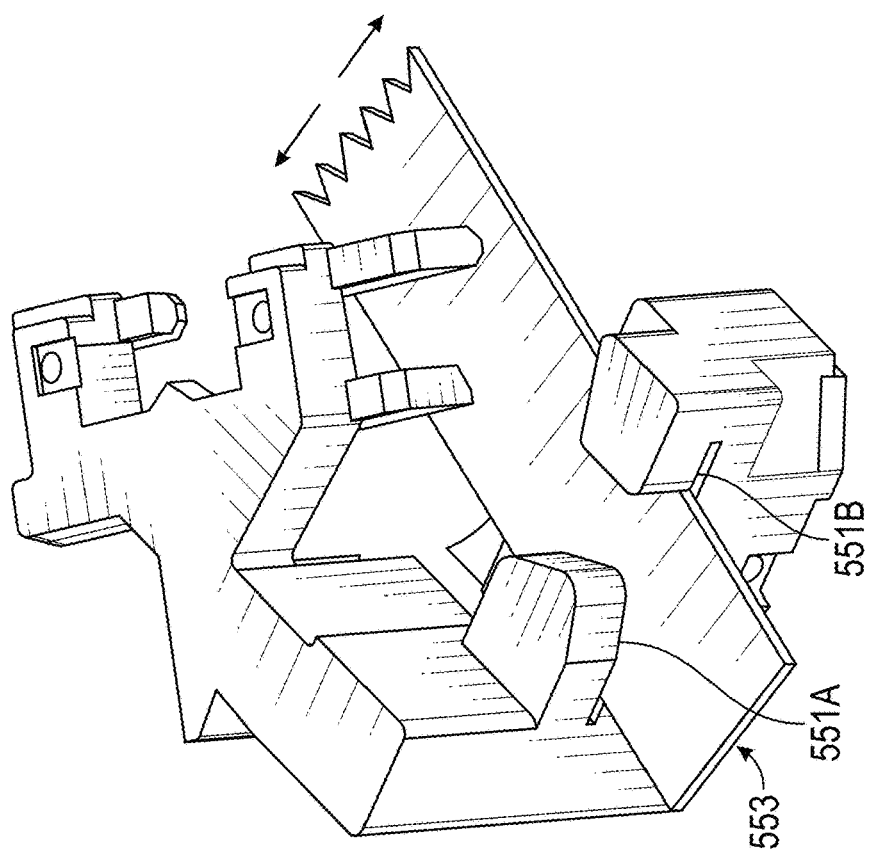
FIGS. 55-57 are perspective view of three possible tibia jig embodiments sized according to parameters defined by the present invention.
Figure 57:
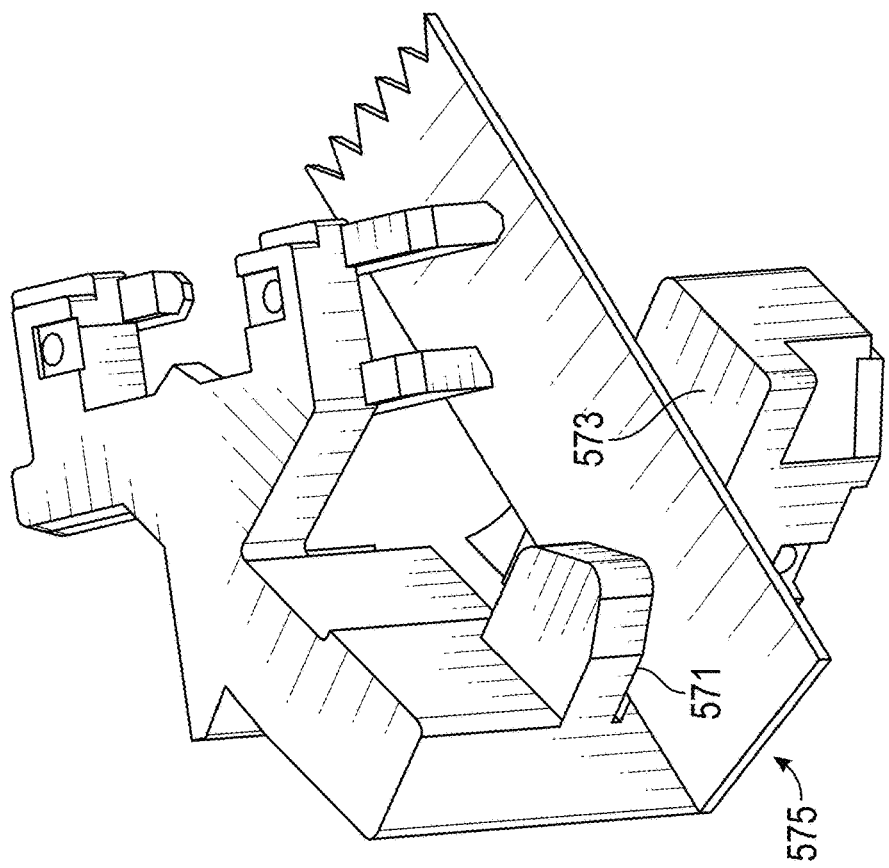
Figure 56:
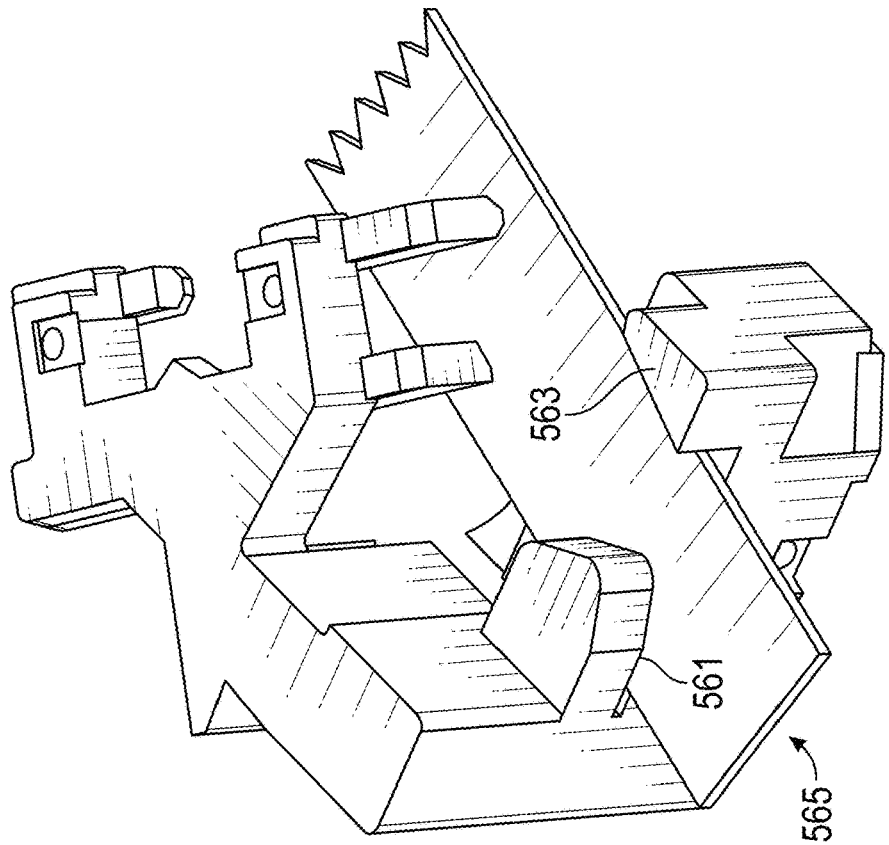

FIGS. 55-57 show corresponding tibia jigs with similar features. In FIG. 55, the jib has double slits 551A and 551B for engaging both sides of a reciprocal saw 553, allowing for a range of saw oscillation while maintaining the saw in the desired tibial cut plane. In FIG. 56, a single slot 561 is provided on one side of the reciprocal saw 565, while the other side engages against a saw blocker 563 that limits saw motion in that one direction. In FIG. 57, the saw 575 has maximum freedom of motion because of the open end 573, while being maintained in the defined cut plane by the single slot 571.

In all cases, whether of the femur jig or tibia jig, and whatever choice of surgeon options for the range of motion allowed for the reciprocal saw, the jigs are constructed according to dimensions determined from the series of patient-specific images according to the techniques described above, so that a jig has one and only one mechanical self-locking position against the bone (and associated cartilage). Accordingly, the jig's bone cutting guide (the provided slot or slots) define a single specified cut plane for re-sectioning per the desired limb alignment.

What is claimed is:

1. A computer-aided method using an interactive pre-operative planning software analysis tool for establishing, from patient-specific images, femur and tibia cut planes and implant sizes for knee replacement surgery, the method comprising:
    obtaining, and inputting as image data into a computer system, a series of images of a leg of a patient, including at least one whole-leg coronal image showing hip, knee, and ankle, and a set of coronal, axial and sagittal image slices of respective hip, knee, and ankle joints representing a current anatomical condition of a patient;
    determining by the computer system a set of coordinates of selected hip, knee and ankle features in the image data;
    estimating from the determined set of coordinates, based upon a joint anatomical-matching wear mechanism carried out by the computer system, a pre-arthritic tibio-femoral mechanical alignment of the leg;
    establishing, through user interaction with the pre-operative planning software analysis tool in the computer system, a desired tibio-femoral mechanical alignment of the leg within bounds defined between the estimated pre-arthritic alignment and a fully neutral alignment;
    determining a cut plane for at least one of a femoral and tibial surgical jig in accord with the desired tibio-femoral mechanical alignment; and
    constructing the at least one surgical jig with a set of bone-jig contact surfaces that are dimensioned from the image data such that the jig has one and only one mechanical self-locking position, the jig having a bone cutting guide that defines the cut plane as per the desired alignment.

2. The method as in claim 1, wherein the pre-arthritic tibio-femoral mechanical alignment of the leg is estimated using coronal plane images of the entire limb from hip to knee to ankle.

3. The method as in claim 2, wherein the pre-arthritic tibio-femoral mechanical alignment of the leg is further estimated from an analysis of joint wear mechanisms using coronal, axial and sagittal image slices of the knee.

4. The method as in claim 1, wherein the pre-arthritic tibio-femoral mechanical alignment of the leg is estimated to within about 0.5 degree.

5. The method as in claim 1, wherein a desired tibio-femoral mechanical alignment is any one of a within two degrees of neutral alignment, a varus (bowlegged) alignment of more than two degrees from neutral alignment, and a valgus (knock-kneed) alignment of more than two degrees from neutral alignment.

6. The method as in claim 1, wherein a desired tibio-femoral mechanical alignment is selected to assure a total range of knee motion of at least 90 degrees.

7. The method as in claim 1, wherein a desired tibio-femoral mechanical alignment is selected by offering a range of surgeon choices including the estimated pre-arthritic alignment and one or more closer-to-neutral alignments within three degrees of the estimated pre-arthritic alignment.

8. The method as in claim 7, wherein a desired tibio-femoral mechanical alignment is selected by also taking due regard to any one or more of a condition of an associated hip joint, and an alignment of an opposite limb, as evidenced by the series of images.

9. The method as in claim 1, wherein determining a cut plane in accord with the desired tibio-femoral mechanical alignment includes separately establishing femoral and tibial cut planes for orienting respective femoral and tibial implants of an artificial replacement joint.

10. The method as in claim 1, further selecting, using the series of image slices of the knee, a best fit of femoral and tibial implant size and positioning.

11. A computer-aided method using an interactive pre-operative planning software analysis tool of total knee replacement for selecting femoral and tibial implant size and positioning and cut plane orientations based upon patient-specific images of a leg, the method comprising:
    obtaining, and inputting as image data into a computer system, a series of images of a leg of a patient, including at least one whole-leg coronal image showing hip, knee, and ankle, and a set of coronal, axial and sagittal image slices of respective hip, knee, and ankle joints representing a current anatomical condition of a patient;
    marking, by means of the interactive software analysis tool in the computer system operating upon the image data, of coordinate positions and sizes of a femoral head, distal tibia ankle joint, and of a knee joint in at least a selected subset of the respective coronal, axial and sagittal image slices;
    performing by the computer system a joint anatomical-matching and wear mechanism analysis based upon the marked coordinate positions to estimate from the image data, a pre-arthritic tibio-femoral mechanical alignment of the leg;
    performing by the computer system a best fit analysis of femur and tibia implant size and positioning from at least a selected subset of the respective coronal, axial and sagittal image slices in the image data;

offering by the interactive software analysis tool a range of surgeon choices for the implant size and positioning including the computed best fit size and positioning and at least one adjacent size and positioning that is displayed overlaid with corresponding image slices and saving a surgeon implant size and positioning choice;

offering by the interactive software analysis tool a range of surgeon choices for tibial-femoral mechanical alignment including the estimated pre-arthritic alignment and at least one closer-to-neutral alignment and saving a surgeon alignment choice;

determining by the computer system respective cut planes for femoral and tibial surgical jigs in accord with the surgeon alignment choice and that is displayed overlaid with corresponding image slices for surgeon verification; and constructing femoral and tibial surgical jigs with a set of bone-jig contact surfaces dimensioned from the series of images such that the jig has one and only one mechanical self-locking position, each jig having a bone cutting guide that defines its respective cut plane as per the surgeon alignment choice.

12. The method as in claim 11, wherein coordinate positions of the knee joint include any one or more of distal femur center, medial-lateral distal femur length and contact points, anterior-posterior distal femur length and endpoints, femur segmentation, proximal tibia center, medial-lateral proximal tibia line and endpoints, anterior-posterior proximal tibia length and endpoints, and tibia segmentation.

13. The method as in claim 12, wherein coordinate positions are transformed onto orthogonal axes corresponding to left-right, anterior-posterior, and inferior-superior directions of the leg, the coordinates being separately transformed about marked coordinate positions of the respective distal femur center and posterior tibia center as origins.

14. The method as in claim 12, wherein the wear model analysis is performed based upon a lattice truss modeling of the marked coordinate positions of the femoral head, knee joint and ankle.

15. The method as in claim 14, wherein the wear model analysis is further performed based upon the femur segmentation and tibia segmentation in the knee joint and upon associated wear vectors, anticipated longitudinal (compression) stress and anticipated tangential (shear) stress of the knee joint, and applying calculated wear in reverse to obtain a pre-arthritic condition of the knee joint.

16. The method as in claim 11, wherein the at least one closer-to-neutral alignment for the surgeon alignment choice is limited to at most three degrees from the estimated pre-arthritic alignment.

* * * * *